US011162082B2

(12) United States Patent
Zeng et al.

(10) Patent No.: US 11,162,082 B2
(45) Date of Patent: Nov. 2, 2021

(54) MUTANT PHOSPHOSERINE AMINOTRANSFERASE FOR THE CONVERSION OF HOMOSERINE INTO 4-HYDROXY-2-KETOBUTYRATE

(71) Applicant: METABOLIC EXPLORER, Saint Beauzire (FR)

(72) Inventors: An-Ping Zeng, Rosengarten (DE); Chengwei Ma, Hamburg (DE); Yujun Zhang, Hamburg (DE)

(73) Assignee: METABOLIC EXPLORER, Saint Beauzire (FR)

(*) Notice: Subject to any disclaimer, the term of this patent is extended or adjusted under 35 U.S.C. 154(b) by 0 days.

(21) Appl. No.: 16/754,903

(22) PCT Filed: Oct. 10, 2018

(86) PCT No.: PCT/EP2018/077542
§ 371 (c)(1),
(2) Date: Apr. 9, 2020

(87) PCT Pub. No.: WO2019/072883
PCT Pub. Date: Apr. 18, 2019

(65) Prior Publication Data

US 2021/0198639 A1 Jul. 1, 2021

(30) Foreign Application Priority Data

Oct. 10, 2017 (EP) .................................... 17306366

(51) Int. Cl.
*C12N 15/20* (2006.01)
*C12N 9/10* (2006.01)
*C12N 15/52* (2006.01)
*C12P 7/18* (2006.01)
*C12P 7/24* (2006.01)
*C12P 7/42* (2006.01)

(52) U.S. Cl.
CPC ........... *C12N 9/1096* (2013.01); *C12N 15/52* (2013.01); *C12P 7/18* (2013.01); *C12P 7/24* (2013.01); *C12P 7/42* (2013.01); *C12Y 206/01052* (2013.01)

(58) Field of Classification Search
CPC .............................. C12N 15/52; C12N 9/1096
See application file for complete search history.

(56) References Cited

U.S. PATENT DOCUMENTS 10,920,255 B2 * 2/2021 Skerra ..................... C12P 13/06

FOREIGN PATENT DOCUMENTS

WO WO 2007/077041 A1 7/2007
WO WO 2009/068110 A1 6/2009
WO WO 2010/037843 A1 4/2010
WO WO 2010/076324 A1 7/2010
WO WO 2012/001003 A1 1/2012
WO WO 2012/004247 A1 1/2012
WO WO 2013/001055 A1 1/2013
WO WO 2014/009435 A1 1/2014
WO WO 2016/162442 A1 10/2016

OTHER PUBLICATIONS

Ali et al., "Biochemical and functional characterization of phosphoserine aminotransferase from Entamoeba histolytica, which possesses both phosphorylated and non-phophorylated serine metabolic pathways", Molecular & Biochemical Parsitology, 2006, vol. 145. pp. 71-83 (13 pages).

Anderson, "Growth Requirments of Virus-Resistant Mutants of *Escherichia coli* Strain "B"". Proc. N.A.S., Mar. 21, 1946, vol. 32, pp. 120-128 (9 pages).

Author unknown, "DATABASE UniProt", URL: http://www.uniprot.org/uniprot/A0A0J7MIE7.txt?version=14, Database Accession No. A0A0J7MIE7, Oct. 14, 2015, XP002775954, 2 pages.

Author unknown, "DATABASE UniProt", URL: http://www.uniprot.org/uniprot/A0A0S8DZ98.txt?version=11, Database Accession No. A0A0S8DZ98, Feb. 17, 2016, XP002775951, 2 pages.

Author unknown, "DATABASE UniProt", URL: http://www.uniprot.org/uniprot/A0A1F4I8T3.txt?version=4, Database Accession No. A0A1F4I8T3, Feb. 15, 2017, XP002775955, 2 pages.

Author unknown, "DATABASE UniProt", URL: http://www.uniprot.org/uniprot/A0A1F6TZ02.txt?version=4, Database Accession No. A0A1F6TZ02, Feb. 15, 2017, XP002775953, 2 pages.

Author unknown. "DATABASE UniProt". URL: http://www.uniprot.org/uniprot/A0A1V2T5D7.txt?version=3, Database Accession No. A0A1V2T5D7, Jun. 7, 2017, XP002786827, 2 pages.

Author unknown, "DATABASE UniProt". URL: http://www.uniprot.org/uniprot/V2UML7.txt?version=30, Database Accession No. V2UML7, Jan. 22, 2014, XP002775952, 2 pages.

(Continued)

*Primary Examiner* — Tekchand Saidha
(74) *Attorney, Agent, or Firm* — Birch, Stewart, Kolasch & Birch, LLP

(57) ABSTRACT

Provided is a genetically modified microorganism for the production of a derivative of 4-hydroxy-2-ketobutyrate selected in the group consisting of 1,3-propanediol, 3-hydroxypropionaldehyde, 3-hydroxypropionate and 2,4-dihydroxybutyrate, the microorganism further having a gene coding for a mutant phosphoserine aminotransferase having an improved L-homoserine aminotransferase activity converting by transamination L-homoserine into 4-hydroxy-2-ketobutyrate. Also provided is a method for the production of derivatives of 4-hydroxy-2-ketobutyrate selected in the group consisting of 1,3-propanediol, 3-hydroxypropionaldehyde, 3-hydroxypropionate and 2,4-dihydroxybutyrate by culturing the genetically modified microorganism in a culture medium and recovering the desired derivative.

20 Claims, 3 Drawing Sheets

Figure 1:
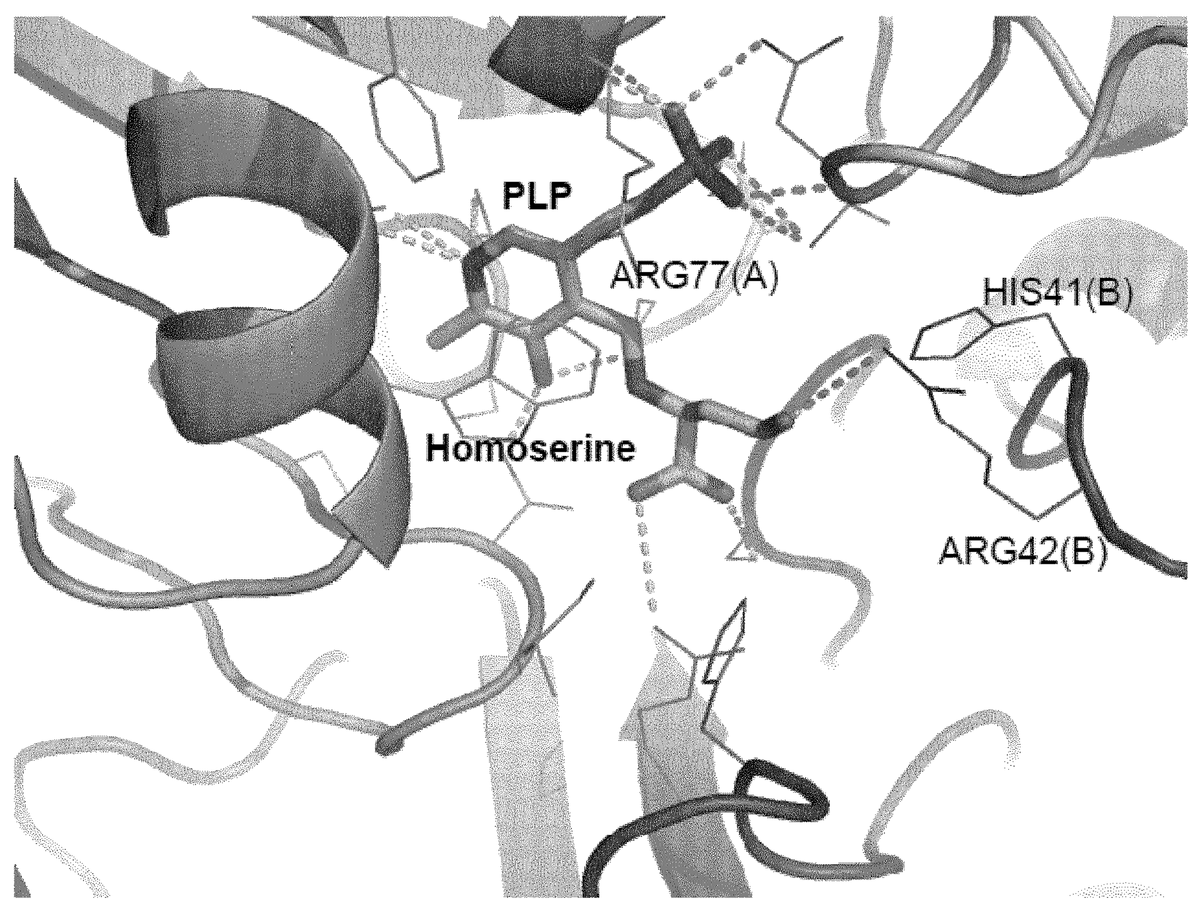

Specification includes a Sequence Listing.

(56) References Cited

OTHER PUBLICATIONS

Carrier et al, "Library of Synthetic 5' Secondary Structures To Manipulate mRNA Stability in *Escherichia coli*", Biotechnol. Prog., 1999 (published online Jan. 9, 1999), vol. 15, No. 1, pp. 56-64 (8 pages).
Case et al., "Amber 10 Users' Manual", University of California, San Francisco, 2008, pp. 1-304.
Datsenko et al., "One-step inactivation of chromosomal genes in *Escherichia coli* K-12 PCR products", PNAS, Jun. 6, 2000, vol. 97, No. 12, pp. 6640-6645 (6 pages).
English translation of the International Search Report (Form PCT/ISA/210 and PCT/ISA/220), dated Dec. 10, 2018, for International Applicaiton No. PCT/EP2018/077542.
Extended European Search Report, dated Dec. 5, 2017, for European Application No. 17306366.0.
Hester et al., "Crystal Structure of Phosphoserine Aminotransferase from *Escherichia coli* at 2.3 A Resolution: Comparison of the Unligated Enzyme and a Complex with α-Methyl-L-Glutamate", J.Mol. Biol., 1999, vol. 286, pp. 829-850 (22 pages).
Kollman et al., "Calculating Structures and Free Energies of Complex Molecules: Combining Molecular Mechanics and Continuum Models", Acc. Chem. Res., 2000, vol. 33, No. 12. pp. 889-897 (9 pages).
Reinscheid et al., "Analysis of a Corynebacterium glutamicum horn Gene Coding for a Feedback-Resistant Homoserine Dehydrogenase", Journal of Bacteriology, May 1991, vol. 173, No. 10, pp. 3228-3230 (3 pages).
Salis, "The Ribosome Binding Site Calculator", Methods of Enzymology, 2011, vol. 498, pp. 19-42 (24 pages).
Segal, "Enzyme kinetics", John Wiley & Sons, 1993, pp. 44-54 and 100-112 (13 pages).

* cited by examiner

```
Escherichia          -----------------------------------------------------------M
Citrobacter          -----------------------------------------------------------M
Enterobacter         -----------------------------------------------------------M
Pectobacterium       -----------------------------------------------------------M
Dickeya              -----------------------------------------------------------M
Pseudo_Putida        ----------------------------------------------------------MS
Pseudo_Aeruginosa    ----------------------------------------------------------MS
Pseudo_Fluorescens   ----------------------------------------------------------MS
Ralstonia            -----------------------------MGNTGSHFSIPRLMNDPQNPALAGMMQRALA
Arabidopsis          MAASTNSFLIGNQTQIPSLKPKSISQSFIHFTKPNTINLTTRTKSVSIRCASASTTVGSE
Clostridium          -----------------------------------------------------------M
Lactococcus          ------------------------------------------------------------
Bacillus             -----------------------------------------------------------M
Saccharomyces        -------------------------------------------------------MSLER

Escherichia          AQIFNFSSGPAMLPAEVLKQAQQELRDWNGLGTSVMEVSHRGKEFIQVAEEAEKDFRDLL
Citrobacter          AQVFNFSSGPAMLPAEVLKLAQQDLRDWHGLGTSVMEISHRGKEFIQVAEEAEQDFRDLL
Enterobacter         AQVFNFSSGPAMLPVDVLKQAQQELCDWQGLGTSVMEISHRGKEFIQVAEEAEKDFRDLL
Pectobacterium       TQIFNFSAGPAMLPVEVLRRAEQELCNWNGLGTSVMEISHRSKEFMQVAAESEQNLRDLL
Dickeya              TQVFNFSAGPAMLPVEVLRRAEQELCNWRGLGTSVMEISHRSKEFMQVASESEQDLRDLL
Pseudo_Putida        KRAFNFCAGPAALPDAVLQRAQAEMLDWRGKGLSVMEMSHRSDDYVAIAEKAEQDLRDLL
Pseudo_Aeruginosa    KRAFNFCAGPAALPDAVLQRAQAELLDWRGKGLSVMEMSHRSDDYVAIASKAEQDLRDLL
Pseudo_Fluorescens   KRAYNFCAGPAALPEAVLQRAQGELLDWHGKGLSVMEMSHRSDEFVSIATKAEQDLRDLL
Ralstonia            ERVYNFSPGPAALPAEVLQQAAEEMLSWHGTGVSVMEMSHRSREFESIHNEAIADLRELL
Arabidopsis          QRVINFAAGPAALPENVLLKAQSDLYNWRGSGMSVMEMSHRGKEFLSIIQKAESDLRQLL
Clostridium          SRVYNFSAGPAVLPESVLREAAGEMLDYKGTGMSVMEMSHRSKAFEEIITDAEKTLRELM
Lactococcus          -MIYNFGAGPSVLPKEVLKKVQEELLDFEKSGMSVMEISHRSKAFQKVIDEAENDLRDLM
Bacillus             ERTTNFNAGPAALPLEVLQKAQKEFIDFNESGMSVMELSHRSKEYEAVHQKAKSLLIELM
Saccharomyces        EEPQHFGAGPAQMPTPVLQQAAKDLINFNDIGLGIGEISHRSKDATKVIEDSKKHLIELL

Escherichia          NVPSNYKVLFCHGGGRGQFAAVPLNIL----GDK---TTADYVDAGYWAASAIKEAKKYC
Citrobacter          SIPSNYKVLFCHGGGRGQFAAIPLNIL----GDK---TSADYVDAGYWAASAIKEAKKYC
Enterobacter         NIPSNYKVLFCHGGGRGQFAGIPLNLL----GDK---TGADYVDAGYWAASAVKEAHKYC
Pectobacterium       KIPSNYKVLFCHGGARAQFAAVPLNLL----GER---STADYIDGGYWAHSAVNEAEKYC
Dickeya              KIPSNYKVLFCHGGARAQFAAVPLNLL----GEK---THADYIDGGYWAHSAVKEAEKYL
Pseudo_Putida        SVPSNYKVLFLQGGASQQFAEIPLNLL----PEN---GTADYIETGIWSKKAIEEARRFG
Pseudo_Aeruginosa    DIPSDYKVLFLQGGASQQFAEIPLNLL----PED---GVADYIDTGIWSKKAIEEARRYG
Pseudo_Fluorescens   GIPSHYKVLFLQGGASQQFAQIPLNLL----PED---GTADYIDTGIWGQKAIEEASRYG
Ralstonia            HIPANFKVLFLQGGAIGENAIVPLNLMRLRSAEQ---PKADFVVTGTWSVKTEQEARRYG
Arabidopsis          EIPSEYSVLFLQGGATTQFAALPLNLCKSD-------DSVDYIVTGSWGDKAFKEAKKYC
Clostridium          NIPDNYKVLFLQGGASQQFAMIPMNLMKN--------KVVDHIITGQWAKKAASEAKIFG
Lactococcus          SIPQNYKILFLQGGASSQFSMVPMNLAIG--------KKAYYNISGAFGEKAYDEAVKLS
Bacillus             GIPEDYDILFLQGGASLQFSMLPMNFLTP----E---KTAHFVMTGAWSEKALAETKLFG
Saccharomyces        NIPDTHEVFYLQGGGTTGFSSVATNLAAAYVGKHGKIAPAGYLVTGSWSQKSFEEAKRLH

Escherichia          TPN----VFDAKVTVDG--LRAVKPMREWQLSD---NAAYMHYCPNETIDG--IAIDETP
Citrobacter          SPN----VIDAKVTVDG--LRAVKPMSEWQLSD---NAAYVHYCPNETIDG--IAIDETP
Enterobacter         TPN----VIDAKVTVDG--LRAVKPMSEWQLSD---NAAYLHYCPNETIDG--IAIHEEP
Pectobacterium       TPN----VIDVKTRVDG--LRGVKPMREWQLSD---DAAFVHYCPNETIDG--IAIEEEP
Dickeya              TPT----VIDVKTRVDG--LRGVKPMSEWALSD---DAAYVHYCPNETIDG--LAIEEEP
Pseudo_Putida        NVN----VAATAKPYD---YLAIPGQNEWNLTK---NAAYVHYASNETIGG--LQFDWVP
Pseudo_Aeruginosa    TVN----VAASAKEYD---YFAIPGQNEWTLTK---DAAYVHYASNETIGG--LEFDWIP
Pseudo_Fluorescens   HVN----VAGTAKPYD---YFAIPGQNEWKLSK---DAAYVHYVANETIGG--LEFDWVP
Ralstonia            AVN----IAATSEAEK---FHRIPDIADWKLSD---DAGYVHLCTNETIVG--VEFQDIP
Arabidopsis          NPK----VIWSGKSEK---YTKVPTFDGLEQSS---DAKYLHICANETIHG--VEFKDYP
Clostridium          KVN----ILASSEDKT---FSYIPDLKDLKVSE---DADYVYICHNNTIYG--TTYKELP
Lactococcus          HFLDLMAISLGSTKKDN--YNHLLKIDKSKIDEK--NGAYLHLTTNNTIEGTSIFPENLP
Bacillus             NTS----ITATSETDN---YSYIPEVDLTDVKD----GAYLHITSNNTIFG--TQWQEFP
Saccharomyces        VPA---EVIFNAKDYNNGKFGKIPDESLWEDKIKGKAFSYVYLCENETVHG--VEWPELP
```

FIG. 2 A

```
Escherichia           DFGA---DVVVAADFSSTILSRPIDVSRYGVIYAGAQKNIGPAGLTIVIVREDLLGK-A-
Citrobacter           NFGS---DVVVAADFSSTILSAPLDVSRYGVIYAGAQKNIGPAGLTIVIVREDLLGK-A-
Enterobacter          NFGN---DVVVTADLSSTILSGPLDVSRYGVIYAGAQKNIGPAGLTLVIVREDLLGK-A-
Pectobacterium        DFG----DKIVVADYSSSILSRRIDVSRYGVIYAGAQKNIGPAGLTLVIVRDDLLGK-A-
Dickeya               DFG----DKIVVADYSSSILSRPLDVSRYGVIYAGAQKNVGPAGLTLVIVRDDLLGK-A-
Pseudo_Putida         QTG----DVPLVVDMSSDILSRPIDVSQFGLIYAGAQKNIGPSGLVVVIVREDLLGH-A-
Pseudo_Aeruginosa     ETG----DVPLVTDMSSDILSRPLDVSRFGLIYAGAQKNIGPSGLVVVIVREDLLGR-A-
Pseudo_Fluorescens    EVG----DVPLVCDMSSDILSRPIDVSKYGMIYAGAQKNIGPSGILVNIIREDLLGR-A-
Ralstonia             DIGQVKGDRVVVADASSHILSRPIDWSRVQVVYGGAQKNIGPAGVTIVIVRDDLIGH-A-
Arabidopsis           LVENP--DGVLIADMSSNFCSKPVDVSKFGVIYAGAQKNVGPSGVTIVIIRKDLIGN-A-
Clostridium           NVG----DKILVADMSSDFLSEPVDVSKYGLIFAGVQKNAGPAGVVVVIIREDLITEDV-
Lactococcus           EFA----SLPLVADMSSNILAVDYDVSKFGLIYAGAQKNLGIAGLTIVIIREDLLNE---
Bacillus              NSP-----IPLVADMSSDILSRKIDVSKFDVIYGGAQKNLGPSGVTVVIMKKSWLQN-E-
Saccharomyces         KCLVNDPNIEIVADLSSDILSRKIDVSQYGVIMAGAQKNIGLAGLTLYIIKKSILKNISG

Escherichia           ----------NIACPSILDYSILNDNGSMFNTPPTFAWYLSGLVFKWLKANGGVAEMDKI
Citrobacter           ----------NIACPSILDYTVLNDNDSMFNTPPTFAWYLSGLVFKWLKAQGGVAAMNKI
Enterobacter          ----------HKACPSILDYTVLNDNDSMFNTPPTFAWYLSGLVFKWLKKNGGVAQMDKI
Pectobacterium        ----------RRELPSILDYQILADNDSMFNTPPTFAWYLSGMVFKWLKEHGGLAEMEKR
Dickeya               ----------RRELPSILDYKILADNDSMFNTPPTFAWYLSGMVFKWLKEQGGLLEMEKR
Pseudo_Putida         ----------RSSCPTMLDYKVSADNGSMYNTPATYSWYLSGLVFEWLKEQGGVEAMEQR
Pseudo_Aeruginosa     ----------RSVCPTMLNYKIAADNGSMYNTPATYSWYLSGLVFEWLKEQGGVTAMEQR
Pseudo_Fluorescens    ----------RSLCPTMLNYKVAADNGSMYNTPPAFAWYLSGLVFEWLKEQGGVAAMGKL
Ralstonia             ----------HPLCPSAFNWRLVAEHNSMYNTPPTYAIYIAGLVFKWLKRQGGVPAIEQR
Arabidopsis           ----------RDITPVMLDYKIHDENSSLYNTPPCFGIYMCGLVFDDLLEQGGLKEVEKK
Clostridium           ----------LPGTPTMLRYKVHADNKSLYNTPPAYGIYICGKVFKWVKNKGGLEAMKKI
Lactococcus           ----------AESLSSMMDYQILVENGSMYNTPPTFAIYVAGLVFKWVKAQGGVKKLEEM
Bacillus              ----------NANVPKILKYSTHVKADSLYNTPPTFAIYMLSLVLEWLKENGGVEAVEQR
Saccharomyces         ASDETLHELGVPITPIAFDYPTVVKNNSAYNTIPIFTLHVMDLVFQHILKKGGVEAQQAE

Escherichia           NQQKAELLYGVIDNS-DFYRNDVAKAN-RSRMNVPFQLADSALDKLFLEESFAAGLHALK
Citrobacter           NQQKAELLYGVIDNS-DFYRNDVAKSN-RSRMNVPFQLADSALDKVFLEESFAAGLHALK
Enterobacter          NQQKAELLYSTIDGS-DFYRNDVAKAN-RSRMNVPFQLADSNLDKVFLEESFAAGLHALK
Pectobacterium        NQEKADLLYSAIDGN-DFYRNDVAVAN-RSRMNVPFLLADAALDKVFLEESVAAGLHALK
Dickeya               NQAKADLLYSAIDGS-DFYRNDVVPGS-RSRMNVPFQLADAALDPVFLQEAQAAGLHALK
Pseudo_Putida         NRAKKDRLYGFIDRS-EFYTNPISVNA-RSWMNVPFRLADERLDKAFLAGADARGLLNLK
Pseudo_Aeruginosa     NRAKKDLLYKTIDAS-DFYTNPIQPSA-RSWMNVPFRLADERLDKPFLEGAEARGLLNLK
Pseudo_Fluorescens    NEEKKRTLYDFIDAS-GLYSNPINLTD-RSWMNVPFRLADDRLDKPFLAGADERGLLNLK
Ralstonia             NIAKASALYNYLDQS-DFYRNEIHPSC-RSRMNVPFFLGDESRNEVFLQQARANGLVQLK
Arabidopsis           NQRKAELLYNAIDESRGFFRCPVEKSV-RSLMNVPFTLEKSELEAEFIKEAAKEKMVQLK
Clostridium           NEEKASILYDFLDSS-SMFKGTVVKKD-RSLMNVPFVTGSDELDAKFVKEAKAVGFENLK
Lactococcus           NQRKAQLLYDLIDQS-DFYQNPIKNKDERSICNVVFTSPSQELDELFTQKAEEKGFKSLK
Bacillus              NEQKAQVLYSCIDESNGFYKGHARKDS-RSRMNVTFTLRDDELTKTFVQKAKDAKMIGLG
Saccharomyces         NEEKAKILYEALDANSDFYNVPVDPKC-RSKMNVVFTLKKDGLDDQFLKEAAARHLTGLK

Escherichia           GHRVVGGMRASIYNAMPLEGVKALTDFMVEFERRHG
Citrobacter           GHRVVGGMRASIYNAMPLEGVKALTDFMVDFERRHG
Enterobacter          GHRVVGGMRASIYNAMPLEGVNTLTDFMVDFERRHG
Pectobacterium        GHRVVGGMRASIYNAMPLEGVKALTEFMADFARRHG
Dickeya               GHRVVGGMRASIYNAMPLSGVEALTEFMADFERRHG
Pseudo_Putida         GHRSVGGMRASIYNALGLEAVEALVGYMAEFEKEHG
Pseudo_Aeruginosa     GHRSVGGMRASIYNALGLDAVEALVAYMAEFEKEHG
Pseudo_Fluorescens    GHRSVGGMRASIYNAVDINAIKALIAYMAEFEKEHG
Ralstonia             GHKTVGGMRASIYNAMPLEGVMALVDFMREFERTSA
Arabidopsis           GHRSVGGMRASIYNAMPLAGVEKLVAFMKDFQARHA
Clostridium           GHRTVGGMRASIYNAMPIEGVKDLVEFMRKFEEDNK
Lactococcus           GHRSVGGMRASIYNAFPLEGVVELVKFMKEFEEGYK
Bacillus              GHRSVGGCRASIYNAVSLEDCEKLAAFMKKFQQENE
Saccharomyces         GHRSVGGFRASIYNALSVKAVQNLVDFIKEFAEKNA
```

FIG. 2 B

SEQUENCE LISTING

<160> NUMBER OF SEQ ID NOS: 55

<210> SEQ ID NO 1
<211> LENGTH: 1089
<212> TYPE: DNA
<213> ORGANISM: Escherichia coli

<400> SEQUENCE: 1

```
atggctcaaa tcttcaattt tagttctggt ccggcaatgc taccggcaga ggtgcttaaa     60

caggctcaac aggaactgcg cgactggaac ggtcttggta cgtcggtgat ggaagtgagt    120

caccgtggca aagagttcat tcaggttgca gaggaagccg agaaggattt tcgcgatctt    180

cttaatgtcc cctccaacta caaggtatta ttctgccatg gcggtggtcg cggtcagttt    240

gctgcggtac cgctgaatat tctcggtgat aaaaccaccg cagattatgt tgatgccggt    300

tactgggcgg caagtgccat taaagaagcg aaaaaatact gcacgcctaa tgtctttgac    360

gccaaagtga ctgttgatgg tctgcgcgcg gttaagccaa tgcgtgaatg gcaactctct    420

gataatgctg cttatatgca ttattgcccg aatgaaacca tcgatggtat cgccatcgac    480

gaaacgccag acttcggcgc agatgtggtg gtcgccgctg acttctcttc aaccattctt    540

tcccgtccga ttgacgtcag ccgttatggt gtaatttacg ctggcgcgca gaaaaatatc    600

ggcccggctg gcctgacaat cgtcatcgtt cgtgaagatt tgctgggcaa agcgaatatc    660

gcgtgtccgt cgattctgga ttattccatc ctcaacgata acggctccat gtttaacacg    720

ccgccgacat ttgcctggta tctatctggt ctggtcttta aatggctgaa agcgaacggc    780

ggtgtagctg aaatggataa aatcaatcag caaaaagcag aactgctata tggggtgatt    840

gataacagcg atttctaccg caatgacgtg gcgaaagcta accgttcgcg gatgaacgtg    900

ccgttccagt tggcggacag tgcgcttgac aaattgttcc ttgaagagtc ttttgctgct    960

ggccttcatg cactgaaagg tcaccgtgtg gtcggcggaa tgcgcgcttc tatttataac   1020

gccatgccgc tggaaggcgt taaagcgctg acagacttca tggttgagtt cgaacgccgt   1080

cacggttaa                                                           1089
```

<210> SEQ ID NO 2
<211> LENGTH: 362
<212> TYPE: PRT
<213> ORGANISM: Escherichia coli

<400> SEQUENCE: 2

```
Met Ala Gln Ile Phe Asn Phe Ser Ser Gly Pro Ala Met Leu Pro Ala
1               5                   10                  15

Glu Val Leu Lys Gln Ala Gln Gln Glu Leu Arg Asp Trp Asn Gly Leu
            20                  25                  30

Gly Thr Ser Val Met Glu Val Ser His Arg Gly Lys Glu Phe Ile Gln
        35                  40                  45

Val Ala Glu Glu Ala Glu Lys Asp Phe Arg Asp Leu Leu Asn Val Pro
    50                  55                  60

Ser Asn Tyr Lys Val Leu Phe Cys His Gly Gly Gly Arg Gly Gln Phe
65                  70                  75                  80

Ala Ala Val Pro Leu Asn Ile Leu Gly Asp Lys Thr Thr Ala Asp Tyr
                85                  90                  95

Val Asp Ala Gly Tyr Trp Ala Ala Ser Ala Ile Lys Glu Ala Lys Lys
            100                 105                 110

Tyr Cys Thr Pro Asn Val Phe Asp Ala Lys Val Thr Val Asp Gly Leu
        115                 120                 125
```

```
Arg Ala Val Lys Pro Met Arg Glu Trp Gln Leu Ser Asp Asn Ala Ala
    130                 135                 140

Tyr Met His Tyr Cys Pro Asn Glu Thr Ile Asp Gly Ile Ala Ile Asp
145                 150                 155                 160

Glu Thr Pro Asp Phe Gly Ala Asp Val Val Val Ala Ala Asp Phe Ser
                165                 170                 175

Ser Thr Ile Leu Ser Arg Pro Ile Asp Val Ser Arg Tyr Gly Val Ile
            180                 185                 190

Tyr Ala Gly Ala Gln Lys Asn Ile Gly Pro Ala Gly Leu Thr Ile Val
        195                 200                 205

Ile Val Arg Glu Asp Leu Leu Gly Lys Ala Asn Ile Ala Cys Pro Ser
    210                 215                 220

Ile Leu Asp Tyr Ser Ile Leu Asn Asp Asn Gly Ser Met Phe Asn Thr
225                 230                 235                 240

Pro Pro Thr Phe Ala Trp Tyr Leu Ser Gly Leu Val Phe Lys Trp Leu
                245                 250                 255

Lys Ala Asn Gly Gly Val Ala Glu Met Asp Lys Ile Asn Gln Gln Lys
            260                 265                 270

Ala Glu Leu Leu Tyr Gly Val Ile Asp Asn Ser Asp Phe Tyr Arg Asn
        275                 280                 285

Asp Val Ala Lys Ala Asn Arg Ser Arg Met Asn Val Pro Phe Gln Leu
    290                 295                 300

Ala Asp Ser Ala Leu Asp Lys Leu Phe Leu Glu Glu Ser Phe Ala Ala
305                 310                 315                 320

Gly Leu His Ala Leu Lys Gly His Arg Val Val Gly Gly Met Arg Ala
                325                 330                 335

Ser Ile Tyr Asn Ala Met Pro Leu Glu Gly Val Lys Ala Leu Thr Asp
            340                 345                 350

Phe Met Val Glu Phe Glu Arg Arg His Gly
        355                 360


<210> SEQ ID NO 3
<211> LENGTH: 370
<212> TYPE: PRT
<213> ORGANISM: Escherichia coli

<400> SEQUENCE: 3

Met Ala Gln Ile Phe Asn Phe Ser Ser Gly Pro Ala Met Leu Pro Ala
1               5                   10                  15

Glu Val Leu Lys Gln Ala Gln Gln Glu Leu Arg Asp Trp Asn Gly Leu
            20                  25                  30

Gly Thr Ser Val Met Glu Val Ser His Arg Gly Lys Glu Phe Ile Gln
        35                  40                  45

Val Ala Glu Glu Ala Glu Lys Asp Phe Arg Asp Leu Leu Asn Val Pro
    50                  55                  60

Ser Asn Tyr Lys Val Leu Phe Cys His Gly Gly Gly Arg Gly Gln Phe
65                  70                  75                  80

Ala Ala Val Pro Leu Asn Ile Leu Gly Asp Lys Thr Thr Ala Asp Tyr
                85                  90                  95

Val Asp Ala Gly Tyr Trp Ala Ala Ser Ala Ile Lys Glu Ala Lys Lys
            100                 105                 110

Tyr Cys Thr Pro Asn Val Phe Asp Ala Lys Val Thr Val Asp Gly Leu
        115                 120                 125

Arg Ala Val Lys Pro Met Arg Glu Trp Gln Leu Ser Asp Asn Ala Ala
```

```
    130                 135                 140

Tyr Met His Tyr Cys Pro Asn Glu Thr Ile Asp Gly Ile Ala Ile Asp
145                 150                 155                 160

Glu Thr Pro Asp Phe Gly Ala Asp Val Val Val Ala Ala Asp Phe Ser
                165                 170                 175

Ser Thr Ile Leu Ser Arg Pro Ile Asp Val Ser Arg Tyr Gly Val Ile
            180                 185                 190

Tyr Ala Gly Ala Gln Lys Asn Ile Gly Pro Ala Gly Leu Thr Ile Val
        195                 200                 205

Ile Val Arg Glu Asp Leu Leu Gly Lys Ala Asn Ile Ala Cys Pro Ser
    210                 215                 220

Ile Leu Asp Tyr Ser Ile Leu Asn Asp Asn Gly Ser Met Phe Asn Thr
225                 230                 235                 240

Pro Pro Thr Phe Ala Trp Tyr Leu Ser Gly Leu Val Phe Lys Trp Leu
                245                 250                 255

Lys Ala Asn Gly Gly Val Ala Glu Met Asp Lys Ile Asn Gln Gln Lys
            260                 265                 270

Ala Glu Leu Leu Tyr Gly Val Ile Asp Asn Ser Asp Phe Tyr Arg Asn
        275                 280                 285

Asp Val Ala Lys Ala Asn Arg Ser Arg Met Asn Val Pro Phe Gln Leu
    290                 295                 300

Ala Asp Ser Ala Leu Asp Lys Leu Phe Leu Glu Glu Ser Phe Ala Ala
305                 310                 315                 320

Gly Leu His Ala Leu Lys Gly His Arg Val Val Gly Gly Met Arg Ala
                325                 330                 335

Ser Ile Tyr Asn Ala Met Pro Leu Glu Gly Val Lys Ala Leu Thr Asp
            340                 345                 350

Phe Met Val Glu Phe Glu Arg Arg His Gly Leu Glu His His His His
        355                 360                 365

His His
    370


<210> SEQ ID NO 4
<211> LENGTH: 50
<212> TYPE: DNA
<213> ORGANISM: Artificial
<220> FEATURE:
<223> OTHER INFORMATION: part of oligonucleotide used for serC deletion,
      upstream region of serC gene

<400> SEQUENCE: 4

caatcgattg accgcgggtt aatagcaacg caacgtggtg aggggaaatg              50


<210> SEQ ID NO 5
<211> LENGTH: 50
<212> TYPE: DNA
<213> ORGANISM: Artificial
<220> FEATURE:
<223> OTHER INFORMATION: part of oligonucleotide used for serC deletion,
      downstream region of serC gene

<400> SEQUENCE: 5

ggctgtgggg attaagcaaa atttcggcat taaccgtgac ggcgttcgaa              50


<210> SEQ ID NO 6
<211> LENGTH: 1089
<212> TYPE: DNA
<213> ORGANISM: Escherichia coli
```

<400> SEQUENCE: 6

```
atggctcaaa tcttcaattt tagttctggt ccggcaatgc taccggcaga ggtgcttaaa      60
caggctcaac aggaactgcg cgactggaac ggtcttggta cgtcggtgat ggaagtgagt     120
cactggggca aagagttcat tcaggttgca gaggaagccg agaaggattt tcgcgatctt     180
cttaatgtcc cctccaacta caaggtatta ttctgccatg gcggtggtcg cggtcagttt     240
gctgcggtac cgctgaatat tctcggtgat aaaaccaccg cagattatgt tgatgccggt     300
tactgggcgg caagtgccat taaagaagcg aaaaaatact gcacgcctaa tgtctttgac     360
gccaaagtga ctgttgatgg tctgcgcgcg gttaagccaa tgcgtgaatg gcaactctct     420
gataatgctg cttatatgca ttattgcccg aatgaaacca tcgatggtat cgccatcgac     480
gaaacgccag acttcggcgc agatgtggtg gtcgccgctg acttctcttc aaccattctt     540
tcccgtccga ttgacgtcag ccgttatggt gtaatttacg ctggcgcgca gaaaaatatc     600
ggcccggctg gcctgacaat cgtcatcgtt cgtgaagatt tgctgggcaa agcgaatatc     660
gcgtgtccgt cgattctgga ttattccatc ctcaacgata acggctccat gtttaacacg     720
ccgccgacat ttgcctggta tctatctggt ctggtcttta aatggctgaa agcgaacggc     780
ggtgtagctg aaatggataa aatcaatcag caaaaagcag aactgctata tggggtgatt     840
gataacagcg atttctaccg caatgacgtg gcgaaagcta accgttcgcg gatgaacgtg     900
ccgttccagt tggcggacag tgcgcttgac aaattgttcc ttgaagagtc ttttgctgct     960
ggccttcatg cactgaaagg tcaccgtgtg gtcggcggaa tgcgcgcttc tatttataac    1020
gccatgccgc tggaaggcgt taaagcgctg acagacttca tggttgagtt cgaacgccgt    1080
cacggttaa                                                            1089
```

<210> SEQ ID NO 7
<211> LENGTH: 362
<212> TYPE: PRT
<213> ORGANISM: Escherichia coli

<400> SEQUENCE: 7

```
Met Ala Gln Ile Phe Asn Phe Ser Ser Gly Pro Ala Met Leu Pro Ala
1               5                   10                  15

Glu Val Leu Lys Gln Ala Gln Gln Glu Leu Arg Asp Trp Asn Gly Leu
            20                  25                  30

Gly Thr Ser Val Met Glu Val Ser His Trp Gly Lys Glu Phe Ile Gln
        35                  40                  45

Val Ala Glu Glu Ala Glu Lys Asp Phe Arg Asp Leu Leu Asn Val Pro
    50                  55                  60

Ser Asn Tyr Lys Val Leu Phe Cys His Gly Gly Gly Arg Gly Gln Phe
65                  70                  75                  80

Ala Ala Val Pro Leu Asn Ile Leu Gly Asp Lys Thr Thr Ala Asp Tyr
                85                  90                  95

Val Asp Ala Gly Tyr Trp Ala Ala Ser Ala Ile Lys Glu Ala Lys Lys
            100                 105                 110

Tyr Cys Thr Pro Asn Val Phe Asp Ala Lys Val Thr Val Asp Gly Leu
        115                 120                 125

Arg Ala Val Lys Pro Met Arg Glu Trp Gln Leu Ser Asp Asn Ala Ala
    130                 135                 140

Tyr Met His Tyr Cys Pro Asn Glu Thr Ile Asp Gly Ile Ala Ile Asp
145                 150                 155                 160

Glu Thr Pro Asp Phe Gly Ala Asp Val Val Val Ala Ala Asp Phe Ser
```

```
                165                 170                 175

Ser Thr Ile Leu Ser Arg Pro Ile Asp Val Ser Arg Tyr Gly Val Ile
            180                 185                 190

Tyr Ala Gly Ala Gln Lys Asn Ile Gly Pro Ala Gly Leu Thr Ile Val
        195                 200                 205

Ile Val Arg Glu Asp Leu Leu Gly Lys Ala Asn Ile Ala Cys Pro Ser
    210                 215                 220

Ile Leu Asp Tyr Ser Ile Leu Asn Asp Asn Gly Ser Met Phe Asn Thr
225                 230                 235                 240

Pro Pro Thr Phe Ala Trp Tyr Leu Ser Gly Leu Val Phe Lys Trp Leu
                245                 250                 255

Lys Ala Asn Gly Gly Val Ala Glu Met Asp Lys Ile Asn Gln Gln Lys
            260                 265                 270

Ala Glu Leu Leu Tyr Gly Val Ile Asp Asn Ser Asp Phe Tyr Arg Asn
        275                 280                 285

Asp Val Ala Lys Ala Asn Arg Ser Arg Met Asn Val Pro Phe Gln Leu
    290                 295                 300

Ala Asp Ser Ala Leu Asp Lys Leu Phe Leu Glu Glu Ser Phe Ala Ala
305                 310                 315                 320

Gly Leu His Ala Leu Lys Gly His Arg Val Val Gly Gly Met Arg Ala
                325                 330                 335

Ser Ile Tyr Asn Ala Met Pro Leu Glu Gly Val Lys Ala Leu Thr Asp
            340                 345                 350

Phe Met Val Glu Phe Glu Arg Arg His Gly
        355                 360


<210> SEQ ID NO 8
<211> LENGTH: 1089
<212> TYPE: DNA
<213> ORGANISM: Escherichia coli

<400> SEQUENCE: 8

atggctcaaa tcttcaattt tagttctggt ccggcaatgc taccggcaga ggtgcttaaa     60

caggctcaac aggaactgcg cgactggaac ggtcttggta cgtcggtgat ggaagtgagt    120

cactggggca aagagttcat tcaggttgca gaggaagccg agaaggattt tcgcgatctt    180

cttaatgtcc cctccaacta caaggtatta ttctgccatg gcggtggtac cggtcagttt    240

gctgcggtac cgctgaatat tctcggtgat aaaaccaccg cagattatgt tgatgccggt    300

tactgggcgg caagtgccat taaagaagcg aaaaaatact gcacgcctaa tgtctttgac    360

gccaaagtga ctgttgatgg tctgcgcgcg gttaagccaa tgcgtgaatg gcaactctct    420

gataatgctg cttatatgca ttattgcccg aatgaaacca tcgatggtat cgccatcgac    480

gaaacgccag acttcggcgc agatgtggtg gtcgccgctg acttctcttc aaccattctt    540

tcccgtccga ttgacgtcag ccgttatggt gtaatttacg ctggcgcgca gaaaaatatc    600

ggcccggctg gcctgacaat cgtcatcgtt cgtgaagatt tgctgggcaa agcgaatatc    660

gcgtgtccgt cgattctgga ttattccatc ctcaacgata acggctccat gtttaacacg    720

ccgccgacat ttgcctggta tctatctggt ctggtcttta aatggctgaa agcgaacggc    780

ggtgtagctg aaatggataa aatcaatcag caaaaagcag aactgctata tggggtgatt    840

gataacagcg atttctaccg caatgacgtg gcgaaagcta accgttcgcg gatgaacgtg    900

ccgttccagt tggcggacag tgcgcttgac aaattgttcc ttgaagagtc ttttgctgct    960

ggccttcatg cactgaaagg tcaccgtgtg gtcggcggaa tgcgcgcttc tatttataac   1020
```

```
gccatgccgc tggaaggcgt taaagcgctg acagacttca tggttgagtt cgaacgccgt   1080

cacggttaa                                                           1089


<210> SEQ ID NO 9
<211> LENGTH: 362
<212> TYPE: PRT
<213> ORGANISM: Escherichia coli

<400> SEQUENCE: 9

Met Ala Gln Ile Phe Asn Phe Ser Ser Gly Pro Ala Met Leu Pro Ala
1               5                   10                  15

Glu Val Leu Lys Gln Ala Gln Gln Glu Leu Arg Asp Trp Asn Gly Leu
            20                  25                  30

Gly Thr Ser Val Met Glu Val Ser His Trp Gly Lys Glu Phe Ile Gln
        35                  40                  45

Val Ala Glu Glu Ala Glu Lys Asp Phe Arg Asp Leu Leu Asn Val Pro
    50                  55                  60

Ser Asn Tyr Lys Val Leu Phe Cys His Gly Gly Gly Thr Gly Gln Phe
65                  70                  75                  80

Ala Ala Val Pro Leu Asn Ile Leu Gly Asp Lys Thr Thr Ala Asp Tyr
                85                  90                  95

Val Asp Ala Gly Tyr Trp Ala Ala Ser Ala Ile Lys Glu Ala Lys Lys
            100                 105                 110

Tyr Cys Thr Pro Asn Val Phe Asp Ala Lys Val Thr Val Asp Gly Leu
        115                 120                 125

Arg Ala Val Lys Pro Met Arg Glu Trp Gln Leu Ser Asp Asn Ala Ala
    130                 135                 140

Tyr Met His Tyr Cys Pro Asn Glu Thr Ile Asp Gly Ile Ala Ile Asp
145                 150                 155                 160

Glu Thr Pro Asp Phe Gly Ala Asp Val Val Val Ala Ala Asp Phe Ser
                165                 170                 175

Ser Thr Ile Leu Ser Arg Pro Ile Asp Val Ser Arg Tyr Gly Val Ile
            180                 185                 190

Tyr Ala Gly Ala Gln Lys Asn Ile Gly Pro Ala Gly Leu Thr Ile Val
        195                 200                 205

Ile Val Arg Glu Asp Leu Leu Gly Lys Ala Asn Ile Ala Cys Pro Ser
    210                 215                 220

Ile Leu Asp Tyr Ser Ile Leu Asn Asp Asn Gly Ser Met Phe Asn Thr
225                 230                 235                 240

Pro Pro Thr Phe Ala Trp Tyr Leu Ser Gly Leu Val Phe Lys Trp Leu
                245                 250                 255

Lys Ala Asn Gly Gly Val Ala Glu Met Asp Lys Ile Asn Gln Gln Lys
            260                 265                 270

Ala Glu Leu Leu Tyr Gly Val Ile Asp Asn Ser Asp Phe Tyr Arg Asn
        275                 280                 285

Asp Val Ala Lys Ala Asn Arg Ser Arg Met Asn Val Pro Phe Gln Leu
    290                 295                 300

Ala Asp Ser Ala Leu Asp Lys Leu Phe Leu Glu Glu Ser Phe Ala Ala
305                 310                 315                 320

Gly Leu His Ala Leu Lys Gly His Arg Val Val Gly Gly Met Arg Ala
                325                 330                 335

Ser Ile Tyr Asn Ala Met Pro Leu Glu Gly Val Lys Ala Leu Thr Asp
            340                 345                 350
```

```
Phe Met Val Glu Phe Glu Arg Arg His Gly
        355                 360


<210> SEQ ID NO 10
<211> LENGTH: 1089
<212> TYPE: DNA
<213> ORGANISM: Escherichia coli

<400> SEQUENCE: 10

atggctcaaa tcttcaattt tagttctggt ccggcaatgc taccggcaga ggtgcttaaa     60

caggctcaac aggaactgcg cgactggaac ggtcttggta cgtcggtgat ggaagtgagt    120

cactggggca aagagttcat tcaggttgca gaggaagccg agaaggattt tcgcgatctt    180

cttaatgtcc cctccaacta caaggtatta ttctgccatg gcggtggttg ggtcagttt    240

gctgcggtac cgctgaatat tctcggtgat aaaaccaccg cagattatgt tgatgccggt    300

tactgggcgg caagtgccat taaagaagcg aaaaaatact gcacgcctaa tgtctttgac    360

gccaaagtga ctgttgatgg tctgcgcgcg gttaagccaa tgcgtgaatg gcaactctct    420

gataatgctg cttatatgca ttattgcccg aatgaaacca tcgatggtat cgccatcgac    480

gaaacgccag acttcggcgc agatgtggtg gtcgccgctg acttctcttc aaccattctt    540

tcccgtccga ttgacgtcag ccgttatggt gtaatttacg ctggcgcgca gaaaaatatc    600

ggcccggctg gcctgacaat cgtcatcgtt cgtgaagatt tgctgggcaa agcgaatatc    660

gcgtgtccgt cgattctgga ttattccatc ctcaacgata acggctccat gtttaacacg    720

ccgccgacat ttgcctggta tctatctggt ctggtcttta aatggctgaa agcgaacggc    780

ggtgtagctg aaatggataa aatcaatcag caaaaagcag aactgctata tggggtgatt    840

gataacagcg atttctaccg caatgacgtg gcgaaagcta accgttcgcg gatgaacgtg    900

ccgttccagt tggcggacag tgcgcttgac aaattgttcc ttgaagagtc ttttgctgct    960

ggccttcatg cactgaaagg tcaccgtgtg gtcggcggaa tgcgcgcttc tatttataac   1020

gccatgccgc tggaaggcgt taaagcgctg acagacttca tggttgagtt cgaacgccgt   1080

cacggttaa                                                          1089


<210> SEQ ID NO 11
<211> LENGTH: 362
<212> TYPE: PRT
<213> ORGANISM: Escherichia coli

<400> SEQUENCE: 11

Met Ala Gln Ile Phe Asn Phe Ser Ser Gly Pro Ala Met Leu Pro Ala
1               5                   10                  15

Glu Val Leu Lys Gln Ala Gln Gln Glu Leu Arg Asp Trp Asn Gly Leu
            20                  25                  30

Gly Thr Ser Val Met Glu Val Ser His Trp Gly Lys Glu Phe Ile Gln
        35                  40                  45

Val Ala Glu Glu Ala Glu Lys Asp Phe Arg Asp Leu Leu Asn Val Pro
    50                  55                  60

Ser Asn Tyr Lys Val Leu Phe Cys His Gly Gly Gly Trp Gly Gln Phe
65                  70                  75                  80

Ala Ala Val Pro Leu Asn Ile Leu Gly Asp Lys Thr Thr Ala Asp Tyr
                85                  90                  95

Val Asp Ala Gly Tyr Trp Ala Ala Ser Ala Ile Lys Glu Ala Lys Lys
            100                 105                 110

Tyr Cys Thr Pro Asn Val Phe Asp Ala Lys Val Thr Val Asp Gly Leu
```

```
        115                 120                 125

Arg Ala Val Lys Pro Met Arg Glu Trp Gln Leu Ser Asp Asn Ala Ala
    130                 135                 140

Tyr Met His Tyr Cys Pro Asn Glu Thr Ile Asp Gly Ile Ala Ile Asp
145                 150                 155                 160

Glu Thr Pro Asp Phe Gly Ala Asp Val Val Val Ala Ala Asp Phe Ser
                165                 170                 175

Ser Thr Ile Leu Ser Arg Pro Ile Asp Val Ser Arg Tyr Gly Val Ile
            180                 185                 190

Tyr Ala Gly Ala Gln Lys Asn Ile Gly Pro Ala Gly Leu Thr Ile Val
        195                 200                 205

Ile Val Arg Glu Asp Leu Leu Gly Lys Ala Asn Ile Ala Cys Pro Ser
    210                 215                 220

Ile Leu Asp Tyr Ser Ile Leu Asn Asp Asn Gly Ser Met Phe Asn Thr
225                 230                 235                 240

Pro Pro Thr Phe Ala Trp Tyr Leu Ser Gly Leu Val Phe Lys Trp Leu
                245                 250                 255

Lys Ala Asn Gly Gly Val Ala Glu Met Asp Lys Ile Asn Gln Gln Lys
            260                 265                 270

Ala Glu Leu Leu Tyr Gly Val Ile Asp Asn Ser Asp Phe Tyr Arg Asn
        275                 280                 285

Asp Val Ala Lys Ala Asn Arg Ser Arg Met Asn Val Pro Phe Gln Leu
    290                 295                 300

Ala Asp Ser Ala Leu Asp Lys Leu Phe Leu Glu Glu Ser Phe Ala Ala
305                 310                 315                 320

Gly Leu His Ala Leu Lys Gly His Arg Val Val Gly Gly Met Arg Ala
                325                 330                 335

Ser Ile Tyr Asn Ala Met Pro Leu Glu Gly Val Lys Ala Leu Thr Asp
            340                 345                 350

Phe Met Val Glu Phe Glu Arg Arg His Gly
        355                 360


<210> SEQ ID NO 12
<211> LENGTH: 370
<212> TYPE: PRT
<213> ORGANISM: Escherichia coli

<400> SEQUENCE: 12

Met Ala Gln Ile Phe Asn Phe Ser Ser Gly Pro Ala Met Leu Pro Ala
1               5                   10                  15

Glu Val Leu Lys Gln Ala Gln Gln Glu Leu Arg Asp Trp Asn Gly Leu
            20                  25                  30

Gly Thr Ser Val Met Glu Val Ser His Trp Gly Lys Glu Phe Ile Gln
        35                  40                  45

Val Ala Glu Glu Ala Glu Lys Asp Phe Arg Asp Leu Leu Asn Val Pro
    50                  55                  60

Ser Asn Tyr Lys Val Leu Phe Cys His Gly Gly Gly Arg Gly Gln Phe
65                  70                  75                  80

Ala Ala Val Pro Leu Asn Ile Leu Gly Asp Lys Thr Thr Ala Asp Tyr
                85                  90                  95

Val Asp Ala Gly Tyr Trp Ala Ala Ser Ala Ile Lys Glu Ala Lys Lys
            100                 105                 110

Tyr Cys Thr Pro Asn Val Phe Asp Ala Lys Val Thr Val Asp Gly Leu
        115                 120                 125
```

```
Arg Ala Val Lys Pro Met Arg Glu Trp Gln Leu Ser Asp Asn Ala Ala
    130                 135                 140

Tyr Met His Tyr Cys Pro Asn Glu Thr Ile Asp Gly Ile Ala Ile Asp
145                 150                 155                 160

Glu Thr Pro Asp Phe Gly Ala Asp Val Val Val Ala Ala Asp Phe Ser
                165                 170                 175

Ser Thr Ile Leu Ser Arg Pro Ile Asp Val Ser Arg Tyr Gly Val Ile
            180                 185                 190

Tyr Ala Gly Ala Gln Lys Asn Ile Gly Pro Ala Gly Leu Thr Ile Val
        195                 200                 205

Ile Val Arg Glu Asp Leu Leu Gly Lys Ala Asn Ile Ala Cys Pro Ser
    210                 215                 220

Ile Leu Asp Tyr Ser Ile Leu Asn Asp Asn Gly Ser Met Phe Asn Thr
225                 230                 235                 240

Pro Pro Thr Phe Ala Trp Tyr Leu Ser Gly Leu Val Phe Lys Trp Leu
                245                 250                 255

Lys Ala Asn Gly Gly Val Ala Glu Met Asp Lys Ile Asn Gln Gln Lys
            260                 265                 270

Ala Glu Leu Leu Tyr Gly Val Ile Asp Asn Ser Asp Phe Tyr Arg Asn
        275                 280                 285

Asp Val Ala Lys Ala Asn Arg Ser Arg Met Asn Val Pro Phe Gln Leu
    290                 295                 300

Ala Asp Ser Ala Leu Asp Lys Leu Phe Leu Glu Glu Ser Phe Ala Ala
305                 310                 315                 320

Gly Leu His Ala Leu Lys Gly His Arg Val Val Gly Gly Met Arg Ala
                325                 330                 335

Ser Ile Tyr Asn Ala Met Pro Leu Glu Gly Val Lys Ala Leu Thr Asp
            340                 345                 350

Phe Met Val Glu Phe Glu Arg Arg His Gly Leu Glu His His His His
        355                 360                 365

His His
    370


<210> SEQ ID NO 13
<211> LENGTH: 370
<212> TYPE: PRT
<213> ORGANISM: Escherichia coli

<400> SEQUENCE: 13

Met Ala Gln Ile Phe Asn Phe Ser Ser Gly Pro Ala Met Leu Pro Ala
1               5                   10                  15

Glu Val Leu Lys Gln Ala Gln Gln Glu Leu Arg Asp Trp Asn Gly Leu
            20                  25                  30

Gly Thr Ser Val Met Glu Val Ser His Trp Gly Lys Glu Phe Ile Gln
        35                  40                  45

Val Ala Glu Glu Ala Glu Lys Asp Phe Arg Asp Leu Leu Asn Val Pro
    50                  55                  60

Ser Asn Tyr Lys Val Leu Phe Cys His Gly Gly Gly Thr Gly Gln Phe
65                  70                  75                  80

Ala Ala Val Pro Leu Asn Ile Leu Gly Asp Lys Thr Thr Ala Asp Tyr
                85                  90                  95

Val Asp Ala Gly Tyr Trp Ala Ala Ser Ala Ile Lys Glu Ala Lys Lys
            100                 105                 110

Tyr Cys Thr Pro Asn Val Phe Asp Ala Lys Val Thr Val Asp Gly Leu
        115                 120                 125
```

```
Arg Ala Val Lys Pro Met Arg Glu Trp Gln Leu Ser Asp Asn Ala Ala
    130                 135                 140

Tyr Met His Tyr Cys Pro Asn Glu Thr Ile Asp Gly Ile Ala Ile Asp
145                 150                 155                 160

Glu Thr Pro Asp Phe Gly Ala Asp Val Val Val Ala Ala Asp Phe Ser
                165                 170                 175

Ser Thr Ile Leu Ser Arg Pro Ile Asp Val Ser Arg Tyr Gly Val Ile
            180                 185                 190

Tyr Ala Gly Ala Gln Lys Asn Ile Gly Pro Ala Gly Leu Thr Ile Val
        195                 200                 205

Ile Val Arg Glu Asp Leu Leu Gly Lys Ala Asn Ile Ala Cys Pro Ser
    210                 215                 220

Ile Leu Asp Tyr Ser Ile Leu Asn Asp Asn Gly Ser Met Phe Asn Thr
225                 230                 235                 240

Pro Pro Thr Phe Ala Trp Tyr Leu Ser Gly Leu Val Phe Lys Trp Leu
                245                 250                 255

Lys Ala Asn Gly Gly Val Ala Glu Met Asp Lys Ile Asn Gln Gln Lys
            260                 265                 270

Ala Glu Leu Leu Tyr Gly Val Ile Asp Asn Ser Asp Phe Tyr Arg Asn
        275                 280                 285

Asp Val Ala Lys Ala Asn Arg Ser Arg Met Asn Val Pro Phe Gln Leu
    290                 295                 300

Ala Asp Ser Ala Leu Asp Lys Leu Phe Leu Glu Glu Ser Phe Ala Ala
305                 310                 315                 320

Gly Leu His Ala Leu Lys Gly His Arg Val Val Gly Gly Met Arg Ala
                325                 330                 335

Ser Ile Tyr Asn Ala Met Pro Leu Glu Gly Val Lys Ala Leu Thr Asp
            340                 345                 350

Phe Met Val Glu Phe Glu Arg Arg His Gly Leu Glu His His His His
        355                 360                 365

His His
    370


<210> SEQ ID NO 14
<211> LENGTH: 370
<212> TYPE: PRT
<213> ORGANISM: Escherichia coli

<400> SEQUENCE: 14

Met Ala Gln Ile Phe Asn Phe Ser Ser Gly Pro Ala Met Leu Pro Ala
1               5                   10                  15

Glu Val Leu Lys Gln Ala Gln Gln Glu Leu Arg Asp Trp Asn Gly Leu
            20                  25                  30

Gly Thr Ser Val Met Glu Val Ser His Trp Gly Lys Glu Phe Ile Gln
        35                  40                  45

Val Ala Glu Glu Ala Glu Lys Asp Phe Arg Asp Leu Leu Asn Val Pro
    50                  55                  60

Ser Asn Tyr Lys Val Leu Phe Cys His Gly Gly Gly Trp Gly Gln Phe
65                  70                  75                  80

Ala Ala Val Pro Leu Asn Ile Leu Gly Asp Lys Thr Thr Ala Asp Tyr
                85                  90                  95

Val Asp Ala Gly Tyr Trp Ala Ala Ser Ala Ile Lys Glu Ala Lys Lys
            100                 105                 110

Tyr Cys Thr Pro Asn Val Phe Asp Ala Lys Val Thr Val Asp Gly Leu
```

```
        115                 120                 125

Arg Ala Val Lys Pro Met Arg Glu Trp Gln Leu Ser Asp Asn Ala Ala
    130                 135                 140

Tyr Met His Tyr Cys Pro Asn Glu Thr Ile Asp Gly Ile Ala Ile Asp
145                 150                 155                 160

Glu Thr Pro Asp Phe Gly Ala Asp Val Val Val Ala Ala Asp Phe Ser
                165                 170                 175

Ser Thr Ile Leu Ser Arg Pro Ile Asp Val Ser Arg Tyr Gly Val Ile
            180                 185                 190

Tyr Ala Gly Ala Gln Lys Asn Ile Gly Pro Ala Gly Leu Thr Ile Val
        195                 200                 205

Ile Val Arg Glu Asp Leu Leu Gly Lys Ala Asn Ile Ala Cys Pro Ser
    210                 215                 220

Ile Leu Asp Tyr Ser Ile Leu Asn Asp Asn Gly Ser Met Phe Asn Thr
225                 230                 235                 240

Pro Pro Thr Phe Ala Trp Tyr Leu Ser Gly Leu Val Phe Lys Trp Leu
                245                 250                 255

Lys Ala Asn Gly Gly Val Ala Glu Met Asp Lys Ile Asn Gln Gln Lys
            260                 265                 270

Ala Glu Leu Leu Tyr Gly Val Ile Asp Asn Ser Asp Phe Tyr Arg Asn
        275                 280                 285

Asp Val Ala Lys Ala Asn Arg Ser Arg Met Asn Val Pro Phe Gln Leu
    290                 295                 300

Ala Asp Ser Ala Leu Asp Lys Leu Phe Leu Glu Glu Ser Phe Ala Ala
305                 310                 315                 320

Gly Leu His Ala Leu Lys Gly His Arg Val Val Gly Gly Met Arg Ala
                325                 330                 335

Ser Ile Tyr Asn Ala Met Pro Leu Glu Gly Val Lys Ala Leu Thr Asp
            340                 345                 350

Phe Met Val Glu Phe Glu Arg Arg His Gly Leu Glu His His His His
        355                 360                 365

His His
    370


<210> SEQ ID NO 15
<211> LENGTH: 1089
<212> TYPE: DNA
<213> ORGANISM: Citrobacter koseri (strain ATCC BAA895 / CDC 422583 /
      SGSC4696)

<400> SEQUENCE: 15

atggctcagg tcttcaattt tagttcaggt ccggcaatgc taccggcgga agtgcttaaa      60

ctggctcaac aggatctgcg tgactggcac ggtcttggca cgtcagtaat ggaaattagc     120

caccgtggca aagaatttat ccaggtcgca gaggaagcgg aacaggattt tcgcgatctc     180

ctcagcatcc cctccaacta caaagtattg ttctgccacg gcggcggccg tgggcagttt     240

gcggcaattc cgttaaatat tctgggcgat aaaacgtcgg cggattacgt tgatgccggt     300

tactgggcgg ccagcgccat caaagaagcg aaaaaatact gttcgccaaa cgtgattgac     360

gccaaagtca cggttgacgg tctgcgtgcg gtcaaaccga tgagcgagtg gcagctttct     420

gataacgccg cttacgttca ttattgcccg aacgaaacta tcgacggtat cgcaattgat     480

gaaacgccga attttggttc ggatgtcgtt gtggctgcgg atttctcatc cacaattctt     540

tccgcgccgc tggatgtgtc gcgttatggc gtgatctacg ccggggcgca gaaaaacatc     600
```

```
ggcccggcgg ggctgacaat tgtgatcgtg cgtgaagatc tgttaggtaa agcgaacatc    660

gcttgcccgt ctatccttga ttacaccgtg ctgaacgaca acgactctat gttcaatacc    720

ccgccgacct ttgcctggta tctttctggc ctggtgttca aatggctgaa agcgcagggc    780

ggcgttgcgg cgatgaacaa aatcaatcag caaaaagcgg aactgctgta tggcgtgatt    840

gataacagtg atttctaccg taacgatgtg gcgaaatcga atcgttcacg tatgaacgtg    900

cctttccagc tagcggacag cgcgcttgat aaagtcttcc tggaggaatc tttcgctgcg    960

ggtctgcatg cgctgaaagg tcatcgcgtg gtgggcggaa tgcgcgcctc tatctataac   1020

gcaatgccgc ttgaaggcgt gaaggcgttg acggatttca tggtcgattt cgagcgtcgc   1080

cacggctaa                                                           1089
```

```
<210> SEQ ID NO 16
<211> LENGTH: 362
<212> TYPE: PRT
<213> ORGANISM: Citrobacter koseri (strain ATCC BAA895 / CDC 422583 /
      SGSC4696)

<400> SEQUENCE: 16

Met Ala Gln Val Phe Asn Phe Ser Ser Gly Pro Ala Met Leu Pro Ala
1               5                   10                  15

Glu Val Leu Lys Leu Ala Gln Gln Asp Leu Arg Asp Trp His Gly Leu
            20                  25                  30

Gly Thr Ser Val Met Glu Ile Ser His Arg Gly Lys Glu Phe Ile Gln
        35                  40                  45

Val Ala Glu Glu Ala Glu Gln Asp Phe Arg Asp Leu Leu Ser Ile Pro
    50                  55                  60

Ser Asn Tyr Lys Val Leu Phe Cys His Gly Gly Gly Arg Gly Gln Phe
65                  70                  75                  80

Ala Ala Ile Pro Leu Asn Ile Leu Gly Asp Lys Thr Ser Ala Asp Tyr
                85                  90                  95

Val Asp Ala Gly Tyr Trp Ala Ala Ser Ala Ile Lys Glu Ala Lys Lys
            100                 105                 110

Tyr Cys Ser Pro Asn Val Ile Asp Ala Lys Val Thr Val Asp Gly Leu
        115                 120                 125

Arg Ala Val Lys Pro Met Ser Glu Trp Gln Leu Ser Asp Asn Ala Ala
    130                 135                 140

Tyr Val His Tyr Cys Pro Asn Glu Thr Ile Asp Gly Ile Ala Ile Asp
145                 150                 155                 160

Glu Thr Pro Asn Phe Gly Ser Asp Val Val Val Ala Ala Asp Phe Ser
                165                 170                 175

Ser Thr Ile Leu Ser Ala Pro Leu Asp Val Ser Arg Tyr Gly Val Ile
            180                 185                 190

Tyr Ala Gly Ala Gln Lys Asn Ile Gly Pro Ala Gly Leu Thr Ile Val
        195                 200                 205

Ile Val Arg Glu Asp Leu Leu Gly Lys Ala Asn Ile Ala Cys Pro Ser
    210                 215                 220

Ile Leu Asp Tyr Thr Val Leu Asn Asp Asn Asp Ser Met Phe Asn Thr
225                 230                 235                 240

Pro Pro Thr Phe Ala Trp Tyr Leu Ser Gly Leu Val Phe Lys Trp Leu
                245                 250                 255

Lys Ala Gln Gly Gly Val Ala Ala Met Asn Lys Ile Asn Gln Gln Lys
            260                 265                 270

Ala Glu Leu Leu Tyr Gly Val Ile Asp Asn Ser Asp Phe Tyr Arg Asn
```

```
        275                 280                 285

Asp Val Ala Lys Ser Asn Arg Ser Arg Met Asn Val Pro Phe Gln Leu
    290                 295                 300

Ala Asp Ser Ala Leu Asp Lys Val Phe Leu Glu Glu Ser Phe Ala Ala
305                 310                 315                 320

Gly Leu His Ala Leu Lys Gly His Arg Val Val Gly Gly Met Arg Ala
                325                 330                 335

Ser Ile Tyr Asn Ala Met Pro Leu Glu Gly Val Lys Ala Leu Thr Asp
            340                 345                 350

Phe Met Val Asp Phe Glu Arg Arg His Gly
        355                 360


<210> SEQ ID NO 17
<211> LENGTH: 1088
<212> TYPE: DNA
<213> ORGANISM: Enterobacter sp. (strain 638)

<400> SEQUENCE: 17

atggctcagg tcttcaattt cagttcaggt ccggcaatgt taccggtaga tgtacttaaa      60

caagcccagc aggagctttg cgactggcag ggccttggta catcggtgat ggaaattagc     120

caccgtggta aagaatttat ccaggtggcg gaagaggcag aaaaggattt tcgcgatctg     180

ctgaatattc cctcgaacta caaagtattg ttctgtcatg gcggcggtcg tggtcagttt     240

gcaggaattc cgttaaatct gctgggcgac aaaacgggcg cagattatgt cgatgccggt     300

tactgggctg ccagtgcggt caaagaagcg cataaatact gcacacccaa tgtgatcgat     360

gccaaagtaa cggttgatgg cttgcgcgca gttaaaccca tgagcgagtg gcagctttcc     420

gacaatgccg catatctgca ctattgcccg aatgaaacga tcgacggtat cgccattcat     480

gaagagccaa actttggcaa tgatgtggtg gtcactgcgg atctttcttc caccattctc     540

tccggtccgc tggacgtaag ccgctacggc gtcatctatg cgggtgcgca aaaaaacatt     600

ggtccggctg gcttgacgtt ggtaattgtg cgtgaagatc ttttaggtaa agcgcataag     660

gcgtgtcctt ccattctcga ctacaccgtg ctgaacgaca acgactcgat gttcaacacc     720

ccgccgacgt tcgcctggta tctttctggc cttgttttta aatggctcaa gaaaaacggt     780

ggcgtggcgc agatggacaa gatcaatcag caaaaagccg agctgcttta cagcacaatt     840

gatggcagtg atttctatcg taacgatgtc gcgaaagcca accgctcgcg catgaacgtg     900

ccgttccagc ttgcggacag caatctggat aaagtcttcc ttgaagagtc tttcgccgca     960

ggtttgcatg cgcttaaagg ccaccgcgtc gtgggcggca tgcgtgcttc tatctacaat    1020

gcaatgcctc ttgaaggcgt caaccgctga ccgattttat ggtcgacttc gaacgtcgcc    1080

acggttaa                                                             1088


<210> SEQ ID NO 18
<211> LENGTH: 362
<212> TYPE: PRT
<213> ORGANISM: Enterobacter sp. (strain 638)

<400> SEQUENCE: 18

Met Ala Gln Val Phe Asn Phe Ser Ser Gly Pro Ala Met Leu Pro Val
1               5                   10                  15

Asp Val Leu Lys Gln Ala Gln Gln Glu Leu Cys Asp Trp Gln Gly Leu
            20                  25                  30

Gly Thr Ser Val Met Glu Ile Ser His Arg Gly Lys Glu Phe Ile Gln
        35                  40                  45
```

```
Val Ala Glu Glu Ala Glu Lys Asp Phe Arg Asp Leu Leu Asn Ile Pro
    50                  55                  60

Ser Asn Tyr Lys Val Leu Phe Cys His Gly Gly Gly Arg Gly Gln Phe
65                  70                  75                  80

Ala Gly Ile Pro Leu Asn Leu Leu Gly Asp Lys Thr Gly Ala Asp Tyr
                85                  90                  95

Val Asp Ala Gly Tyr Trp Ala Ala Ser Ala Val Lys Glu Ala His Lys
            100                 105                 110

Tyr Cys Thr Pro Asn Val Ile Asp Ala Lys Val Thr Val Asp Gly Leu
        115                 120                 125

Arg Ala Val Lys Pro Met Ser Glu Trp Gln Leu Ser Asp Asn Ala Ala
    130                 135                 140

Tyr Leu His Tyr Cys Pro Asn Glu Thr Ile Asp Gly Ile Ala Ile His
145                 150                 155                 160

Glu Glu Pro Asn Phe Gly Asn Asp Val Val Val Thr Ala Asp Leu Ser
                165                 170                 175

Ser Thr Ile Leu Ser Gly Pro Leu Asp Val Ser Arg Tyr Gly Val Ile
            180                 185                 190

Tyr Ala Gly Ala Gln Lys Asn Ile Gly Pro Ala Gly Leu Thr Leu Val
        195                 200                 205

Ile Val Arg Glu Asp Leu Leu Gly Lys Ala His Lys Ala Cys Pro Ser
    210                 215                 220

Ile Leu Asp Tyr Thr Val Leu Asn Asp Asn Asp Ser Met Phe Asn Thr
225                 230                 235                 240

Pro Pro Thr Phe Ala Trp Tyr Leu Ser Gly Leu Val Phe Lys Trp Leu
                245                 250                 255

Lys Lys Asn Gly Gly Val Ala Gln Met Asp Lys Ile Asn Gln Gln Lys
            260                 265                 270

Ala Glu Leu Leu Tyr Ser Thr Ile Asp Gly Ser Asp Phe Tyr Arg Asn
        275                 280                 285

Asp Val Ala Lys Ala Asn Arg Ser Arg Met Asn Val Pro Phe Gln Leu
    290                 295                 300

Ala Asp Ser Asn Leu Asp Lys Val Phe Leu Glu Glu Ser Phe Ala Ala
305                 310                 315                 320

Gly Leu His Ala Leu Lys Gly His Arg Val Val Gly Gly Met Arg Ala
                325                 330                 335

Ser Ile Tyr Asn Ala Met Pro Leu Glu Gly Val Asn Thr Leu Thr Asp
            340                 345                 350

Phe Met Val Asp Phe Glu Arg Arg His Gly
        355                 360
```

<210> SEQ ID NO 19
<211> LENGTH: 1086
<212> TYPE: DNA
<213> ORGANISM: Pectobacterium carotovorum subsp. carotovorum (strain PC1)

<400> SEQUENCE: 19

```
atgactcaga tttttaattt tagcgccggt ccagcaatgc tgccggttga agtactgcgt      60

cgtgctgaac aggaattgtg taattggaat ggcctgggta catcggtcat ggaaatcagc     120

caccgtagta aagagtttat gcaggttgcc gctgaatccg aacaaaatct gcgtgatttg     180

ctgaaaatcc cctccaacta caaagtgctt ttttgccacg gtggtgctcg cgcacaattt     240

gcggcagtgc cattaaatct cttgggtgag cgctcaacgg cggactatat cgatggcgga     300
```

```
tactgggcgc acagtgcggt caatgaagca gaaaagtact gcacgcctaa tgtgattgac    360

gtgaaaacgc gcgtagacgg cctgcgtggc gttaagccga tgcgtgaatg gcaattgtct    420

gatgacgcgg catttgtgca ttactgcccg aatgaaacca ttgacggtat tgcgatcgaa    480

gaagagccgg attttggcga taaaattgtg gtcgccgact attcttccag catcctgtct    540

cgtcgtattg acgtcagccg ctacggtgtg atctacgccg gtgcacagaa aaatatcggt    600

cctgcgggtc tgacgttggt tatcgtacgt gacgatctgc tgggcaaagc gcgccgtgaa    660

ctaccatcga ttctggatta tcagattctg gcggacaatg actccatgtt taacacgccg    720

ccgacctttg cctggtatct gtccggtatg gtcttcaaat ggctgaaaga gcatggcggt    780

ctggctgaaa tggaaaaacg caaccaggag aaagccgacc tgctgtatag cgccattgac    840

ggtaatgatt tctatcgcaa tgacgtcgcg gtagcgaacc gttctcgcat gaacgtgccg    900

ttcctgctgg cagatgccgc gctcgataaa gtcttcctgg aagagtccgt tgcggcgggc    960

ttgcatgcgc tgaaaggcca tcgcgtagtg gggggcatgc gtgcgtcgat ctacaacgct   1020

atgccgttgg aaggcgtaaa agcgctgact gaatttatgg ctgacttcgc acgtcgccac   1080

ggttaa                                                              1086
```

```
<210> SEQ ID NO 20
<211> LENGTH: 361
<212> TYPE: PRT
<213> ORGANISM: Pectobacterium carotovorum subsp. carotovorum (strain
      PC1)

<400> SEQUENCE: 20

Met Thr Gln Ile Phe Asn Phe Ser Ala Gly Pro Ala Met Leu Pro Val
1               5                   10                  15

Glu Val Leu Arg Arg Ala Glu Gln Glu Leu Cys Asn Trp Asn Gly Leu
            20                  25                  30

Gly Thr Ser Val Met Glu Ile Ser His Arg Ser Lys Glu Phe Met Gln
        35                  40                  45

Val Ala Ala Glu Ser Glu Gln Asn Leu Arg Asp Leu Leu Lys Ile Pro
    50                  55                  60

Ser Asn Tyr Lys Val Leu Phe Cys His Gly Gly Ala Arg Ala Gln Phe
65                  70                  75                  80

Ala Ala Val Pro Leu Asn Leu Leu Gly Glu Arg Ser Thr Ala Asp Tyr
                85                  90                  95

Ile Asp Gly Gly Tyr Trp Ala His Ser Ala Val Asn Glu Ala Glu Lys
            100                 105                 110

Tyr Cys Thr Pro Asn Val Ile Asp Val Lys Thr Arg Val Asp Gly Leu
        115                 120                 125

Arg Gly Val Lys Pro Met Arg Glu Trp Gln Leu Ser Asp Asp Ala Ala
    130                 135                 140

Phe Val His Tyr Cys Pro Asn Glu Thr Ile Asp Gly Ile Ala Ile Glu
145                 150                 155                 160

Glu Glu Pro Asp Phe Gly Asp Lys Ile Val Val Ala Asp Tyr Ser Ser
                165                 170                 175

Ser Ile Leu Ser Arg Arg Ile Asp Val Ser Arg Tyr Gly Val Ile Tyr
            180                 185                 190

Ala Gly Ala Gln Lys Asn Ile Gly Pro Ala Gly Leu Thr Leu Val Ile
        195                 200                 205

Val Arg Asp Asp Leu Leu Gly Lys Ala Arg Arg Glu Leu Pro Ser Ile
    210                 215                 220
```

```
Leu Asp Tyr Gln Ile Leu Ala Asp Asn Asp Ser Met Phe Asn Thr Pro
225                 230                 235                 240

Pro Thr Phe Ala Trp Tyr Leu Ser Gly Met Val Phe Lys Trp Leu Lys
                245                 250                 255

Glu His Gly Gly Leu Ala Glu Met Glu Lys Arg Asn Gln Glu Lys Ala
            260                 265                 270

Asp Leu Leu Tyr Ser Ala Ile Asp Gly Asn Asp Phe Tyr Arg Asn Asp
        275                 280                 285

Val Ala Val Ala Asn Arg Ser Arg Met Asn Val Pro Phe Leu Leu Ala
    290                 295                 300

Asp Ala Ala Leu Asp Lys Val Phe Leu Glu Glu Ser Val Ala Ala Gly
305                 310                 315                 320

Leu His Ala Leu Lys Gly His Arg Val Val Gly Gly Met Arg Ala Ser
                325                 330                 335

Ile Tyr Asn Ala Met Pro Leu Glu Gly Val Lys Ala Leu Thr Glu Phe
            340                 345                 350

Met Ala Asp Phe Ala Arg Arg His Gly
        355                 360


<210> SEQ ID NO 21
<211> LENGTH: 1086
<212> TYPE: DNA
<213> ORGANISM: Dickeya zeae (strain Ech586) (Dickeya dadantii (strain
      Ech586))

<400> SEQUENCE: 21

atgactcagg tttttaattt tagtgctggt ccggccatgt taccggtaga agtattacgt     60

cgagcagaac aagaactgtg caactggcgc ggtttgggta cctcggtgat ggagatcagc    120

caccgcagca aagaattcat gcaggtggcc agcgaatctg aacaggattt gcgtgatttg    180

ctgaaaatcc cctcgaatta caaggtcttg ttctgtcatg gtggtgcccg tgcccagttt    240

gcggcggttc cgctcaacct gctgggagag aaaacccacg cggattatat tgatggcggg    300

tactgggcgc acagcgcggt taaagaagct gagaaatatc tcacaccgac cgttattgac    360

gtgaaaaccc gcgttgatgg tctgcgcggt gttaaaccga tgagcgaatg ggcgctgtcg    420

gatgatgccg cttacgtgca ctactgcccg aatgaaacta tcgacggtct ggccatcgaa    480

gaagagccgg attttggcga taaaattgtg gtggcggact actcttccag tattttgtcg    540

cgtccgctgg atgtgagccg ttacggcgtc atttatgctg gtgcacagaa aaacgtaggg    600

ccagctggcc tgacgctggt tattgtgcgg gatgacctgc tcggcaaggc tcgccgtgaa    660

ttgccgtcga ttctggatta caaaattctg gctgataacg actccatgtt taacacgccg    720

ccgacatttg cctggtatct atccggcatg gtgttcaagt ggctgaaaga gcagggtggc    780

cttttggaga tggaaaaacg caatcaggcg aaggccgatc tgctgtattc cgccattgat    840

ggcagcgatt tttatcgtaa tgatgttgtc ccgggcagcc gttcgcgtat gaacgtgcca    900

tttcagttgg ccgatgccgc gttggatccg gtattcctgc aggaagctca ggctgccggg    960

ttgcatgcgc tgaaaggcca tcgtgttgtg ggcggtatgc gtgcatctat ctacaatgct   1020

atgccgctga gtggtgtaga agcactgacg gagttcatgg cagacttcga gcgccgtcac   1080

ggctga                                                               1086


<210> SEQ ID NO 22
<211> LENGTH: 361
<212> TYPE: PRT
```

<213> ORGANISM: Dickeya zeae (strain Ech586) (Dickeya dadantii (strain Ech586))

<400> SEQUENCE: 22

```
Met Thr Gln Val Phe Asn Phe Ser Ala Gly Pro Ala Met Leu Pro Val
1               5                   10                  15

Glu Val Leu Arg Arg Ala Glu Gln Glu Leu Cys Asn Trp Arg Gly Leu
            20                  25                  30

Gly Thr Ser Val Met Glu Ile Ser His Arg Ser Lys Glu Phe Met Gln
        35                  40                  45

Val Ala Ser Glu Ser Glu Gln Asp Leu Arg Asp Leu Leu Lys Ile Pro
    50                  55                  60

Ser Asn Tyr Lys Val Leu Phe Cys His Gly Gly Ala Arg Ala Gln Phe
65                  70                  75                  80

Ala Ala Val Pro Leu Asn Leu Leu Gly Glu Lys Thr His Ala Asp Tyr
                85                  90                  95

Ile Asp Gly Gly Tyr Trp Ala His Ser Ala Val Lys Glu Ala Glu Lys
            100                 105                 110

Tyr Leu Thr Pro Thr Val Ile Asp Val Lys Thr Arg Val Asp Gly Leu
        115                 120                 125

Arg Gly Val Lys Pro Met Ser Glu Trp Ala Leu Ser Asp Asp Ala Ala
    130                 135                 140

Tyr Val His Tyr Cys Pro Asn Glu Thr Ile Asp Gly Leu Ala Ile Glu
145                 150                 155                 160

Glu Glu Pro Asp Phe Gly Asp Lys Ile Val Val Ala Asp Tyr Ser Ser
                165                 170                 175

Ser Ile Leu Ser Arg Pro Leu Asp Val Ser Arg Tyr Gly Val Ile Tyr
            180                 185                 190

Ala Gly Ala Gln Lys Asn Val Gly Pro Ala Gly Leu Thr Leu Val Ile
        195                 200                 205

Val Arg Asp Asp Leu Leu Gly Lys Ala Arg Arg Glu Leu Pro Ser Ile
    210                 215                 220

Leu Asp Tyr Lys Ile Leu Ala Asp Asn Asp Ser Met Phe Asn Thr Pro
225                 230                 235                 240

Pro Thr Phe Ala Trp Tyr Leu Ser Gly Met Val Phe Lys Trp Leu Lys
                245                 250                 255

Glu Gln Gly Gly Leu Leu Glu Met Glu Lys Arg Asn Gln Ala Lys Ala
            260                 265                 270

Asp Leu Leu Tyr Ser Ala Ile Asp Gly Ser Asp Phe Tyr Arg Asn Asp
        275                 280                 285

Val Val Pro Gly Ser Arg Ser Arg Met Asn Val Pro Phe Gln Leu Ala
    290                 295                 300

Asp Ala Ala Leu Asp Pro Val Phe Leu Gln Glu Ala Gln Ala Ala Gly
305                 310                 315                 320

Leu His Ala Leu Lys Gly His Arg Val Val Gly Gly Met Arg Ala Ser
                325                 330                 335

Ile Tyr Asn Ala Met Pro Leu Ser Gly Val Glu Ala Leu Thr Glu Phe
            340                 345                 350

Met Ala Asp Phe Glu Arg Arg His Gly
        355                 360
```

<210> SEQ ID NO 23
<211> LENGTH: 1086
<212> TYPE: DNA
<213> ORGANISM: Pseudomonas putida (strain ATCC 47054 / DSM 6125 / NCIMB

11950 / KT2440)

<400> SEQUENCE: 23

```
gtgagcaaac gagcctttaa cttctgcgca ggccctgccg cgcttcctga cgctgtcctg      60
cagcgcgcac aggccgagat gctggactgg cgtggcaagg ggttgtcggt gatggaaatg     120
agccatcgca gcgacgatta cgtggccatc gccgaaaagg ccgagcagga cctgcgtgac     180
ctgctgtccg tcccctccaa ctacaaggtg ctgttcctgc aaggcggcgc cagccagcag     240
ttcgctgaaa tcccgctgaa cctgctgccg gaaaacggca cggccgacta catcgaaacc     300
ggcatctggt cgaaaaaggc catcgaggaa gcgcgccgtt tcggcaacgt caacgtcgcc     360
gccactgcca agccttacga ctacctggcc atccccggcc agaacgagtg gaacctgacc     420
aaaaacgcag cctacgtgca ctatgcgtcc aacgagacca tcggtggcct gcagtttgac     480
tgggtgccgc aaaccggtga cgtgccgctg gtggtcgata tgtcgtccga catcctctcg     540
cgcccgatcg atgtgtcgca gttcggcctg atctacgccg gcgcgcagaa gaatatcggc     600
ccaagcggcc tggtggtggt gatcgtgcgc gaagacctgt tgggccatgc ccgcagcagc     660
tgcccgacca tgctcgacta caaggtttcg gctgacaacg gctcgatgta caacaccccg     720
gccacctact cctggtacct ctctggcctg gtcttcgagt ggctgaaaga gcagggcggt     780
gtcgaggcca tggagcagcg caaccgtgcc aagaaagacc gcctttacgg cttcatcgac     840
cgcagcgagt tctacaccaa cccgatcagc gtcaacgccc gttcgtggat gaacgtgccg     900
ttccgcctgg ctgacgagcg cctggacaag gccttcctcg ctggcgccga cgcgcgtggc     960
ctgctcaacc tcaagggcca ccgttcggtt ggcggcatgc gcgcctccat ctacaacgcc    1020
ctgggcctgg aagcggtaga agcgctggta ggctacatgg ctgaattcga gaaggagcat    1080
ggctga                                                               1086
```

<210> SEQ ID NO 24
<211> LENGTH: 361
<212> TYPE: PRT
<213> ORGANISM: Pseudomonas putida (strain ATCC 47054 / DSM 6125 / NCIMB 11950 / KT2440)

<400> SEQUENCE: 24

```
Met Ser Lys Arg Ala Phe Asn Phe Cys Ala Gly Pro Ala Ala Leu Pro
1               5                   10                  15

Asp Ala Val Leu Gln Arg Ala Gln Ala Glu Met Leu Asp Trp Arg Gly
            20                  25                  30

Lys Gly Leu Ser Val Met Glu Met Ser His Arg Ser Asp Asp Tyr Val
        35                  40                  45

Ala Ile Ala Glu Lys Ala Glu Gln Asp Leu Arg Asp Leu Leu Ser Val
    50                  55                  60

Pro Ser Asn Tyr Lys Val Leu Phe Leu Gln Gly Gly Ala Ser Gln Gln
65                  70                  75                  80

Phe Ala Glu Ile Pro Leu Asn Leu Leu Pro Glu Asn Gly Thr Ala Asp
                85                  90                  95

Tyr Ile Glu Thr Gly Ile Trp Ser Lys Lys Ala Ile Glu Glu Ala Arg
            100                 105                 110

Arg Phe Gly Asn Val Asn Val Ala Ala Thr Ala Lys Pro Tyr Asp Tyr
        115                 120                 125

Leu Ala Ile Pro Gly Gln Asn Glu Trp Asn Leu Thr Lys Asn Ala Ala
    130                 135                 140

Tyr Val His Tyr Ala Ser Asn Glu Thr Ile Gly Gly Leu Gln Phe Asp
```

```
145                 150                 155                 160

Trp Val Pro Gln Thr Gly Asp Val Pro Leu Val Val Asp Met Ser Ser
                165                 170                 175

Asp Ile Leu Ser Arg Pro Ile Asp Val Ser Gln Phe Gly Leu Ile Tyr
            180                 185                 190

Ala Gly Ala Gln Lys Asn Ile Gly Pro Ser Gly Leu Val Val Val Ile
        195                 200                 205

Val Arg Glu Asp Leu Leu Gly His Ala Arg Ser Ser Cys Pro Thr Met
    210                 215                 220

Leu Asp Tyr Lys Val Ser Ala Asp Asn Gly Ser Met Tyr Asn Thr Pro
225                 230                 235                 240

Ala Thr Tyr Ser Trp Tyr Leu Ser Gly Leu Val Phe Glu Trp Leu Lys
                245                 250                 255

Glu Gln Gly Gly Val Glu Ala Met Glu Gln Arg Asn Arg Ala Lys Lys
            260                 265                 270

Asp Arg Leu Tyr Gly Phe Ile Asp Arg Ser Glu Phe Tyr Thr Asn Pro
        275                 280                 285

Ile Ser Val Asn Ala Arg Ser Trp Met Asn Val Pro Phe Arg Leu Ala
    290                 295                 300

Asp Glu Arg Leu Asp Lys Ala Phe Leu Ala Gly Ala Asp Ala Arg Gly
305                 310                 315                 320

Leu Leu Asn Leu Lys Gly His Arg Ser Val Gly Gly Met Arg Ala Ser
                325                 330                 335

Ile Tyr Asn Ala Leu Gly Leu Glu Ala Val Glu Ala Leu Val Gly Tyr
            340                 345                 350

Met Ala Glu Phe Glu Lys Glu His Gly
        355                 360
```

<210> SEQ ID NO 25
<211> LENGTH: 1086
<212> TYPE: DNA
<213> ORGANISM: Pseudomonas fluorescens (strain SBW25)

<400> SEQUENCE: 25

```
gtgagcaaga gagcctataa cttctgtgcc ggtcccgcgg cgcttcctga agcagtcctg     60

cagcgtgcgc agggtgaact cctcgactgg catggaaaag gcctctccgt gatggaaatg    120

agccatcgca gcgatgagtt cgtgtccatt gccaccaagg ccgagcagga tctgcgcgac    180

ttgctgggca tcccctccca ttacaaagtg ctgttcctgc agggcggcgc gagccagcag    240

ttcgcccaga tcccgctgaa cctgctgccg gaagacggca ctgccgacta catcgacacc    300

ggtatctggg gtcagaaagc cattgaagag gcctcccgct acggtcacgt caatgtggcg    360

ggcaccgcca agccttacga ttactttgcc attcccggcc agaacgagtg gaagctgtcg    420

aaggacgccg cctacgtgca ttacgtagcg aacgaaacca tcggcggcct ggaattcgac    480

tgggtaccgg aagtcggcga cgttccgctg gtgtgcgaca tgtcttctga catcctttcg    540

cgcccgatcg atgtgtccaa gtacggcatg atctacgcgg gtgcgcagaa gaacatcggc    600

ccgagcggca tcctggtcaa catcatccgc gaagacctgc tggggcgtgc ccgttcgctg    660

tgcccgacca tgctcaacta caaggtcgcg gccgataacg gctcgatgta caacaccccg    720

ccggcgttcg cctggtacct gtccggcctg gtcttcgagt ggctgaaaga gcagggcggt    780

gtcgccgcca tgggcaagct caacgaagag aagaagcgca ccctgtacga cttcatcgac    840

gccagcggcc tgtacagcaa cccgatcaac ctgaccgacc gctcgtggat gaacgtgccg    900
```

```
ttccgcctgg ctgacgatcg cctggacaag ccattcctgg ccggtgccga cgagcgcggc    960

ctgctgaacc tcaagggcca ccgttcggtc ggtggcatgc gcgcctccat ctacaacgct   1020

gtcgacatca atgccatcaa ggcgctgatt gcctacatgg cagagttcga aaaggaacac   1080

ggctaa                                                              1086


<210> SEQ ID NO 26
<211> LENGTH: 361
<212> TYPE: PRT
<213> ORGANISM: Pseudomonas fluorescens (strain SBW25)

<400> SEQUENCE: 26

Met Ser Lys Arg Ala Tyr Asn Phe Cys Ala Gly Pro Ala Ala Leu Pro
1               5                   10                  15

Glu Ala Val Leu Gln Arg Ala Gln Gly Glu Leu Leu Asp Trp His Gly
            20                  25                  30

Lys Gly Leu Ser Val Met Glu Met Ser His Arg Ser Asp Glu Phe Val
        35                  40                  45

Ser Ile Ala Thr Lys Ala Glu Gln Asp Leu Arg Asp Leu Leu Gly Ile
    50                  55                  60

Pro Ser His Tyr Lys Val Leu Phe Leu Gln Gly Gly Ala Ser Gln Gln
65                  70                  75                  80

Phe Ala Gln Ile Pro Leu Asn Leu Leu Pro Glu Asp Gly Thr Ala Asp
                85                  90                  95

Tyr Ile Asp Thr Gly Ile Trp Gly Gln Lys Ala Ile Glu Glu Ala Ser
            100                 105                 110

Arg Tyr Gly His Val Asn Val Ala Gly Thr Ala Lys Pro Tyr Asp Tyr
        115                 120                 125

Phe Ala Ile Pro Gly Gln Asn Glu Trp Lys Leu Ser Lys Asp Ala Ala
    130                 135                 140

Tyr Val His Tyr Val Ala Asn Glu Thr Ile Gly Gly Leu Glu Phe Asp
145                 150                 155                 160

Trp Val Pro Glu Val Gly Asp Val Pro Leu Val Cys Asp Met Ser Ser
                165                 170                 175

Asp Ile Leu Ser Arg Pro Ile Asp Val Ser Lys Tyr Gly Met Ile Tyr
            180                 185                 190

Ala Gly Ala Gln Lys Asn Ile Gly Pro Ser Gly Ile Leu Val Asn Ile
        195                 200                 205

Ile Arg Glu Asp Leu Leu Gly Arg Ala Arg Ser Leu Cys Pro Thr Met
    210                 215                 220

Leu Asn Tyr Lys Val Ala Ala Asp Asn Gly Ser Met Tyr Asn Thr Pro
225                 230                 235                 240

Pro Ala Phe Ala Trp Tyr Leu Ser Gly Leu Val Phe Glu Trp Leu Lys
                245                 250                 255

Glu Gln Gly Gly Val Ala Ala Met Gly Lys Leu Asn Glu Glu Lys Lys
            260                 265                 270

Arg Thr Leu Tyr Asp Phe Ile Asp Ala Ser Gly Leu Tyr Ser Asn Pro
        275                 280                 285

Ile Asn Leu Thr Asp Arg Ser Trp Met Asn Val Pro Phe Arg Leu Ala
    290                 295                 300

Asp Asp Arg Leu Asp Lys Pro Phe Leu Ala Gly Ala Asp Glu Arg Gly
305                 310                 315                 320

Leu Leu Asn Leu Lys Gly His Arg Ser Val Gly Gly Met Arg Ala Ser
                325                 330                 335
```

```
Ile Tyr Asn Ala Val Asp Ile Asn Ala Ile Lys Ala Leu Ile Ala Tyr
            340                 345                 350

Met Ala Glu Phe Glu Lys Glu His Gly
        355                 360


<210> SEQ ID NO 27
<211> LENGTH: 1086
<212> TYPE: DNA
<213> ORGANISM: Pseudomonas aeruginosa (strain UCBPPPA14)

<400> SEQUENCE: 27

gtgagcaagc gagccttcaa tttctgcgcc ggtcccgcgg cgcttcccga cgcagttctg      60

caacgtgccc aggccgagct tctcgactgg cggggcaagg gcctttcggt catggaaatg     120

agccaccgta gcgacgacta cgtggccatc gccagcaagg ccgagcagga cctgcgcgac     180

ctgctcgaca ttccctcgga ctacaaggtg ctgttcctgc agggcggcgc cagccagcag     240

ttcgccgaga ttccgctgaa cctgctgccc gaagatggcg tcgccgacta tatcgatacc     300

ggtatctggt cgaagaaggc catcgaggag gctcgtcgct atggcaccgt gaatgtcgcg     360

gccagcgcca aggagtacga ctacttcgcc attccgggtc agaacgagtg gacgctgacc     420

aaggacgcgg cctatgtgca ctacgcctcc aacgagacca tcggcggcct cgagttcgac     480

tggattcccg agaccggcga cgtgccgctg gtcaccgaca tgtcctccga tatcctctcg     540

cgcccgctcg acgtgtcccg cttcggcctg atctatgccg ggcgcagaa  gaacatcggc     600

ccgtccggcc tggtggtggt gatcgttcgc gaagacctgc tcggccgcgc ccgcagcgtc     660

tgcccgacca tgctcaacta caagatcgcc gcggacaacg gttccatgta caacaccccg     720

gcgacctact cctggtacct gtccggcttg gtcttcgaat ggctgaagga gcagggcggg     780

gtgaccgcga tggagcagcg caaccgcgcc aagaaggacc tgctgtacaa gaccatcgat     840

gccagcgact tctacaccaa cccgatccag ccgagcgccc gctcctggat gaacgtgccg     900

ttccgcctgg ccgacgagcg tctcgacaag ccgttcctgg aaggcgccga ggcgcgcggg     960

ctgctcaacc tgaaaggcca ccgctcggtc ggcggcatgc gcgcttccat ctacaacgcc    1020

cttggcctgg acgcggtcga ggcgctggtc gcatacatgg cggagttcga gaaggagcac    1080

ggctga                                                               1086


<210> SEQ ID NO 28
<211> LENGTH: 361
<212> TYPE: PRT
<213> ORGANISM: Pseudomonas aeruginosa (strain UCBPPPA14)

<400> SEQUENCE: 28

Met Ser Lys Arg Ala Phe Asn Phe Cys Ala Gly Pro Ala Ala Leu Pro
1               5                   10                  15

Asp Ala Val Leu Gln Arg Ala Gln Ala Glu Leu Leu Asp Trp Arg Gly
            20                  25                  30

Lys Gly Leu Ser Val Met Glu Met Ser His Arg Ser Asp Asp Tyr Val
        35                  40                  45

Ala Ile Ala Ser Lys Ala Glu Gln Asp Leu Arg Asp Leu Leu Asp Ile
    50                  55                  60

Pro Ser Asp Tyr Lys Val Leu Phe Leu Gln Gly Gly Ala Ser Gln Gln
65                  70                  75                  80

Phe Ala Glu Ile Pro Leu Asn Leu Leu Pro Glu Asp Gly Val Ala Asp
                85                  90                  95

Tyr Ile Asp Thr Gly Ile Trp Ser Lys Lys Ala Ile Glu Glu Ala Arg
```

```
        100                 105                 110

Arg Tyr Gly Thr Val Asn Val Ala Ala Ser Ala Lys Glu Tyr Asp Tyr
    115                 120                 125

Phe Ala Ile Pro Gly Gln Asn Glu Trp Thr Leu Thr Lys Asp Ala Ala
    130                 135                 140

Tyr Val His Tyr Ala Ser Asn Glu Thr Ile Gly Gly Leu Glu Phe Asp
145                 150                 155                 160

Trp Ile Pro Glu Thr Gly Asp Val Pro Leu Val Thr Asp Met Ser Ser
                165                 170                 175

Asp Ile Leu Ser Arg Pro Leu Asp Val Ser Arg Phe Gly Leu Ile Tyr
            180                 185                 190

Ala Gly Ala Gln Lys Asn Ile Gly Pro Ser Gly Leu Val Val Val Ile
        195                 200                 205

Val Arg Glu Asp Leu Leu Gly Arg Ala Arg Ser Val Cys Pro Thr Met
    210                 215                 220

Leu Asn Tyr Lys Ile Ala Ala Asp Asn Gly Ser Met Tyr Asn Thr Pro
225                 230                 235                 240

Ala Thr Tyr Ser Trp Tyr Leu Ser Gly Leu Val Phe Glu Trp Leu Lys
                245                 250                 255

Glu Gln Gly Gly Val Thr Ala Met Glu Gln Arg Asn Arg Ala Lys Lys
            260                 265                 270

Asp Leu Leu Tyr Lys Thr Ile Asp Ala Ser Asp Phe Tyr Thr Asn Pro
        275                 280                 285

Ile Gln Pro Ser Ala Arg Ser Trp Met Asn Val Pro Phe Arg Leu Ala
    290                 295                 300

Asp Glu Arg Leu Asp Lys Pro Phe Leu Glu Gly Ala Glu Ala Arg Gly
305                 310                 315                 320

Leu Leu Asn Leu Lys Gly His Arg Ser Val Gly Gly Met Arg Ala Ser
                325                 330                 335

Ile Tyr Asn Ala Leu Gly Leu Asp Ala Val Glu Ala Leu Val Ala Tyr
            340                 345                 350

Met Ala Glu Phe Glu Lys Glu His Gly
        355                 360
```

<210> SEQ ID NO 29
<211> LENGTH: 1080
<212> TYPE: DNA
<213> ORGANISM: Bacillus subtilis (strain 168)

<400> SEQUENCE: 29

```
atggaacgta caacgaattt taacgcaggt cctgcagcgc tgccactgga agttctgcaa     60

aaagcacaga aagaatttat tgattttaac gaatccggca tgtctgttat ggagctttcc    120

caccgcagca aagagtatga agcggtgcac caaaaagcga aagcctcttt aatcgaactg    180

atgggcattc cggaagatta cgatatcttg tttcttcaag gcggggcaag ccttcaattc    240

tcaatgcttc cgatgaactt tttaacacct gaaaaaaccg cacattttgt gatgaccggc    300

gcttggtctg aaaaagcact ggcagaaacg aaactgttcg ggaacacgtc tatcaccgct    360

acaagtgaaa cagacaatta cagttatatt ccagaggttg accttacgga tgtaaaagac    420

ggcgcatatt tacatatcac atccaacaat acaattttcg gcactcagtg gcaggagttt    480

ccgaattctc caattccgct cgtagccgac atgtccagcg atattttaag cagaaaaatc    540

gatgtgtcca aatttgatgt gatctacgga ggcgcccaaa agaacctcgg cccttccggc    600

gtgactgtag tcatcatgaa aaaaagctgg ctgcaaaatg aaaatgcgaa cgtcccaaaa    660
```

```
atcttgaaat attccacgca tgtcaaagcg gattcactct acaacactcc gccgacattt    720

gcgatttata tgctgagcct cgttctggaa tggctcaagg aaaacggcgg tgtggaagct    780

gttgaacagc gcaatgaaca aaaagcgcag gttctctaca gctgtattga tgaaagcaac    840

ggcttctata aaggacatgc cagaaaagac agccgctcac gcatgaatgt cacattcacg    900

cttcgggatg acgaattaac gaaaacattc gttcagaaag caaaagatgc gaagatgatc    960

ggccttggcg gacaccgttc ggtgggaggc tgccgcgctt ctatttataa cgcggtctct   1020

ctcgaagact gtgaaaaatt agctgcgttc atgaagaaat tccagcagga aaatgagtaa   1080
```

<210> SEQ ID NO 30
<211> LENGTH: 359
<212> TYPE: PRT
<213> ORGANISM: Bacillus subtilis (strain 168)

<400> SEQUENCE: 30

```
Met Glu Arg Thr Thr Asn Phe Asn Ala Gly Pro Ala Ala Leu Pro Leu
1               5                   10                  15

Glu Val Leu Gln Lys Ala Gln Lys Glu Phe Ile Asp Phe Asn Glu Ser
            20                  25                  30

Gly Met Ser Val Met Glu Leu Ser His Arg Ser Lys Glu Tyr Glu Ala
        35                  40                  45

Val His Gln Lys Ala Lys Ser Leu Leu Ile Glu Leu Met Gly Ile Pro
    50                  55                  60

Glu Asp Tyr Asp Ile Leu Phe Leu Gln Gly Gly Ala Ser Leu Gln Phe
65                  70                  75                  80

Ser Met Leu Pro Met Asn Phe Leu Thr Pro Glu Lys Thr Ala His Phe
                85                  90                  95

Val Met Thr Gly Ala Trp Ser Glu Lys Ala Leu Ala Glu Thr Lys Leu
            100                 105                 110

Phe Gly Asn Thr Ser Ile Thr Ala Thr Ser Glu Thr Asp Asn Tyr Ser
        115                 120                 125

Tyr Ile Pro Glu Val Asp Leu Thr Asp Val Lys Asp Gly Ala Tyr Leu
    130                 135                 140

His Ile Thr Ser Asn Asn Thr Ile Phe Gly Thr Gln Trp Gln Glu Phe
145                 150                 155                 160

Pro Asn Ser Pro Ile Pro Leu Val Ala Asp Met Ser Ser Asp Ile Leu
                165                 170                 175

Ser Arg Lys Ile Asp Val Ser Lys Phe Asp Val Ile Tyr Gly Gly Ala
            180                 185                 190

Gln Lys Asn Leu Gly Pro Ser Gly Val Thr Val Val Ile Met Lys Lys
        195                 200                 205

Ser Trp Leu Gln Asn Glu Asn Ala Asn Val Pro Lys Ile Leu Lys Tyr
    210                 215                 220

Ser Thr His Val Lys Ala Asp Ser Leu Tyr Asn Thr Pro Pro Thr Phe
225                 230                 235                 240

Ala Ile Tyr Met Leu Ser Leu Val Leu Glu Trp Leu Lys Glu Asn Gly
                245                 250                 255

Gly Val Glu Ala Val Glu Gln Arg Asn Glu Gln Lys Ala Gln Val Leu
            260                 265                 270

Tyr Ser Cys Ile Asp Glu Ser Asn Gly Phe Tyr Lys Gly His Ala Arg
        275                 280                 285

Lys Asp Ser Arg Ser Arg Met Asn Val Thr Phe Thr Leu Arg Asp Asp
    290                 295                 300
```

```
Glu Leu Thr Lys Thr Phe Val Gln Lys Ala Lys Asp Ala Lys Met Ile
305                 310                 315                 320

Gly Leu Gly Gly His Arg Ser Val Gly Gly Cys Arg Ala Ser Ile Tyr
                325                 330                 335

Asn Ala Val Ser Leu Glu Asp Cys Glu Lys Leu Ala Ala Phe Met Lys
            340                 345                 350

Lys Phe Gln Gln Glu Asn Glu
        355


<210> SEQ ID NO 31
<211> LENGTH: 1269
<212> TYPE: DNA
<213> ORGANISM: Arabidopsis thaliana (Mouseear cress)

<400> SEQUENCE: 31

atggcggcgt caacgaactc attcctcatc ggaaaccaaa cccaaatccc ttctttgaaa     60

cccaaatcaa tatcccaatc ctttatccac ttcactaaac ccaacaccat caacctcacc    120

acccgaacca aatccgtttc aatccgatgc gcttccgctt caaccaccgt cggatccgag    180

cagcgagtca tcaatttcgc cgcaggtcca gccgcattac cggaaaacgt cctcctcaaa    240

gctcaatcag atctctataa ctggcgtgga tctggtatga gtgttatgga gatgagtcat    300

cgcggtaaag agtttctctc aatcattcaa aaagctgaat ctgatctccg tcagcttctc    360

gagattccat cggaatattc cgttttgttc ttacaaggtg gtgccactac tcaattcgct    420

gctttacctc tcaatctctg taaatctgat gattccgttg attacattgt tactggatct    480

tggggagata aagcttttaa ggaagctaag aaatattgta accctaaagt gatttggtct    540

ggtaaatctg agaaatatac taaagttcca acctttgatg gattggagca gagttcggac    600

gccaagtatt tgcatatatg cgccaatgag actattcatg gtgttgaatt taaagattat    660

cctcttgttg aaaaccctga tggtgttctt attgctgata tgtcttcgaa tttctgttct    720

aagccggtgg atgtatcgaa gttcggtgtg atttacgctg gtgctcagaa gaatgttggt    780

ccttctggtg tcaccattgt gatcattcga aaggatttga ttgggaatgc tagagatata    840

actccggtga tgcttgatta caagattcat gatgagaaca gctcgttgta taacacgcca    900

ccgtgtttcg ggatttatat gtgtggtctt gtgtttgatg atttgttgga gcaaggtggt    960

ttgaaggaag tggagaagaa gaaccagagg aaagctgagt tgttgtacaa tgcgattgat   1020

gagagtagag ggtttttcag gtgtcctgtt gagaagtctg tgaggtcttt gatgaatgtt   1080

ccttttacgt tggagaaatc ggagttggaa gctgagttta ttaaagaagc tgctaaggag   1140

aagatggtgc agcttaaggg acatagatca gtgggaggta tgagagcttc tatttacaat   1200

gcgatgccat tggctggtgt cgaaaagctt gttgctttca tgaaagattt tcaggcaagg   1260

catgcttga                                                            1269


<210> SEQ ID NO 32
<211> LENGTH: 422
<212> TYPE: PRT
<213> ORGANISM: Arabidopsis thaliana (Mouseear cress)

<400> SEQUENCE: 32

Met Ala Ala Ser Thr Asn Ser Phe Leu Ile Gly Asn Gln Thr Gln Ile
1               5                   10                  15

Pro Ser Leu Lys Pro Lys Ser Ile Ser Gln Ser Phe Ile His Phe Thr
            20                  25                  30
```

```
Lys Pro Asn Thr Ile Asn Leu Thr Thr Arg Thr Lys Ser Val Ser Ile
        35                  40                  45

Arg Cys Ala Ser Ala Ser Thr Thr Val Gly Ser Glu Gln Arg Val Ile
    50                  55                  60

Asn Phe Ala Ala Gly Pro Ala Ala Leu Pro Glu Asn Val Leu Leu Lys
65                  70                  75                  80

Ala Gln Ser Asp Leu Tyr Asn Trp Arg Gly Ser Gly Met Ser Val Met
                85                  90                  95

Glu Met Ser His Arg Gly Lys Glu Phe Leu Ser Ile Ile Gln Lys Ala
            100                 105                 110

Glu Ser Asp Leu Arg Gln Leu Leu Glu Ile Pro Ser Glu Tyr Ser Val
        115                 120                 125

Leu Phe Leu Gln Gly Gly Ala Thr Thr Gln Phe Ala Ala Leu Pro Leu
    130                 135                 140

Asn Leu Cys Lys Ser Asp Asp Ser Val Asp Tyr Ile Val Thr Gly Ser
145                 150                 155                 160

Trp Gly Asp Lys Ala Phe Lys Glu Ala Lys Lys Tyr Cys Asn Pro Lys
                165                 170                 175

Val Ile Trp Ser Gly Lys Ser Glu Lys Tyr Thr Lys Val Pro Thr Phe
            180                 185                 190

Asp Gly Leu Glu Gln Ser Ser Asp Ala Lys Tyr Leu His Ile Cys Ala
        195                 200                 205

Asn Glu Thr Ile His Gly Val Glu Phe Lys Asp Tyr Pro Leu Val Glu
    210                 215                 220

Asn Pro Asp Gly Val Leu Ile Ala Asp Met Ser Ser Asn Phe Cys Ser
225                 230                 235                 240

Lys Pro Val Asp Val Ser Lys Phe Gly Val Ile Tyr Ala Gly Ala Gln
                245                 250                 255

Lys Asn Val Gly Pro Ser Gly Val Thr Ile Val Ile Ile Arg Lys Asp
            260                 265                 270

Leu Ile Gly Asn Ala Arg Asp Ile Thr Pro Val Met Leu Asp Tyr Lys
        275                 280                 285

Ile His Asp Glu Asn Ser Ser Leu Tyr Asn Thr Pro Pro Cys Phe Gly
    290                 295                 300

Ile Tyr Met Cys Gly Leu Val Phe Asp Asp Leu Leu Glu Gln Gly Gly
305                 310                 315                 320

Leu Lys Glu Val Glu Lys Lys Asn Gln Arg Lys Ala Glu Leu Leu Tyr
                325                 330                 335

Asn Ala Ile Asp Glu Ser Arg Gly Phe Phe Arg Cys Pro Val Glu Lys
            340                 345                 350

Ser Val Arg Ser Leu Met Asn Val Pro Phe Thr Leu Glu Lys Ser Glu
        355                 360                 365

Leu Glu Ala Glu Phe Ile Lys Glu Ala Ala Lys Glu Lys Met Val Gln
    370                 375                 380

Leu Lys Gly His Arg Ser Val Gly Gly Met Arg Ala Ser Ile Tyr Asn
385                 390                 395                 400

Ala Met Pro Leu Ala Gly Val Glu Lys Leu Val Ala Phe Met Lys Asp
                405                 410                 415

Phe Gln Ala Arg His Ala
            420
```

<210> SEQ ID NO 33
<211> LENGTH: 1188
<212> TYPE: DNA

<213> ORGANISM: Saccharomyces cerevisiae (strain ATCC 204508 / S288c)
(Baker's yeast)

<400> SEQUENCE: 33

```
atgtctttgg aaagagagga accacaacat ttcggagcag ggccagctca aatgcctaca     60
ccagttttgc aacaagctgc taaagactta atcaatttca atgacatagg tttgggtatc    120
ggtgaaattt ctcaccgttc gaaggatgcc accaaagtga ttgaagactc taagaagcac    180
ttaatcgaac tgctaaatat tcctgacact catgaagtgt tctacttgca aggtggtggc    240
actactggtt tttcttccgt tgctactaat ttggcagctg catatgtggg taagcatggg    300
aagattgcac ctgccggtta tttagtcacc ggtagttggt ctcagaaatc ttttgaagag    360
gcaaagagat tgcacgttcc tgctgaagtt atcttcaacg ctaaagatta taacaatggc    420
aaatttggta aaattccgga tgaatccctt tgggaagata aaatcaaagg taaggctttc    480
tcatacgtgt acctatgtga gaatgaaact gttcatggtg ttgaatggcc agaattacca    540
aaatgtttag taaacgaccc caacatcgaa attgttgctg acttatccag cgacattttg    600
tctcgtaaga ttgacgtttc tcaatacggt gtcatcatgg caggcgccca aaaaaacatt    660
ggtttagcag gcttaaccct atacattatc aagaaatcca tccttaagaa tatttctggc    720
gcttctgatg aaacattaca tgaattggga gtaccaatca cccctattgc attcgactat    780
ccaacggtgg tgaagaacaa ctcagcctat aatacaattc caattttcac tttacatgtt    840
atggatctcg tgttccaaca tattttgaag aagggtggtg ttgaagcgca acaggctgaa    900
aatgaagaaa aggccaagat attatatgag gcattggatg caaattcaga tttttacaac    960
gttccagtgg atccaaagtg tagatcaaaa atgaatgtcg ttttcaccct taaaaaggac   1020
ggccttgatg accagtttct aaaagaggca gctgctcgtc atttaaccgg tttgaaagga   1080
catcgttcag ttggtgggtt cagagcctcc atctataacg cgctttcagt gaaagctgta   1140
caaaacttgg tagattttat caaggaattt gctgagaaaa acgcttaa                1188
```

<210> SEQ ID NO 34
<211> LENGTH: 395
<212> TYPE: PRT
<213> ORGANISM: Saccharomyces cerevisiae (strain ATCC 204508 / S288c)
(Baker's yeast)

<400> SEQUENCE: 34

```
Met Ser Leu Glu Arg Glu Glu Pro Gln His Phe Gly Ala Gly Pro Ala
1               5                   10                  15

Gln Met Pro Thr Pro Val Leu Gln Gln Ala Ala Lys Asp Leu Ile Asn
            20                  25                  30

Phe Asn Asp Ile Gly Leu Gly Ile Gly Glu Ile Ser His Arg Ser Lys
        35                  40                  45

Asp Ala Thr Lys Val Ile Glu Asp Ser Lys Lys His Leu Ile Glu Leu
    50                  55                  60

Leu Asn Ile Pro Asp Thr His Glu Val Phe Tyr Leu Gln Gly Gly Gly
65                  70                  75                  80

Thr Thr Gly Phe Ser Ser Val Ala Thr Asn Leu Ala Ala Ala Tyr Val
                85                  90                  95

Gly Lys His Gly Lys Ile Ala Pro Ala Gly Tyr Leu Val Thr Gly Ser
            100                 105                 110

Trp Ser Gln Lys Ser Phe Glu Glu Ala Lys Arg Leu His Val Pro Ala
        115                 120                 125

Glu Val Ile Phe Asn Ala Lys Asp Tyr Asn Asn Gly Lys Phe Gly Lys
```

```
    130                 135                 140

Ile Pro Asp Glu Ser Leu Trp Glu Asp Lys Ile Lys Gly Lys Ala Phe
145                 150                 155                 160

Ser Tyr Val Tyr Leu Cys Glu Asn Glu Thr Val His Gly Val Glu Trp
                165                 170                 175

Pro Glu Leu Pro Lys Cys Leu Val Asn Asp Pro Asn Ile Glu Ile Val
            180                 185                 190

Ala Asp Leu Ser Ser Asp Ile Leu Ser Arg Lys Ile Asp Val Ser Gln
        195                 200                 205

Tyr Gly Val Ile Met Ala Gly Ala Gln Lys Asn Ile Gly Leu Ala Gly
    210                 215                 220

Leu Thr Leu Tyr Ile Ile Lys Lys Ser Ile Leu Lys Asn Ile Ser Gly
225                 230                 235                 240

Ala Ser Asp Glu Thr Leu His Glu Leu Gly Val Pro Ile Thr Pro Ile
                245                 250                 255

Ala Phe Asp Tyr Pro Thr Val Val Lys Asn Asn Ser Ala Tyr Asn Thr
            260                 265                 270

Ile Pro Ile Phe Thr Leu His Val Met Asp Leu Val Phe Gln His Ile
        275                 280                 285

Leu Lys Lys Gly Gly Val Glu Ala Gln Gln Ala Glu Asn Glu Glu Lys
    290                 295                 300

Ala Lys Ile Leu Tyr Glu Ala Leu Asp Ala Asn Ser Asp Phe Tyr Asn
305                 310                 315                 320

Val Pro Val Asp Pro Lys Cys Arg Ser Lys Met Asn Val Val Phe Thr
                325                 330                 335

Leu Lys Lys Asp Gly Leu Asp Asp Gln Phe Leu Lys Glu Ala Ala Ala
            340                 345                 350

Arg His Leu Thr Gly Leu Lys Gly His Arg Ser Val Gly Gly Phe Arg
        355                 360                 365

Ala Ser Ile Tyr Asn Ala Leu Ser Val Lys Ala Val Gln Asn Leu Val
    370                 375                 380

Asp Phe Ile Lys Glu Phe Ala Glu Lys Asn Ala
385                 390                 395
```

<210> SEQ ID NO 35
<211> LENGTH: 1197
<212> TYPE: DNA
<213> ORGANISM: Cupriavidus necator (strain ATCC 17699 / H16 / DSM 428 / Stanier 337) (Ralstonia eutropha)

<400> SEQUENCE: 35

```
ttgggtaaca ccggcagcca tttttccatt ccccgtctca tgaacgatcc ccagaatccc     60

gctcttgccg gcatgatgca gcgtgcattg gccgaacgtg tctacaactt ctcccctggc    120

ccggcggcgc tgcccgccga agtgctgcag caggctgccg aggagatgct gtcctggcac    180

gggaccgggg tttcggtgat ggaaatgagc caccgcagcc gcgaattcga aagcatccat    240

aacgaagcga tcgctgacct gcgcgagttg ctgcacatcc ccgccaattt caaggtgctg    300

ttcctgcaag gtggcgccat tggcgaaaac gccatcgtgc cgctgaacct gatgcggctg    360

cgcagcgccg agcagcccaa ggccgatttc gtcgtcaccg gcacctggtc ggtcaagacc    420

gagcaggaag cccgccgcta tggcgcggtc aatatcgcgg ccaccagcga ggcggagaaa    480

ttccaccgca tccccgacat tgctgactgg aagctgtcgg acgatgccgg gtacgtgcac    540

ctgtgcacca acgagaccat cgtcggcgtg gagttccagg acattcccga tatcggccag    600
```

```
gtcaagggcg accgcgtggt ggtggcggat gcttccagcc atatcctgtc gcgcccgatc    660

gactggtcgc gcgtgcaggt ggtctacggc ggcgcgcaga agaatatcgg cccggccggc    720

gtcaccatcg tgatcgtgcg cgacgacctg atcggccatg cccacccgct gtgcccgtcg    780

gcattcaact ggcgcctggt ggccgagcac aactcgatgt acaacacgcc gccgacctat    840

gcgatctata tcgccggcct ggtcttcaag tggctcaagc gccagggcgg cgtgcccgcg    900

atcgagcagc gcaatatcgc caaggcgtcg gcgctgtaca actacctgga ccagagcgat    960

ttctatcgca acgagatcca tccgagctgc cgctcgcgca tgaacgtgcc gttcttcctg   1020

ggcgacgaat cgcgcaatga ggtgttcctg caacaggcgc gggccaacgg cctggtgcaa   1080

ctcaagggac acaagaccgt tggcggcatg cgcgccagca tctataacgc gatgccgctg   1140

gaaggcgtga tggcgctggt cgatttcatg cgcgagttcg agcgtacgtc cgcctga      1197


<210> SEQ ID NO 36
<211> LENGTH: 398
<212> TYPE: PRT
<213> ORGANISM: Cupriavidus necator (strain ATCC 17699 / H16 / DSM 428 /
      Stanier 337) (Ralstonia eutropha)

<400> SEQUENCE: 36

Met Gly Asn Thr Gly Ser His Phe Ser Ile Pro Arg Leu Met Asn Asp
1               5                   10                  15

Pro Gln Asn Pro Ala Leu Ala Gly Met Met Gln Arg Ala Leu Ala Glu
            20                  25                  30

Arg Val Tyr Asn Phe Ser Pro Gly Pro Ala Ala Leu Pro Ala Glu Val
        35                  40                  45

Leu Gln Gln Ala Ala Glu Glu Met Leu Ser Trp His Gly Thr Gly Val
    50                  55                  60

Ser Val Met Glu Met Ser His Arg Ser Arg Glu Phe Glu Ser Ile His
65                  70                  75                  80

Asn Glu Ala Ile Ala Asp Leu Arg Glu Leu Leu His Ile Pro Ala Asn
                85                  90                  95

Phe Lys Val Leu Phe Leu Gln Gly Gly Ala Ile Gly Glu Asn Ala Ile
            100                 105                 110

Val Pro Leu Asn Leu Met Arg Leu Arg Ser Ala Glu Gln Pro Lys Ala
        115                 120                 125

Asp Phe Val Val Thr Gly Thr Trp Ser Val Lys Thr Glu Gln Glu Ala
    130                 135                 140

Arg Arg Tyr Gly Ala Val Asn Ile Ala Ala Thr Ser Glu Ala Glu Lys
145                 150                 155                 160

Phe His Arg Ile Pro Asp Ile Ala Asp Trp Lys Leu Ser Asp Asp Ala
                165                 170                 175

Gly Tyr Val His Leu Cys Thr Asn Glu Thr Ile Val Gly Val Glu Phe
            180                 185                 190

Gln Asp Ile Pro Asp Ile Gly Gln Val Lys Gly Asp Arg Val Val Val
        195                 200                 205

Ala Asp Ala Ser Ser His Ile Leu Ser Arg Pro Ile Asp Trp Ser Arg
    210                 215                 220

Val Gln Val Val Tyr Gly Gly Ala Gln Lys Asn Ile Gly Pro Ala Gly
225                 230                 235                 240

Val Thr Ile Val Ile Val Arg Asp Asp Leu Ile Gly His Ala His Pro
                245                 250                 255

Leu Cys Pro Ser Ala Phe Asn Trp Arg Leu Val Ala Glu His Asn Ser
            260                 265                 270
```

```
Met Tyr Asn Thr Pro Pro Thr Tyr Ala Ile Tyr Ile Ala Gly Leu Val
        275                 280                 285

Phe Lys Trp Leu Lys Arg Gln Gly Gly Val Pro Ala Ile Glu Gln Arg
    290                 295                 300

Asn Ile Ala Lys Ala Ser Ala Leu Tyr Asn Tyr Leu Asp Gln Ser Asp
305                 310                 315                 320

Phe Tyr Arg Asn Glu Ile His Pro Ser Cys Arg Ser Arg Met Asn Val
                325                 330                 335

Pro Phe Phe Leu Gly Asp Glu Ser Arg Asn Glu Val Phe Leu Gln Gln
            340                 345                 350

Ala Arg Ala Asn Gly Leu Val Gln Leu Lys Gly His Lys Thr Val Gly
        355                 360                 365

Gly Met Arg Ala Ser Ile Tyr Asn Ala Met Pro Leu Glu Gly Val Met
    370                 375                 380

Ala Leu Val Asp Phe Met Arg Glu Phe Glu Arg Thr Ser Ala
385                 390                 395


<210> SEQ ID NO 37
<211> LENGTH: 1098
<212> TYPE: DNA
<213> ORGANISM: Lactococcus lactis subsp. lactis (strain IL1403)
      (Streptococcus lactis)

<400> SEQUENCE: 37

atgatttata attttggcgc aggacccagt gtacttccaa aggaagtctt gaagaaggtt     60

caagaagaac tgttagactt tgaaaaaagt ggtatgtcag tgatggaaat ttcgcatcgc    120

tccaaggctt tccaaaaagt aattgatgag gctgagaacg atttgcgtga tttgatgtca    180

attcctcaaa actataaaat tttgttttta caagggggag cttccagtca attttcaatg    240

gttccaatga atttggcaat tggcaaaaag gcttattaca atatttcggg cgcctttggt    300

gaaaaggctt atgatgaagc ggtgaaattg agtcatttcc ttgatttgat ggcgattagt    360

ttgggctcga ctaaaaaaga taattataat catctattga aaattgataa atctaaaatt    420

gatgaaaaaa atggggccta tctccatttg acaacgaata atacgattga aggaacaagt    480

atttttcctg aaaatttgcc tgagtttgca agccttcctt tggttgctga tatgagttca    540

aatattttgg cggttgatta tgatgtgagt aaatttggat taatttacgc tggagctcag    600

aaaaatttag gtattgctgg tttaaccatt gtcattattc gtgaagactt attgaatgaa    660

gctgaaagcc tctcatcaat gatggattat cagattttgg ttgaaaatgg ctcgatgtac    720

aataccccgc cgacttttgc tatttatgtg gccgggctgg ttttcaaatg ggtaaaagcg    780

caaggtggcg taaaaaaact cgaagaaatg aatcagagaa aagctcaatt gttgtatgat    840

ttaattgacc aatctgactt ttatcagaac ccaatcaaaa ataaagatga gcggtcgatt    900

tgcaatgttg tttttacaag tccaagtcaa gaattggatg agctattcac ccaaaaagct    960

gaagaaaaag gtttcaaatc actcaaaggt catcgttccg tgggaggaat gagagcaagt   1020

atttacaacg cttttccttt agagggggtt gttgaattag tgaaatttat gaaagaattt   1080

gaagagggat ataaatga                                                1098


<210> SEQ ID NO 38
<211> LENGTH: 365
<212> TYPE: PRT
<213> ORGANISM: Lactococcus lactis subsp. lactis (strain IL1403)
      (Streptococcus lactis)
```

<400> SEQUENCE: 38

```
Met Ile Tyr Asn Phe Gly Ala Gly Pro Ser Val Leu Pro Lys Glu Val
1               5                   10                  15

Leu Lys Lys Val Gln Glu Glu Leu Leu Asp Phe Glu Lys Ser Gly Met
            20                  25                  30

Ser Val Met Glu Ile Ser His Arg Ser Lys Ala Phe Gln Lys Val Ile
        35                  40                  45

Asp Glu Ala Glu Asn Asp Leu Arg Asp Leu Met Ser Ile Pro Gln Asn
    50                  55                  60

Tyr Lys Ile Leu Phe Leu Gln Gly Gly Ala Ser Ser Gln Phe Ser Met
65                  70                  75                  80

Val Pro Met Asn Leu Ala Ile Gly Lys Lys Ala Tyr Tyr Asn Ile Ser
                85                  90                  95

Gly Ala Phe Gly Glu Lys Ala Tyr Asp Glu Ala Val Lys Leu Ser His
            100                 105                 110

Phe Leu Asp Leu Met Ala Ile Ser Leu Gly Ser Thr Lys Lys Asp Asn
        115                 120                 125

Tyr Asn His Leu Leu Lys Ile Asp Lys Ser Lys Ile Asp Glu Lys Asn
    130                 135                 140

Gly Ala Tyr Leu His Leu Thr Thr Asn Asn Thr Ile Glu Gly Thr Ser
145                 150                 155                 160

Ile Phe Pro Glu Asn Leu Pro Glu Phe Ala Ser Leu Pro Leu Val Ala
                165                 170                 175

Asp Met Ser Ser Asn Ile Leu Ala Val Asp Tyr Asp Val Ser Lys Phe
            180                 185                 190

Gly Leu Ile Tyr Ala Gly Ala Gln Lys Asn Leu Gly Ile Ala Gly Leu
        195                 200                 205

Thr Ile Val Ile Ile Arg Glu Asp Leu Leu Asn Glu Ala Glu Ser Leu
    210                 215                 220

Ser Ser Met Met Asp Tyr Gln Ile Leu Val Glu Asn Gly Ser Met Tyr
225                 230                 235                 240

Asn Thr Pro Pro Thr Phe Ala Ile Tyr Val Ala Gly Leu Val Phe Lys
                245                 250                 255

Trp Val Lys Ala Gln Gly Gly Val Lys Lys Leu Glu Glu Met Asn Gln
            260                 265                 270

Arg Lys Ala Gln Leu Leu Tyr Asp Leu Ile Asp Gln Ser Asp Phe Tyr
        275                 280                 285

Gln Asn Pro Ile Lys Asn Lys Asp Glu Arg Ser Ile Cys Asn Val Val
    290                 295                 300

Phe Thr Ser Pro Ser Gln Glu Leu Asp Glu Leu Phe Thr Gln Lys Ala
305                 310                 315                 320

Glu Glu Lys Gly Phe Lys Ser Leu Lys Gly His Arg Ser Val Gly Gly
                325                 330                 335

Met Arg Ala Ser Ile Tyr Asn Ala Phe Pro Leu Glu Gly Val Val Glu
            340                 345                 350

Leu Val Lys Phe Met Lys Glu Phe Glu Glu Gly Tyr Lys
        355                 360                 365
```

<210> SEQ ID NO 39
<211> LENGTH: 1083
<212> TYPE: DNA
<213> ORGANISM: Clostridium beijerinckii (strain ATCC 51743 / NCIMB 8052) (Clostridium acetobutylicum)

<400> SEQUENCE: 39

```
atgtcaagag tttataattt ttcagcagga ccagctgtat taccggagtc agtcctaaga     60

gaagctgcgg gggaaatgct agactacaag ggacaggca tgtcagttat ggagatgagt    120

catcgttcta aagcgttcga agaaatcatc accgatgctg aaaaaacatt aagagaatta    180

atgaatattc cggataacta taaggtatta ttccttcaag gtggggcatc acaacaattt    240

gcaatgattc caatgaatct aatgaaaaat aaagttgtgg atcatattat tacagggcaa    300

tgggcaaaaa aggcagcgtc agaagcaaaa atatttggaa aagttaatat attagcgtct    360

tcagaggata aaactttttc atatatacca gatttaaagg atttaaaagt ttcagaggat    420

gcagactatg tttacatatg tcataacaat acaatctatg gaactacgta taaagaatta    480

ccaaacgttg ggataagat attagtagca gatatgtcat cagatttctt atctgagcca    540

gtagatgtat caaaatatgg actaatattt gcaggagtac aaaaaaatgc aggaccagct    600

ggtgttgttg tagtaataat tcgtgaagat ttaatcacag aagatgtatt accagggact    660

ccaacaatgt taagatataa ggttcatgca gacaataaat cactatataa tacaccacca    720

gcatatggaa tatatatatg cggaaaagta tttaaatggg ttaagaataa gggtggacta    780

gaagctatga agaaaattaa tgaagaaaaa gcttctattt tatatgattt tcttgattca    840

agtagcatgt ttaaaggaac tgttgtaaag aaagatcgtt ctttaatgaa tgtaccattt    900

gtaacaggtt cagatgaact agatgctaaa tttgtaaaag aagctaaagc agtaggattt    960

gaaaatctaa aggacatag aacagttggt gggatgagag caagtatata taatgctatg   1020

ccaattgaag gtgttaaaga tttagtagaa ttcatgagaa aattcgaaga agacaataag   1080

taa                                                                 1083
```

<210> SEQ ID NO 40
<211> LENGTH: 360
<212> TYPE: PRT
<213> ORGANISM: Clostridium beijerinckii (strain ATCC 51743 / NCIMB 8052) (Clostridium acetobutylicum)

<400> SEQUENCE: 40

```
Met Ser Arg Val Tyr Asn Phe Ser Ala Gly Pro Ala Val Leu Pro Glu
1               5                   10                  15

Ser Val Leu Arg Glu Ala Ala Gly Glu Met Leu Asp Tyr Lys Gly Thr
            20                  25                  30

Gly Met Ser Val Met Glu Met Ser His Arg Ser Lys Ala Phe Glu Glu
        35                  40                  45

Ile Ile Thr Asp Ala Glu Lys Thr Leu Arg Glu Leu Met Asn Ile Pro
    50                  55                  60

Asp Asn Tyr Lys Val Leu Phe Leu Gln Gly Gly Ala Ser Gln Gln Phe
65                  70                  75                  80

Ala Met Ile Pro Met Asn Leu Met Lys Asn Lys Val Val Asp His Ile
                85                  90                  95

Ile Thr Gly Gln Trp Ala Lys Lys Ala Ala Ser Glu Ala Lys Ile Phe
            100                 105                 110

Gly Lys Val Asn Ile Leu Ala Ser Ser Glu Asp Lys Thr Phe Ser Tyr
        115                 120                 125

Ile Pro Asp Leu Lys Asp Leu Lys Val Ser Glu Asp Ala Asp Tyr Val
    130                 135                 140

Tyr Ile Cys His Asn Asn Thr Ile Tyr Gly Thr Thr Tyr Lys Glu Leu
145                 150                 155                 160

Pro Asn Val Gly Asp Lys Ile Leu Val Ala Asp Met Ser Ser Asp Phe
```

```
                165                 170                 175

Leu Ser Glu Pro Val Asp Val Ser Lys Tyr Gly Leu Ile Phe Ala Gly
            180                 185                 190

Val Gln Lys Asn Ala Gly Pro Ala Gly Val Val Val Val Ile Ile Arg
        195                 200                 205

Glu Asp Leu Ile Thr Glu Asp Val Leu Pro Gly Thr Pro Thr Met Leu
    210                 215                 220

Arg Tyr Lys Val His Ala Asp Asn Lys Ser Leu Tyr Asn Thr Pro Pro
225                 230                 235                 240

Ala Tyr Gly Ile Tyr Ile Cys Gly Lys Val Phe Lys Trp Val Lys Asn
                245                 250                 255

Lys Gly Gly Leu Glu Ala Met Lys Lys Ile Asn Glu Glu Lys Ala Ser
            260                 265                 270

Ile Leu Tyr Asp Phe Leu Asp Ser Ser Ser Met Phe Lys Gly Thr Val
        275                 280                 285

Val Lys Lys Asp Arg Ser Leu Met Asn Val Pro Phe Val Thr Gly Ser
    290                 295                 300

Asp Glu Leu Asp Ala Lys Phe Val Lys Glu Ala Lys Ala Val Gly Phe
305                 310                 315                 320

Glu Asn Leu Lys Gly His Arg Thr Val Gly Gly Met Arg Ala Ser Ile
                325                 330                 335

Tyr Asn Ala Met Pro Ile Glu Gly Val Lys Asp Leu Val Glu Phe Met
            340                 345                 350

Arg Lys Phe Glu Glu Asp Asn Lys
        355                 360
```

<210> SEQ ID NO 41
<211> LENGTH: 978
<212> TYPE: DNA
<213> ORGANISM: Lactococcus lactis subsp. Lactis

<400> SEQUENCE: 41

```
atggctgata aacaacgtaa aaaagttatc cttgtaggtg acggtgctgt aggttcatca      60

tacgcttttg ctcttgtaaa ccaagggatt gcacaagaat taggaattgt tgaccttttt     120

aaagaaaaaa ctcaaggaga tgcagaagac ctttctcatg ccttggcatt tacttcacct     180

aaaaagattt actctgcaga ctactctgat gcaagcgacg ctgacctcgt agtcttgact     240

tctggtgctc cacaaaaacc aggtgaaact cgtcttgacc ttgttgaaaa aaatcttcgt     300

atcactaaag atgttgtcac taaaattgtt gcttcaggtt tcaaaggaat cttccttgtt     360

gctgctaacc cagttgatat cttgacatac gctacttgga aattctcagg tttccctaaa     420

aaccgcgttg taggttcagg tacttcactt gatactgcac gtttccgtca agcattggca     480

gaaaaagttg atgttgacgc tcgttcaatc cacgcataca tcatgggtga acacggtgac     540

tcagaatttg ccgtttggtc acacgctaac gttgctggtg ttaaattgga acaatggttc     600

caagaaaatg actaccttaa cgaagctgaa atcgttgaat tgtttgaatc tgtacgtgat     660

gctgcttact caatcatcgc taaaaaaggt gcaacattct atggtgtcgc tgtagctctt     720

gctcgtatta ctaaagcaat tcttgatgat gaacatgcag tacttccagt atcagtattc     780

caagatggac aatatggcgt aagcgactgc taccttggtc aaccagctgt agttggtgct     840

gaaggtgttg ttaacccaat ccacattcca ttgaatgatg ctgaaatgca aaaaatggaa     900

gcttctggtg ctcaattgaa agcaatcatt gacgaagctt ttgctaaaga agaatttgct     960

tctgcagtta aaaactaa                                                   978
```

<210> SEQ ID NO 42
<211> LENGTH: 325
<212> TYPE: PRT
<213> ORGANISM: Lactococcus lactis subsp. Lactis

<400> SEQUENCE: 42

```
Met Ala Asp Lys Gln Arg Lys Lys Val Ile Leu Val Gly Asp Gly Ala
1               5                   10                  15

Val Gly Ser Ser Tyr Ala Phe Ala Leu Val Asn Gln Gly Ile Ala Gln
            20                  25                  30

Glu Leu Gly Ile Val Asp Leu Phe Lys Glu Lys Thr Gln Gly Asp Ala
        35                  40                  45

Glu Asp Leu Ser His Ala Leu Ala Phe Thr Ser Pro Lys Lys Ile Tyr
    50                  55                  60

Ser Ala Asp Tyr Ser Asp Ala Ser Asp Ala Asp Leu Val Val Leu Thr
65                  70                  75                  80

Ser Gly Ala Pro Gln Lys Pro Gly Glu Thr Arg Leu Asp Leu Val Glu
                85                  90                  95

Lys Asn Leu Arg Ile Thr Lys Asp Val Val Thr Lys Ile Val Ala Ser
            100                 105                 110

Gly Phe Lys Gly Ile Phe Leu Val Ala Ala Asn Pro Val Asp Ile Leu
        115                 120                 125

Thr Tyr Ala Thr Trp Lys Phe Ser Gly Phe Pro Lys Asn Arg Val Val
    130                 135                 140

Gly Ser Gly Thr Ser Leu Asp Thr Ala Arg Phe Arg Gln Ala Leu Ala
145                 150                 155                 160

Glu Lys Val Asp Val Asp Ala Arg Ser Ile His Ala Tyr Ile Met Gly
                165                 170                 175

Glu His Gly Asp Ser Glu Phe Ala Val Trp Ser His Ala Asn Val Ala
            180                 185                 190

Gly Val Lys Leu Glu Gln Trp Phe Gln Glu Asn Asp Tyr Leu Asn Glu
        195                 200                 205

Ala Glu Ile Val Glu Leu Phe Glu Ser Val Arg Asp Ala Ala Tyr Ser
    210                 215                 220

Ile Ile Ala Lys Lys Gly Ala Thr Phe Tyr Gly Val Ala Val Ala Leu
225                 230                 235                 240

Ala Arg Ile Thr Lys Ala Ile Leu Asp Asp Glu His Ala Val Leu Pro
                245                 250                 255

Val Ser Val Phe Gln Asp Gly Gln Tyr Gly Val Ser Asp Cys Tyr Leu
            260                 265                 270

Gly Gln Pro Ala Val Val Gly Ala Glu Gly Val Val Asn Pro Ile His
        275                 280                 285

Ile Pro Leu Asn Asp Ala Glu Met Gln Lys Met Glu Ala Ser Gly Ala
    290                 295                 300

Gln Leu Lys Ala Ile Ile Asp Glu Ala Phe Ala Lys Glu Glu Phe Ala
305                 310                 315                 320

Ser Ala Val Lys Asn
                325
```

<210> SEQ ID NO 43
<211> LENGTH: 362
<212> TYPE: PRT
<213> ORGANISM: Citrobacter koseri

<400> SEQUENCE: 43

```
Met Ala Gln Val Phe Asn Phe Ser Ser Gly Pro Ala Met Leu Pro Ala
1               5                   10                  15

Glu Val Leu Lys Leu Ala Gln Gln Asp Leu Arg Asp Trp His Gly Leu
            20                  25                  30

Gly Thr Ser Val Met Glu Ile Ser His Arg Gly Lys Glu Phe Ile Gln
        35                  40                  45

Val Ala Glu Glu Ala Glu Gln Asp Phe Arg Asp Leu Leu Ser Ile Pro
    50                  55                  60

Ser Asn Tyr Lys Val Leu Phe Cys His Gly Gly Gly Arg Gly Gln Phe
65                  70                  75                  80

Ala Ala Ile Pro Leu Asn Ile Leu Gly Asp Lys Thr Ser Ala Asp Tyr
                85                  90                  95

Val Asp Ala Gly Tyr Trp Ala Ala Ser Ala Ile Lys Glu Ala Lys Lys
            100                 105                 110

Tyr Cys Ser Pro Asn Val Ile Asp Ala Lys Val Thr Val Asp Gly Leu
        115                 120                 125

Arg Ala Val Lys Pro Met Ser Glu Trp Gln Leu Ser Asp Asn Ala Ala
    130                 135                 140

Tyr Val His Tyr Cys Pro Asn Glu Thr Ile Asp Gly Ile Ala Ile Asp
145                 150                 155                 160

Glu Thr Pro Asn Phe Gly Ser Asp Val Val Val Ala Ala Asp Phe Ser
                165                 170                 175

Ser Thr Ile Leu Ser Ala Pro Leu Asp Val Ser Arg Tyr Gly Val Ile
            180                 185                 190

Tyr Ala Gly Ala Gln Lys Asn Ile Gly Pro Ala Gly Leu Thr Ile Val
        195                 200                 205

Ile Val Arg Glu Asp Leu Leu Gly Lys Ala Asn Ile Ala Cys Pro Ser
    210                 215                 220

Ile Leu Asp Tyr Thr Val Leu Asn Asp Asn Asp Ser Met Phe Asn Thr
225                 230                 235                 240

Pro Pro Thr Phe Ala Trp Tyr Leu Ser Gly Leu Val Phe Lys Trp Leu
                245                 250                 255

Lys Ala Gln Gly Gly Val Ala Ala Met Asn Lys Ile Asn Gln Gln Lys
            260                 265                 270

Ala Glu Leu Leu Tyr Gly Val Ile Asp Asn Ser Asp Phe Tyr Arg Asn
        275                 280                 285

Asp Val Ala Lys Ser Asn Arg Ser Arg Met Asn Val Pro Phe Gln Leu
    290                 295                 300

Ala Asp Ser Ala Leu Asp Lys Val Phe Leu Glu Glu Ser Phe Ala Ala
305                 310                 315                 320

Gly Leu His Ala Leu Lys Gly His Arg Val Val Gly Gly Met Arg Ala
                325                 330                 335

Ser Ile Tyr Asn Ala Met Pro Leu Glu Gly Val Lys Ala Leu Thr Asp
            340                 345                 350

Phe Met Val Asp Phe Glu Arg Arg His Gly
        355                 360
```

<210> SEQ ID NO 44
<211> LENGTH: 362
<212> TYPE: PRT
<213> ORGANISM: Enterobacter sp.

<400> SEQUENCE: 44

```
Met Ala Gln Val Phe Asn Phe Ser Ser Gly Pro Ala Met Leu Pro Val
```

```
1               5                   10                  15

Asp Val Leu Lys Gln Ala Gln Gln Glu Leu Cys Asp Trp Gln Gly Leu
            20                  25                  30

Gly Thr Ser Val Met Glu Ile Ser His Arg Gly Lys Glu Phe Ile Gln
        35                  40                  45

Val Ala Glu Glu Ala Glu Lys Asp Phe Arg Asp Leu Leu Asn Ile Pro
    50                  55                  60

Ser Asn Tyr Lys Val Leu Phe Cys His Gly Gly Gly Arg Gly Gln Phe
65                  70                  75                  80

Ala Gly Ile Pro Leu Asn Leu Leu Gly Asp Lys Thr Gly Ala Asp Tyr
                85                  90                  95

Val Asp Ala Gly Tyr Trp Ala Ala Ser Ala Val Lys Glu Ala His Lys
            100                 105                 110

Tyr Cys Thr Pro Asn Val Ile Asp Ala Lys Val Thr Val Asp Gly Leu
        115                 120                 125

Arg Ala Val Lys Pro Met Ser Glu Trp Gln Leu Ser Asp Asn Ala Ala
    130                 135                 140

Tyr Leu His Tyr Cys Pro Asn Glu Thr Ile Asp Gly Ile Ala Ile His
145                 150                 155                 160

Glu Glu Pro Asn Phe Gly Asn Asp Val Val Val Thr Ala Asp Leu Ser
                165                 170                 175

Ser Thr Ile Leu Ser Gly Pro Leu Asp Val Ser Arg Tyr Gly Val Ile
            180                 185                 190

Tyr Ala Gly Ala Gln Lys Asn Ile Gly Pro Ala Gly Leu Thr Leu Val
        195                 200                 205

Ile Val Arg Glu Asp Leu Leu Gly Lys Ala His Lys Ala Cys Pro Ser
    210                 215                 220

Ile Leu Asp Tyr Thr Val Leu Asn Asp Asn Asp Ser Met Phe Asn Thr
225                 230                 235                 240

Pro Pro Thr Phe Ala Trp Tyr Leu Ser Gly Leu Val Phe Lys Trp Leu
                245                 250                 255

Lys Lys Asn Gly Gly Val Ala Gln Met Asp Lys Ile Asn Gln Gln Lys
            260                 265                 270

Ala Glu Leu Leu Tyr Ser Thr Ile Asp Gly Ser Asp Phe Tyr Arg Asn
        275                 280                 285

Asp Val Ala Lys Ala Asn Arg Ser Arg Met Asn Val Pro Phe Gln Leu
    290                 295                 300

Ala Asp Ser Asn Leu Asp Lys Val Phe Leu Glu Glu Ser Phe Ala Ala
305                 310                 315                 320

Gly Leu His Ala Leu Lys Gly His Arg Val Val Gly Gly Met Arg Ala
                325                 330                 335

Ser Ile Tyr Asn Ala Met Pro Leu Glu Gly Val Asn Thr Leu Thr Asp
            340                 345                 350

Phe Met Val Asp Phe Glu Arg Arg His Gly
        355                 360


<210> SEQ ID NO 45
<211> LENGTH: 361
<212> TYPE: PRT
<213> ORGANISM: Pectobacterium carotovorum

<400> SEQUENCE: 45

Met Thr Gln Ile Phe Asn Phe Ser Ala Gly Pro Ala Met Leu Pro Val
1               5                   10                  15
```

```
Glu Val Leu Arg Arg Ala Glu Gln Glu Leu Cys Asn Trp Asn Gly Leu
            20                  25                  30

Gly Thr Ser Val Met Glu Ile Ser His Arg Ser Lys Glu Phe Met Gln
        35                  40                  45

Val Ala Ala Glu Ser Glu Gln Asn Leu Arg Asp Leu Leu Lys Ile Pro
    50                  55                  60

Ser Asn Tyr Lys Val Leu Phe Cys His Gly Gly Ala Arg Ala Gln Phe
65                  70                  75                  80

Ala Ala Val Pro Leu Asn Leu Leu Gly Glu Arg Ser Thr Ala Asp Tyr
                85                  90                  95

Ile Asp Gly Gly Tyr Trp Ala His Ser Ala Val Asn Glu Ala Glu Lys
            100                 105                 110

Tyr Cys Thr Pro Asn Val Ile Asp Val Lys Thr Arg Val Asp Gly Leu
        115                 120                 125

Arg Gly Val Lys Pro Met Arg Glu Trp Gln Leu Ser Asp Asp Ala Ala
    130                 135                 140

Phe Val His Tyr Cys Pro Asn Glu Thr Ile Asp Gly Ile Ala Ile Glu
145                 150                 155                 160

Glu Glu Pro Asp Phe Gly Asp Lys Ile Val Val Ala Asp Tyr Ser Ser
                165                 170                 175

Ser Ile Leu Ser Arg Arg Ile Asp Val Ser Arg Tyr Gly Val Ile Tyr
            180                 185                 190

Ala Gly Ala Gln Lys Asn Ile Gly Pro Ala Gly Leu Thr Leu Val Ile
        195                 200                 205

Val Arg Asp Asp Leu Leu Gly Lys Ala Arg Arg Glu Leu Pro Ser Ile
    210                 215                 220

Leu Asp Tyr Gln Ile Leu Ala Asp Asn Asp Ser Met Phe Asn Thr Pro
225                 230                 235                 240

Pro Thr Phe Ala Trp Tyr Leu Ser Gly Met Val Phe Lys Trp Leu Lys
                245                 250                 255

Glu His Gly Gly Leu Ala Glu Met Glu Lys Arg Asn Gln Glu Lys Ala
            260                 265                 270

Asp Leu Leu Tyr Ser Ala Ile Asp Gly Asn Asp Phe Tyr Arg Asn Asp
        275                 280                 285

Val Ala Val Ala Asn Arg Ser Arg Met Asn Val Pro Phe Leu Leu Ala
    290                 295                 300

Asp Ala Ala Leu Asp Lys Val Phe Leu Glu Glu Ser Val Ala Ala Gly
305                 310                 315                 320

Leu His Ala Leu Lys Gly His Arg Val Val Gly Gly Met Arg Ala Ser
                325                 330                 335

Ile Tyr Asn Ala Met Pro Leu Glu Gly Val Lys Ala Leu Thr Glu Phe
            340                 345                 350

Met Ala Asp Phe Ala Arg Arg His Gly
        355                 360
```

<210> SEQ ID NO 46
<211> LENGTH: 361
<212> TYPE: PRT
<213> ORGANISM: Dickeya zeae

<400> SEQUENCE: 46

```
Met Thr Gln Val Phe Asn Phe Ser Ala Gly Pro Ala Met Leu Pro Val
1               5                   10                  15

Glu Val Leu Arg Arg Ala Glu Gln Glu Leu Cys Asn Trp Arg Gly Leu
            20                  25                  30
```

```
Gly Thr Ser Val Met Glu Ile Ser His Arg Ser Lys Glu Phe Met Gln
        35                  40                  45

Val Ala Ser Glu Ser Glu Gln Asp Leu Arg Asp Leu Leu Lys Ile Pro
    50                  55                  60

Ser Asn Tyr Lys Val Leu Phe Cys His Gly Gly Ala Arg Ala Gln Phe
65                  70                  75                  80

Ala Ala Val Pro Leu Asn Leu Leu Gly Glu Lys Thr His Ala Asp Tyr
                85                  90                  95

Ile Asp Gly Gly Tyr Trp Ala His Ser Ala Val Lys Glu Ala Glu Lys
            100                 105                 110

Tyr Leu Thr Pro Thr Val Ile Asp Val Lys Thr Arg Val Asp Gly Leu
        115                 120                 125

Arg Gly Val Lys Pro Met Ser Glu Trp Ala Leu Ser Asp Asp Ala Ala
    130                 135                 140

Tyr Val His Tyr Cys Pro Asn Glu Thr Ile Asp Gly Leu Ala Ile Glu
145                 150                 155                 160

Glu Glu Pro Asp Phe Gly Asp Lys Ile Val Val Ala Asp Tyr Ser Ser
                165                 170                 175

Ser Ile Leu Ser Arg Pro Leu Asp Val Ser Arg Tyr Gly Val Ile Tyr
            180                 185                 190

Ala Gly Ala Gln Lys Asn Val Gly Pro Ala Gly Leu Thr Leu Val Ile
        195                 200                 205

Val Arg Asp Asp Leu Leu Gly Lys Ala Arg Arg Glu Leu Pro Ser Ile
    210                 215                 220

Leu Asp Tyr Lys Ile Leu Ala Asp Asn Asp Ser Met Phe Asn Thr Pro
225                 230                 235                 240

Pro Thr Phe Ala Trp Tyr Leu Ser Gly Met Val Phe Lys Trp Leu Lys
                245                 250                 255

Glu Gln Gly Gly Leu Leu Glu Met Glu Lys Arg Asn Gln Ala Lys Ala
            260                 265                 270

Asp Leu Leu Tyr Ser Ala Ile Asp Gly Ser Asp Phe Tyr Arg Asn Asp
        275                 280                 285

Val Val Pro Gly Ser Arg Ser Arg Met Asn Val Pro Phe Gln Leu Ala
    290                 295                 300

Asp Ala Ala Leu Asp Pro Val Phe Leu Gln Glu Ala Gln Ala Ala Gly
305                 310                 315                 320

Leu His Ala Leu Lys Gly His Arg Val Val Gly Gly Met Arg Ala Ser
                325                 330                 335

Ile Tyr Asn Ala Met Pro Leu Ser Gly Val Glu Ala Leu Thr Glu Phe
            340                 345                 350

Met Ala Asp Phe Glu Arg Arg His Gly
        355                 360


<210> SEQ ID NO 47
<211> LENGTH: 361
<212> TYPE: PRT
<213> ORGANISM: Pseudomonas putida

<400> SEQUENCE: 47

Met Ser Lys Arg Ala Phe Asn Phe Cys Ala Gly Pro Ala Ala Leu Pro
1               5                   10                  15

Asp Ala Val Leu Gln Arg Ala Gln Ala Glu Met Leu Asp Trp Arg Gly
            20                  25                  30

Lys Gly Leu Ser Val Met Glu Met Ser His Arg Ser Asp Asp Tyr Val
```

```
        35                  40                  45

Ala Ile Ala Glu Lys Ala Glu Gln Asp Leu Arg Asp Leu Leu Ser Val
    50                  55                  60

Pro Ser Asn Tyr Lys Val Leu Phe Leu Gln Gly Gly Ala Ser Gln Gln
65                  70                  75                  80

Phe Ala Glu Ile Pro Leu Asn Leu Leu Pro Glu Asn Gly Thr Ala Asp
                85                  90                  95

Tyr Ile Glu Thr Gly Ile Trp Ser Lys Lys Ala Ile Glu Glu Ala Arg
            100                 105                 110

Arg Phe Gly Asn Val Asn Val Ala Ala Thr Ala Lys Pro Tyr Asp Tyr
        115                 120                 125

Leu Ala Ile Pro Gly Gln Asn Glu Trp Asn Leu Thr Lys Asn Ala Ala
    130                 135                 140

Tyr Val His Tyr Ala Ser Asn Glu Thr Ile Gly Gly Leu Gln Phe Asp
145                 150                 155                 160

Trp Val Pro Gln Thr Gly Asp Val Pro Leu Val Val Asp Met Ser Ser
                165                 170                 175

Asp Ile Leu Ser Arg Pro Ile Asp Val Ser Gln Phe Gly Leu Ile Tyr
            180                 185                 190

Ala Gly Ala Gln Lys Asn Ile Gly Pro Ser Gly Leu Val Val Val Ile
        195                 200                 205

Val Arg Glu Asp Leu Leu Gly His Ala Arg Ser Ser Cys Pro Thr Met
    210                 215                 220

Leu Asp Tyr Lys Val Ser Ala Asp Asn Gly Ser Met Tyr Asn Thr Pro
225                 230                 235                 240

Ala Thr Tyr Ser Trp Tyr Leu Ser Gly Leu Val Phe Glu Trp Leu Lys
                245                 250                 255

Glu Gln Gly Gly Val Glu Ala Met Glu Gln Arg Asn Arg Ala Lys Lys
            260                 265                 270

Asp Arg Leu Tyr Gly Phe Ile Asp Arg Ser Glu Phe Tyr Thr Asn Pro
        275                 280                 285

Ile Ser Val Asn Ala Arg Ser Trp Met Asn Val Pro Phe Arg Leu Ala
    290                 295                 300

Asp Glu Arg Leu Asp Lys Ala Phe Leu Ala Gly Ala Asp Ala Arg Gly
305                 310                 315                 320

Leu Leu Asn Leu Lys Gly His Arg Ser Val Gly Gly Met Arg Ala Ser
                325                 330                 335

Ile Tyr Asn Ala Leu Gly Leu Glu Ala Val Glu Ala Leu Val Gly Tyr
            340                 345                 350

Met Ala Glu Phe Glu Lys Glu His Gly
        355                 360


<210> SEQ ID NO 48
<211> LENGTH: 361
<212> TYPE: PRT
<213> ORGANISM: Pseudomonas aeruginosa

<400> SEQUENCE: 48

Met Ser Lys Arg Ala Phe Asn Phe Cys Ala Gly Pro Ala Ala Leu Pro
1               5                   10                  15

Asp Ala Val Leu Gln Arg Ala Gln Ala Glu Leu Leu Asp Trp Arg Gly
            20                  25                  30

Lys Gly Leu Ser Val Met Glu Met Ser His Arg Ser Asp Asp Tyr Val
        35                  40                  45
```

```
Ala Ile Ala Ser Lys Ala Glu Gln Asp Leu Arg Asp Leu Leu Asp Ile
    50                  55                  60

Pro Ser Asp Tyr Lys Val Leu Phe Leu Gln Gly Gly Ala Ser Gln Gln
65                  70                  75                  80

Phe Ala Glu Ile Pro Leu Asn Leu Leu Pro Glu Asp Gly Val Ala Asp
                85                  90                  95

Tyr Ile Asp Thr Gly Ile Trp Ser Lys Lys Ala Ile Glu Glu Ala Arg
            100                 105                 110

Arg Tyr Gly Thr Val Asn Val Ala Ala Ser Ala Lys Glu Tyr Asp Tyr
        115                 120                 125

Phe Ala Ile Pro Gly Gln Asn Glu Trp Thr Leu Thr Lys Asp Ala Ala
    130                 135                 140

Tyr Val His Tyr Ala Ser Asn Glu Thr Ile Gly Gly Leu Glu Phe Asp
145                 150                 155                 160

Trp Ile Pro Glu Thr Gly Asp Val Pro Leu Val Thr Asp Met Ser Ser
                165                 170                 175

Asp Ile Leu Ser Arg Pro Leu Asp Val Ser Arg Phe Gly Leu Ile Tyr
            180                 185                 190

Ala Gly Ala Gln Lys Asn Ile Gly Pro Ser Gly Leu Val Val Val Ile
        195                 200                 205

Val Arg Glu Asp Leu Leu Gly Arg Ala Arg Ser Val Cys Pro Thr Met
    210                 215                 220

Leu Asn Tyr Lys Ile Ala Ala Asp Asn Gly Ser Met Tyr Asn Thr Pro
225                 230                 235                 240

Ala Thr Tyr Ser Trp Tyr Leu Ser Gly Leu Val Phe Glu Trp Leu Lys
                245                 250                 255

Glu Gln Gly Gly Val Thr Ala Met Glu Gln Arg Asn Arg Ala Lys Lys
            260                 265                 270

Asp Leu Leu Tyr Lys Thr Ile Asp Ala Ser Asp Phe Tyr Thr Asn Pro
        275                 280                 285

Ile Gln Pro Ser Ala Arg Ser Trp Met Asn Val Pro Phe Arg Leu Ala
    290                 295                 300

Asp Glu Arg Leu Asp Lys Pro Phe Leu Glu Gly Ala Glu Ala Arg Gly
305                 310                 315                 320

Leu Leu Asn Leu Lys Gly His Arg Ser Val Gly Gly Met Arg Ala Ser
                325                 330                 335

Ile Tyr Asn Ala Leu Gly Leu Asp Ala Val Glu Ala Leu Val Ala Tyr
            340                 345                 350

Met Ala Glu Phe Glu Lys Glu His Gly
        355                 360


<210> SEQ ID NO 49
<211> LENGTH: 361
<212> TYPE: PRT
<213> ORGANISM: Pseudomonas fluorescens

<400> SEQUENCE: 49

Met Ser Lys Arg Ala Tyr Asn Phe Cys Ala Gly Pro Ala Ala Leu Pro
1               5                   10                  15

Glu Ala Val Leu Gln Arg Ala Gln Gly Glu Leu Leu Asp Trp His Gly
            20                  25                  30

Lys Gly Leu Ser Val Met Glu Met Ser His Arg Ser Asp Glu Phe Val
        35                  40                  45

Ser Ile Ala Thr Lys Ala Glu Gln Asp Leu Arg Asp Leu Leu Gly Ile
    50                  55                  60
```

```
Pro Ser His Tyr Lys Val Leu Phe Leu Gln Gly Gly Ala Ser Gln Gln
65                  70                  75                  80

Phe Ala Gln Ile Pro Leu Asn Leu Leu Pro Glu Asp Gly Thr Ala Asp
                85                  90                  95

Tyr Ile Asp Thr Gly Ile Trp Gly Gln Lys Ala Ile Glu Glu Ala Ser
            100                 105                 110

Arg Tyr Gly His Val Asn Val Ala Gly Thr Ala Lys Pro Tyr Asp Tyr
        115                 120                 125

Phe Ala Ile Pro Gly Gln Asn Glu Trp Lys Leu Ser Lys Asp Ala Ala
    130                 135                 140

Tyr Val His Tyr Val Ala Asn Glu Thr Ile Gly Gly Leu Glu Phe Asp
145                 150                 155                 160

Trp Val Pro Glu Val Gly Asp Val Pro Leu Val Cys Asp Met Ser Ser
                165                 170                 175

Asp Ile Leu Ser Arg Pro Ile Asp Val Ser Lys Tyr Gly Met Ile Tyr
            180                 185                 190

Ala Gly Ala Gln Lys Asn Ile Gly Pro Ser Gly Ile Leu Val Asn Ile
        195                 200                 205

Ile Arg Glu Asp Leu Leu Gly Arg Ala Arg Ser Leu Cys Pro Thr Met
    210                 215                 220

Leu Asn Tyr Lys Val Ala Ala Asp Asn Gly Ser Met Tyr Asn Thr Pro
225                 230                 235                 240

Pro Ala Phe Ala Trp Tyr Leu Ser Gly Leu Val Phe Glu Trp Leu Lys
                245                 250                 255

Glu Gln Gly Gly Val Ala Ala Met Gly Lys Leu Asn Glu Glu Lys Lys
            260                 265                 270

Arg Thr Leu Tyr Asp Phe Ile Asp Ala Ser Gly Leu Tyr Ser Asn Pro
        275                 280                 285

Ile Asn Leu Thr Asp Arg Ser Trp Met Asn Val Pro Phe Arg Leu Ala
    290                 295                 300

Asp Asp Arg Leu Asp Lys Pro Phe Leu Ala Gly Ala Asp Glu Arg Gly
305                 310                 315                 320

Leu Leu Asn Leu Lys Gly His Arg Ser Val Gly Gly Met Arg Ala Ser
                325                 330                 335

Ile Tyr Asn Ala Val Asp Ile Asn Ala Ile Lys Ala Leu Ile Ala Tyr
            340                 345                 350

Met Ala Glu Phe Glu Lys Glu His Gly
        355                 360


<210> SEQ ID NO 50
<211> LENGTH: 398
<212> TYPE: PRT
<213> ORGANISM: Ralstonia eutropha

<400> SEQUENCE: 50

Met Gly Asn Thr Gly Ser His Phe Ser Ile Pro Arg Leu Met Asn Asp
1               5                   10                  15

Pro Gln Asn Pro Ala Leu Ala Gly Met Met Gln Arg Ala Leu Ala Glu
            20                  25                  30

Arg Val Tyr Asn Phe Ser Pro Gly Pro Ala Ala Leu Pro Ala Glu Val
        35                  40                  45

Leu Gln Gln Ala Ala Glu Glu Met Leu Ser Trp His Gly Thr Gly Val
    50                  55                  60

Ser Val Met Glu Met Ser His Arg Ser Arg Glu Phe Glu Ser Ile His
```

```
65                  70                  75                  80

Asn Glu Ala Ile Ala Asp Leu Arg Glu Leu Leu His Ile Pro Ala Asn
                85                  90                  95

Phe Lys Val Leu Phe Leu Gln Gly Gly Ala Ile Gly Glu Asn Ala Ile
            100                 105                 110

Val Pro Leu Asn Leu Met Arg Leu Arg Ser Ala Glu Gln Pro Lys Ala
        115                 120                 125

Asp Phe Val Val Thr Gly Thr Trp Ser Val Lys Thr Glu Gln Glu Ala
    130                 135                 140

Arg Arg Tyr Gly Ala Val Asn Ile Ala Ala Thr Ser Glu Ala Glu Lys
145                 150                 155                 160

Phe His Arg Ile Pro Asp Ile Ala Asp Trp Lys Leu Ser Asp Asp Ala
                165                 170                 175

Gly Tyr Val His Leu Cys Thr Asn Glu Thr Ile Val Gly Val Glu Phe
            180                 185                 190

Gln Asp Ile Pro Asp Ile Gly Gln Val Lys Gly Asp Arg Val Val Val
        195                 200                 205

Ala Asp Ala Ser Ser His Ile Leu Ser Arg Pro Ile Asp Trp Ser Arg
    210                 215                 220

Val Gln Val Val Tyr Gly Gly Ala Gln Lys Asn Ile Gly Pro Ala Gly
225                 230                 235                 240

Val Thr Ile Val Ile Val Arg Asp Asp Leu Ile Gly His Ala His Pro
                245                 250                 255

Leu Cys Pro Ser Ala Phe Asn Trp Arg Leu Val Ala Glu His Asn Ser
            260                 265                 270

Met Tyr Asn Thr Pro Pro Thr Tyr Ala Ile Tyr Ile Ala Gly Leu Val
        275                 280                 285

Phe Lys Trp Leu Lys Arg Gln Gly Gly Val Pro Ala Ile Glu Gln Arg
    290                 295                 300

Asn Ile Ala Lys Ala Ser Ala Leu Tyr Asn Tyr Leu Asp Gln Ser Asp
305                 310                 315                 320

Phe Tyr Arg Asn Glu Ile His Pro Ser Cys Arg Ser Arg Met Asn Val
                325                 330                 335

Pro Phe Phe Leu Gly Asp Glu Ser Arg Asn Glu Val Phe Leu Gln Gln
            340                 345                 350

Ala Arg Ala Asn Gly Leu Val Gln Leu Lys Gly His Lys Thr Val Gly
        355                 360                 365

Gly Met Arg Ala Ser Ile Tyr Asn Ala Met Pro Leu Glu Gly Val Met
    370                 375                 380

Ala Leu Val Asp Phe Met Arg Glu Phe Glu Arg Thr Ser Ala
385                 390                 395


<210> SEQ ID NO 51
<211> LENGTH: 422
<212> TYPE: PRT
<213> ORGANISM: Arabidopsis thaliana

<400> SEQUENCE: 51

Met Ala Ala Ser Thr Asn Ser Phe Leu Ile Gly Asn Gln Thr Gln Ile
1               5                   10                  15

Pro Ser Leu Lys Pro Lys Ser Ile Ser Gln Ser Phe Ile His Phe Thr
            20                  25                  30

Lys Pro Asn Thr Ile Asn Leu Thr Thr Arg Thr Lys Ser Val Ser Ile
        35                  40                  45
```

```
Arg Cys Ala Ser Ala Ser Thr Thr Val Gly Ser Glu Gln Arg Val Ile
    50                  55                  60

Asn Phe Ala Ala Gly Pro Ala Ala Leu Pro Glu Asn Val Leu Leu Lys
65                  70                  75                  80

Ala Gln Ser Asp Leu Tyr Asn Trp Arg Gly Ser Gly Met Ser Val Met
                85                  90                  95

Glu Met Ser His Arg Gly Lys Glu Phe Leu Ser Ile Ile Gln Lys Ala
            100                 105                 110

Glu Ser Asp Leu Arg Gln Leu Leu Glu Ile Pro Ser Glu Tyr Ser Val
        115                 120                 125

Leu Phe Leu Gln Gly Gly Ala Thr Thr Gln Phe Ala Ala Leu Pro Leu
    130                 135                 140

Asn Leu Cys Lys Ser Asp Asp Ser Val Asp Tyr Ile Val Thr Gly Ser
145                 150                 155                 160

Trp Gly Asp Lys Ala Phe Lys Glu Ala Lys Lys Tyr Cys Asn Pro Lys
                165                 170                 175

Val Ile Trp Ser Gly Lys Ser Glu Lys Tyr Thr Lys Val Pro Thr Phe
            180                 185                 190

Asp Gly Leu Glu Gln Ser Ser Asp Ala Lys Tyr Leu His Ile Cys Ala
        195                 200                 205

Asn Glu Thr Ile His Gly Val Glu Phe Lys Asp Tyr Pro Leu Val Glu
    210                 215                 220

Asn Pro Asp Gly Val Leu Ile Ala Asp Met Ser Ser Asn Phe Cys Ser
225                 230                 235                 240

Lys Pro Val Asp Val Ser Lys Phe Gly Val Ile Tyr Ala Gly Ala Gln
                245                 250                 255

Lys Asn Val Gly Pro Ser Gly Val Thr Ile Val Ile Ile Arg Lys Asp
            260                 265                 270

Leu Ile Gly Asn Ala Arg Asp Ile Thr Pro Val Met Leu Asp Tyr Lys
        275                 280                 285

Ile His Asp Glu Asn Ser Ser Leu Tyr Asn Thr Pro Pro Cys Phe Gly
    290                 295                 300

Ile Tyr Met Cys Gly Leu Val Phe Asp Asp Leu Leu Glu Gln Gly Gly
305                 310                 315                 320

Leu Lys Glu Val Glu Lys Lys Asn Gln Arg Lys Ala Glu Leu Leu Tyr
                325                 330                 335

Asn Ala Ile Asp Glu Ser Arg Gly Phe Phe Arg Cys Pro Val Glu Lys
            340                 345                 350

Ser Val Arg Ser Leu Met Asn Val Pro Phe Thr Leu Glu Lys Ser Glu
        355                 360                 365

Leu Glu Ala Glu Phe Ile Lys Glu Ala Ala Lys Glu Lys Met Val Gln
    370                 375                 380

Leu Lys Gly His Arg Ser Val Gly Gly Met Arg Ala Ser Ile Tyr Asn
385                 390                 395                 400

Ala Met Pro Leu Ala Gly Val Glu Lys Leu Val Ala Phe Met Lys Asp
                405                 410                 415

Phe Gln Ala Arg His Ala
            420
```

```
<210> SEQ ID NO 52
<211> LENGTH: 360
<212> TYPE: PRT
<213> ORGANISM: Clostridium beijerinckii

<400> SEQUENCE: 52
```

```
Met Ser Arg Val Tyr Asn Phe Ser Ala Gly Pro Ala Val Leu Pro Glu
1               5                   10                  15

Ser Val Leu Arg Glu Ala Ala Gly Glu Met Leu Asp Tyr Lys Gly Thr
            20                  25                  30

Gly Met Ser Val Met Glu Met Ser His Arg Ser Lys Ala Phe Glu Glu
        35                  40                  45

Ile Ile Thr Asp Ala Glu Lys Thr Leu Arg Glu Leu Met Asn Ile Pro
    50                  55                  60

Asp Asn Tyr Lys Val Leu Phe Leu Gln Gly Gly Ala Ser Gln Gln Phe
65                  70                  75                  80

Ala Met Ile Pro Met Asn Leu Met Lys Asn Lys Val Val Asp His Ile
                85                  90                  95

Ile Thr Gly Gln Trp Ala Lys Lys Ala Ala Ser Glu Ala Lys Ile Phe
            100                 105                 110

Gly Lys Val Asn Ile Leu Ala Ser Ser Glu Asp Lys Thr Phe Ser Tyr
        115                 120                 125

Ile Pro Asp Leu Lys Asp Leu Lys Val Ser Glu Asp Ala Asp Tyr Val
    130                 135                 140

Tyr Ile Cys His Asn Asn Thr Ile Tyr Gly Thr Thr Tyr Lys Glu Leu
145                 150                 155                 160

Pro Asn Val Gly Asp Lys Ile Leu Val Ala Asp Met Ser Ser Asp Phe
                165                 170                 175

Leu Ser Glu Pro Val Asp Val Ser Lys Tyr Gly Leu Ile Phe Ala Gly
            180                 185                 190

Val Gln Lys Asn Ala Gly Pro Ala Gly Val Val Val Val Ile Ile Arg
        195                 200                 205

Glu Asp Leu Ile Thr Glu Asp Val Leu Pro Gly Thr Pro Thr Met Leu
    210                 215                 220

Arg Tyr Lys Val His Ala Asp Asn Lys Ser Leu Tyr Asn Thr Pro Pro
225                 230                 235                 240

Ala Tyr Gly Ile Tyr Ile Cys Gly Lys Val Phe Lys Trp Val Lys Asn
                245                 250                 255

Lys Gly Gly Leu Glu Ala Met Lys Lys Ile Asn Glu Glu Lys Ala Ser
            260                 265                 270

Ile Leu Tyr Asp Phe Leu Asp Ser Ser Ser Met Phe Lys Gly Thr Val
        275                 280                 285

Val Lys Lys Asp Arg Ser Leu Met Asn Val Pro Phe Val Thr Gly Ser
    290                 295                 300

Asp Glu Leu Asp Ala Lys Phe Val Lys Glu Ala Lys Ala Val Gly Phe
305                 310                 315                 320

Glu Asn Leu Lys Gly His Arg Thr Val Gly Gly Met Arg Ala Ser Ile
                325                 330                 335

Tyr Asn Ala Met Pro Ile Glu Gly Val Lys Asp Leu Val Glu Phe Met
            340                 345                 350

Arg Lys Phe Glu Glu Asp Asn Lys
        355                 360
```

<210> SEQ ID NO 53
<211> LENGTH: 365
<212> TYPE: PRT
<213> ORGANISM: Lactococcus lactis

<400> SEQUENCE: 53

```
Met Ile Tyr Asn Phe Gly Ala Gly Pro Ser Val Leu Pro Lys Glu Val
```

```
1               5                   10                  15

Leu Lys Lys Val Gln Glu Glu Leu Leu Asp Phe Glu Lys Ser Gly Met
            20                  25                  30

Ser Val Met Glu Ile Ser His Arg Ser Lys Ala Phe Gln Lys Val Ile
        35                  40                  45

Asp Glu Ala Glu Asn Asp Leu Arg Asp Leu Met Ser Ile Pro Gln Asn
    50                  55                  60

Tyr Lys Ile Leu Phe Leu Gln Gly Gly Ala Ser Ser Gln Phe Ser Met
65                  70                  75                  80

Val Pro Met Asn Leu Ala Ile Gly Lys Lys Ala Tyr Tyr Asn Ile Ser
                85                  90                  95

Gly Ala Phe Gly Glu Lys Ala Tyr Asp Glu Ala Val Lys Leu Ser His
            100                 105                 110

Phe Leu Asp Leu Met Ala Ile Ser Leu Gly Ser Thr Lys Lys Asp Asn
        115                 120                 125

Tyr Asn His Leu Leu Lys Ile Asp Lys Ser Lys Ile Asp Glu Lys Asn
    130                 135                 140

Gly Ala Tyr Leu His Leu Thr Thr Asn Asn Thr Ile Glu Gly Thr Ser
145                 150                 155                 160

Ile Phe Pro Glu Asn Leu Pro Glu Phe Ala Ser Leu Pro Leu Val Ala
                165                 170                 175

Asp Met Ser Ser Asn Ile Leu Ala Val Asp Tyr Asp Val Ser Lys Phe
            180                 185                 190

Gly Leu Ile Tyr Ala Gly Ala Gln Lys Asn Leu Gly Ile Ala Gly Leu
        195                 200                 205

Thr Ile Val Ile Ile Arg Glu Asp Leu Leu Asn Glu Ala Glu Ser Leu
    210                 215                 220

Ser Ser Met Met Asp Tyr Gln Ile Leu Val Glu Asn Gly Ser Met Tyr
225                 230                 235                 240

Asn Thr Pro Pro Thr Phe Ala Ile Tyr Val Ala Gly Leu Val Phe Lys
                245                 250                 255

Trp Val Lys Ala Gln Gly Gly Val Lys Lys Leu Glu Glu Met Asn Gln
            260                 265                 270

Arg Lys Ala Gln Leu Leu Tyr Asp Leu Ile Asp Gln Ser Asp Phe Tyr
        275                 280                 285

Gln Asn Pro Ile Lys Asn Lys Asp Glu Arg Ser Ile Cys Asn Val Val
    290                 295                 300

Phe Thr Ser Pro Ser Gln Glu Leu Asp Glu Leu Phe Thr Gln Lys Ala
305                 310                 315                 320

Glu Glu Lys Gly Phe Lys Ser Leu Lys Gly His Arg Ser Val Gly Gly
                325                 330                 335

Met Arg Ala Ser Ile Tyr Asn Ala Phe Pro Leu Glu Gly Val Val Glu
            340                 345                 350

Leu Val Lys Phe Met Lys Glu Phe Glu Glu Gly Tyr Lys
        355                 360                 365


<210> SEQ ID NO 54
<211> LENGTH: 359
<212> TYPE: PRT
<213> ORGANISM: Bacillus subtilis

<400> SEQUENCE: 54

Met Glu Arg Thr Thr Asn Phe Asn Ala Gly Pro Ala Ala Leu Pro Leu
1               5                   10                  15
```

```
Glu Val Leu Gln Lys Ala Gln Lys Glu Phe Ile Asp Phe Asn Glu Ser
            20                  25                  30

Gly Met Ser Val Met Glu Leu Ser His Arg Ser Lys Glu Tyr Glu Ala
        35                  40                  45

Val His Gln Lys Ala Lys Ser Leu Leu Ile Glu Leu Met Gly Ile Pro
    50                  55                  60

Glu Asp Tyr Asp Ile Leu Phe Leu Gln Gly Gly Ala Ser Leu Gln Phe
65                  70                  75                  80

Ser Met Leu Pro Met Asn Phe Leu Thr Pro Glu Lys Thr Ala His Phe
                85                  90                  95

Val Met Thr Gly Ala Trp Ser Glu Lys Ala Leu Ala Glu Thr Lys Leu
            100                 105                 110

Phe Gly Asn Thr Ser Ile Thr Ala Thr Ser Glu Thr Asp Asn Tyr Ser
        115                 120                 125

Tyr Ile Pro Glu Val Asp Leu Thr Asp Val Lys Asp Gly Ala Tyr Leu
    130                 135                 140

His Ile Thr Ser Asn Asn Thr Ile Phe Gly Thr Gln Trp Gln Glu Phe
145                 150                 155                 160

Pro Asn Ser Pro Ile Pro Leu Val Ala Asp Met Ser Ser Asp Ile Leu
                165                 170                 175

Ser Arg Lys Ile Asp Val Ser Lys Phe Asp Val Ile Tyr Gly Gly Ala
            180                 185                 190

Gln Lys Asn Leu Gly Pro Ser Gly Val Thr Val Val Ile Met Lys Lys
        195                 200                 205

Ser Trp Leu Gln Asn Glu Asn Ala Asn Val Pro Lys Ile Leu Lys Tyr
    210                 215                 220

Ser Thr His Val Lys Ala Asp Ser Leu Tyr Asn Thr Pro Pro Thr Phe
225                 230                 235                 240

Ala Ile Tyr Met Leu Ser Leu Val Leu Glu Trp Leu Lys Glu Asn Gly
                245                 250                 255

Gly Val Glu Ala Val Glu Gln Arg Asn Glu Gln Lys Ala Gln Val Leu
            260                 265                 270

Tyr Ser Cys Ile Asp Glu Ser Asn Gly Phe Tyr Lys Gly His Ala Arg
        275                 280                 285

Lys Asp Ser Arg Ser Arg Met Asn Val Thr Phe Thr Leu Arg Asp Asp
    290                 295                 300

Glu Leu Thr Lys Thr Phe Val Gln Lys Ala Lys Asp Ala Lys Met Ile
305                 310                 315                 320

Gly Leu Gly Gly His Arg Ser Val Gly Gly Cys Arg Ala Ser Ile Tyr
                325                 330                 335

Asn Ala Val Ser Leu Glu Asp Cys Glu Lys Leu Ala Ala Phe Met Lys
            340                 345                 350

Lys Phe Gln Gln Glu Asn Glu
        355
```

<210> SEQ ID NO 55
<211> LENGTH: 395
<212> TYPE: PRT
<213> ORGANISM: Saccharomyces cerevisiae

<400> SEQUENCE: 55

```
Met Ser Leu Glu Arg Glu Glu Pro Gln His Phe Gly Ala Gly Pro Ala
1               5                   10                  15

Gln Met Pro Thr Pro Val Leu Gln Gln Ala Ala Lys Asp Leu Ile Asn
            20                  25                  30
```

```
Phe Asn Asp Ile Gly Leu Gly Ile Gly Glu Ile Ser His Arg Ser Lys
        35                  40                  45

Asp Ala Thr Lys Val Ile Glu Asp Ser Lys Lys His Leu Ile Glu Leu
    50                  55                  60

Leu Asn Ile Pro Asp Thr His Glu Val Phe Tyr Leu Gln Gly Gly Gly
65                  70                  75                  80

Thr Thr Gly Phe Ser Ser Val Ala Thr Asn Leu Ala Ala Ala Tyr Val
                85                  90                  95

Gly Lys His Gly Lys Ile Ala Pro Ala Gly Tyr Leu Val Thr Gly Ser
            100                 105                 110

Trp Ser Gln Lys Ser Phe Glu Glu Ala Lys Arg Leu His Val Pro Ala
        115                 120                 125

Glu Val Ile Phe Asn Ala Lys Asp Tyr Asn Asn Gly Lys Phe Gly Lys
    130                 135                 140

Ile Pro Asp Glu Ser Leu Trp Glu Asp Lys Ile Lys Gly Lys Ala Phe
145                 150                 155                 160

Ser Tyr Val Tyr Leu Cys Glu Asn Glu Thr Val His Gly Val Glu Trp
                165                 170                 175

Pro Glu Leu Pro Lys Cys Leu Val Asn Asp Pro Asn Ile Glu Ile Val
            180                 185                 190

Ala Asp Leu Ser Ser Asp Ile Leu Ser Arg Lys Ile Asp Val Ser Gln
        195                 200                 205

Tyr Gly Val Ile Met Ala Gly Ala Gln Lys Asn Ile Gly Leu Ala Gly
    210                 215                 220

Leu Thr Leu Tyr Ile Ile Lys Lys Ser Ile Leu Lys Asn Ile Ser Gly
225                 230                 235                 240

Ala Ser Asp Glu Thr Leu His Glu Leu Gly Val Pro Ile Thr Pro Ile
                245                 250                 255

Ala Phe Asp Tyr Pro Thr Val Val Lys Asn Asn Ser Ala Tyr Asn Thr
            260                 265                 270

Ile Pro Ile Phe Thr Leu His Val Met Asp Leu Val Phe Gln His Ile
        275                 280                 285

Leu Lys Lys Gly Gly Val Glu Ala Gln Gln Ala Glu Asn Glu Glu Lys
    290                 295                 300

Ala Lys Ile Leu Tyr Glu Ala Leu Asp Ala Asn Ser Asp Phe Tyr Asn
305                 310                 315                 320

Val Pro Val Asp Pro Lys Cys Arg Ser Lys Met Asn Val Val Phe Thr
                325                 330                 335

Leu Lys Lys Asp Gly Leu Asp Asp Gln Phe Leu Lys Glu Ala Ala Ala
            340                 345                 350

Arg His Leu Thr Gly Leu Lys Gly His Arg Ser Val Gly Gly Phe Arg
        355                 360                 365

Ala Ser Ile Tyr Asn Ala Leu Ser Val Lys Ala Val Gln Asn Leu Val
    370                 375                 380

Asp Phe Ile Lys Glu Phe Ala Glu Lys Asn Ala
385                 390                 395
```

MUTANT PHOSPHOSERINE AMINOTRANSFERASE FOR THE CONVERSION OF HOMOSERINE INTO 4-HYDROXY-2-KETOBUTYRATE

REFERENCE TO SEQUENCE LISTING SUBMITTED VIA EFS-WEB

This application includes an electronically submitted sequence listing in .txt format. The .txt file contains a sequence listing entitled "3493_0721PUS1_Substitute_Sequence_Listing.txt" created on Jun. 14, 2021 and is 142,747 bytes in size. The sequence listing contained in this .txt file is part of the specification and is hereby incorporated by reference herein in its entirety.

DOMAIN OF THE INVENTION

The present invention relates to a method for the production of derivatives of 4-hydroxy-2-ketobutyrate chosen among 1,3-propanediol, 3-hydroxypropionaldehyde, 3-hydroxypropionate and 2,4-dihydroxybutyrate by culturing a genetically modified microorganism for the production of the desired derivative of 4-hydroxy-2-ketobutyrate, the microorganism further comprising a gene coding for a mutant phosphoserine aminotransferase having an improved L-homoserine aminotransferase activity converting by transamination L-homoserine into 4-hydroxy-2-ketobutyrate. The invention also concerns said genetically modified microorganism.

BACKGROUND

Methods for the biosynthesis of derivatives of 4-hydroxy-2-ketobutyrate by fermentation, where the microorganism metabolically transforms a simple source of carbon into derivatives of 4-hydroxy-2-ketobutyrate are known in the art. Such derivatives of 4-hydroxy-2-ketobutyrate are in particular 1,3-propanediol, 3-hydroxypropionaldehyde, 3-hydroxypropionate and 2,4-dihydroxybutyrate. The latter is a precursor of methionine hydroxy analogue (MHA).

Preparation of 1,3-propanediol from 4-hydroxy-2-ketobutyrate by fermentation is well disclosed in WO 2010/076324 and WO 2012/004247 patent applications which are incorporated herein by reference.

Production of 3-hydroxypropionaldehyde from 4-hydroxy-2-ketobutyrate by fermentation is well disclosed in WO 2010/076324, WO 2012/001003 and WO 2012/004247 patent applications which are incorporated herein by reference.

Preparation of 3-hydroxypropionate from 4-hydroxy-2-ketobutyrate by fermentation is well disclosed in WO 2012/001003 patent application which are incorporated herein by reference.

Preparation of 2,4-dihydroxybutyrate from 4-hydroxy-2-ketobutyrate by fermentation is well disclosed in WO 2014/009435, WO2016/162442 patent application incorporated herein by reference.

In these pathways of production of 1,3-propanediol, 3-hydroxypropionaldehyde, 3-hydroxypropionate and 2,4-dihydroxybutyrate, 4-hydroxy-2-ketobutyrate is obtained by the transamination of L-homoserine.

It is particularly known from these applications to improve the metabolic pathway to favour the production of L-homoserine and to limit the usual metabolic pathways using L-homoserine as a substrate, like for its conversion into L-threonine.

In patent applications WO 2010/076324, WO 2012/001003, WO 2012/004247 and WO2014/009435, conversion of 4-hydroxy-2-ketobutyrate into 1,3-propanediol, 3-hydroxypropionaldehyde, 3-hydroxypropionate and into 2,4-dihydroxybutyrate are well described. The pathway for 1,3-propanediol production from 4-hydroxy-2-ketobutyrate comprises two steps after the conversion of L-homoserine into 4-hydroxy-2-ketobutyrate:

- a first step of converting 4-hydroxy-2-ketobutyrate into 3-hydroxypropionaldehyde, and
- a second step of converting 3-hydroxypropionaldehyde into 1,3-propanediol.

The pathway for 3-hydroxypropionate production from 4-hydroxy-2-ketobutyrate comprises two steps after the conversion of L-homoserine into 4-hydroxy-2-ketobutyrate:

- a first step of converting 4-hydroxy-2-ketobutyrate into 3-hydroxypropionaldehyde, and
- a second step of converting 3-hydroxypropionaldehyde into 3-hydroxypropionate.

For 2,4-dihydroxybutyrate production, L-homoserine is converting into 4-hydroxy-2-ketobutyrate and then 4-hydroxy-2-ketobutyrate is converting into 2,4-dihydroxybutyrate as disclosed in patent application WO2014/009435 and WO2016/162442.

Even if main steps of these pathways are well described, the step of converting L-homoserine into 4-hydroxy-2-ketobutyrate is a limiting step.

The inventors have now found that this step can be improved by using a mutant phosphoserine aminotransferase having an improved L-homoserine aminotransferase activity converting L-homoserine into 4-hydroxy-2-ketobutyrate by transamination.

BRIEF DESCRIPTION OF THE INVENTION

The present invention concerns a genetically modified microorganism for the production of a derivative of 4-hydroxy-2-ketobutyrate selected in the group consisting of 1,3-propanediol, 3-hydroxypropionaldehyde, 3-hydroxypropionate and 2,4-dihydroxybutyrate, wherein said genetically modified microorganism further comprises a gene coding for a mutant phosphoserine aminotransferase having an improved L-homoserine aminotransferase activity converting by transamination L-homoserine into 4-hydroxy-2-ketobutyrate and wherein said mutant phosphoserine aminotransferase comprises at least a mutation where amino acid R (Arg) at position 42, by reference to *E. coli* phosphoserine aminotransferase of SEQ ID NO: 2, is replaced by a non-polar amino acid.

The genetically modified microorganism according to the present invention may further comprise a mutation where amino acid R (Arg) at position 77, by reference to *E. coli* phosphoserine aminotransferase of SEQ ID NO: 2, is replaced by a polar uncharged or a non-polar amino acid.

The genetically modified microorganism is selected among the group consisting of bacterium, yeast and fungus, particularly selected among Enterobacteriaceae, Clostridiaceae, Bacillaceae, Streptomycetaceae and Corynebacteriaceae. In a preferred embodiment, the genetically modified microorganism is *Escherichia coli*.

The present invention also concerns a method for the production of derivatives of 4-hydroxy-2-ketobutyrate selected in the group consisting of 1,3-propanediol, 3-hydroxypropionaldehyde, 3-hydroxypropionate and 2,4-dihydroxybutyrate, by culturing a genetically modified microorganism for the production of the desired derivative of 4-hydroxy-2-ketobutyrate and further comprising a gene coding for a mutant phosphoserine aminotransferase having an improved L-homoserine aminotransferase activity converting by transamination L-homoserine into 4-hydroxy-2-ketobutyrate as described above.

DRAWINGS

FIG. 1 represents a schematic view of molecular modeling of the active sites of *E. coli* phosphoserine aminotransferase protein.

FIGS. 2 A and 2 B represent alignments of several phosphoserine aminotransferase proteins from *Escherichia* (SEQ ID NO: 2); *Citrobacter* (SEQ ID NO: 43); *Enterobacter* (SEQ ID NO: 44); *Pectobacterium* (SEQ ID NO: 45); *Dickeya* (SEQ ID NO: 46); Pseudo_*Putida* (SEQ ID NO: 47); Pseudo_*Aeruginosa* (SEQ ID NO: 48); Pseudo-*Fluorescens* (SEQ ID NO: 49); *Ralstonia* (SEQ ID NO: 50); *Arabidopsis* (SEQ ID NO: 51); *Clostridium* (SEQ ID NO: 52); *Lactococcus* (SEQ ID NO: 53); *Bacillus* (SEQ ID NO: 54); and *Saccharomyces* (SEQ ID NO: 55).

DETAILED DESCRIPTION OF THE INVENTION

Before describing the present invention in detail, it is to be understood that this invention is not limited to particularly exemplified methods and may, of course, vary. It is also to be understood that the terminology used herein is for the purpose of describing particular embodiments of the invention only, and is not intended to be limiting, which will be limited only by the appended claims.

All publications, patents and patent applications cited herein, whether supra or infra, are hereby incorporated by reference in their entirety.

Furthermore, the practice of the present invention employs, unless otherwise indicated, conventional microbiological and molecular biological techniques within the skill of the art. Such techniques are well known to the skilled worker, and are explained fully in the literature.

It must be noted that as used herein and in the appended claims, the singular forms "a", "an", and "the" include plural reference unless the context clearly dictates otherwise. Thus, for example, a reference to "a microorganism" includes a plurality of such microorganisms, and a reference to "an endogenous gene" is a reference to one or more endogenous genes, and so forth. Unless defined otherwise, all technical and scientific terms used herein have the same meanings as commonly understood by one of ordinary skill in the art to which this invention belongs. Although any materials and methods similar or equivalent to those described herein can be used to practice or test the present invention, the preferred materials and methods are now described.

In the claims that follow and in the consecutive description of the invention, except where the context requires otherwise due to express language or necessary implication, the word "comprise", "contain", "involve" or "include" or variations such as "comprises", "comprising", "containing", "involved", "includes", "including" are used in an inclusive sense, i.e. to specify the presence of the stated features but not to preclude the presence or addition of further features in various embodiments of the invention.

In a first aspect, the present invention concerns a genetically modified microorganism for the production of a derivative of 4-hydroxy-2-ketobutyrate selected in the group consisting of 1,3-propanediol, 3-hydroxypropionaldehyde, 3-hydroxypropionate and 2,4-dihydroxybutyrate, wherein said genetically modified microorganism further comprises a gene coding for a mutant phosphoserine aminotransferase having an improved L-homoserine aminotransferase activity, converting by transamination L-homoserine into 4-hydroxy-2-ketobutyrate and wherein said mutant phosphoserine aminotransferase comprises at least amino acid R (Arg) at position 42, by reference to *E. coli* phosphoserine aminotransferase of SEQ ID NO: 2, replaced by a non-polar amino acid.

The genetically modified microorganism of the present invention may further comprise mutation where the amino acid R (Arg) at position 77, by reference to *E. coli* phosphoserine aminotransferase of SEQ ID NO: 2, is replaced by a polar uncharged or a non-polar amino acid.

The terms "derivatives of 4-hydroxy-2-ketobutyrate" thus refer to products of conversion of 4-hydroxy-2-ketobutyrate after one or two steps of conversion of 4-hydroxy-2-ketobutyrate.

The term "microorganism", as used herein, refers to a bacterium, yeast or fungus which is not modified artificially. Preferentially, the microorganism is selected among Enterobacteriaceae, Bacillaceae, Corynebacteriaceae, Clostridiaceae, Streptomycetaceae and yeast. More preferentially the microorganism is a species of *Escherichia, Klebsiella, Thermoanaerobacterium, Corynebacterium, Clostridium* or *Saccharomyces*. More preferentially the microorganism is selected among *Escherichia coli, Klebsiella pneumoniae, Thermoanaerobacterium Thermosaccharolyticum, Corynebacterium glutamicum, Clostridium sphenoides* or *Saccharomyces cerevisiae*. Even more preferentially the microorganism of the invention is *Escherichia coli*.

The term "recombinant microorganism" or "genetically modified microorganism", as used herein, refers to a bacterium, yeast or fungus that is not found in nature and is genetically different from its equivalent found in nature. It means it is modified either by introduction or by deletion or by modification of genetic elements. It can also be transformed by forcing the development and evolution of new metabolic pathways by combining directed mutagenesis and evolution under specific selection pressure (see, for example, WO2005/073364 or WO2008/116852).

A microorganism genetically modified for the production of 1,3-propanediol means according to the invention a microorganism comprising a modified metabolic pathway allowing the conversion of a source of carbon into 1,3-propanediol when the microorganism of the invention is cultured on a culture medium comprising said source of carbon as sole source of carbon.

A microorganism genetically modified for the production of 3-hydroxypropionaldehyde means according to the invention a microorganism comprising a modified metabolic pathway allowing the conversion of a source of carbon into 3-hydroxypropionaldehyde when the microorganism of the invention is cultured on a culture medium comprising said source of carbon as sole source of carbon.

A microorganism genetically modified for the production of 3-hydroxypropionate means according to the invention a microorganism comprising a modified metabolic pathway allowing the conversion of a source of carbon into 3-hydroxypropionate when the microorganism of the invention is cultured on a culture medium comprising said source of carbon as sole source of carbon.

A microorganism genetically modified for the production of 2,4-dihydroxybutyrate means according to the invention a microorganism comprising a modified metabolic pathway allowing the conversion of a source of carbon into 2,4-dihydroxybutyrate when the microorganism of the invention is cultured on a culture medium comprising said source of carbon as sole source of carbon.

The term 'transamination' or "aminotransferase activity", as used herein, refers to the transfer of an amine group from one amino acid to an α-keto acid. In the context of the invention the transamination or the aminotransferase activity refers to the transfer of the amine group from L-homoserine to an α-keto-acid which will be converted into an amino acid, in order to form 4-hydroxy-2-ketobutyrate compound. In a preferred embodiment the transamination or the aminotransferase activity refers to the transfer of the amine group from L-homoserine to alpha-ketoglutarate which will be converted into glutamate, in order to form 4-hydroxy-2-ketobutyrate compound.

A microorganism may be modified to express exogenous genes if these genes are introduced into the microorganism with all the elements allowing their expression in the host microorganism. The modification or "transformation" of microorganisms with exogenous DNA is a routine task for those skilled in the art.

A microorganism may be modified to modulate the expression level of an endogenous gene.

The term "endogenous gene" means that the gene was present in the microorganism before any genetic modification. Endogenous genes may be overexpressed by introducing heterologous sequences in addition to, or to replace endogenous regulatory elements, or by introducing one or more supplementary copies of the gene into the chromosome or a plasmid. Endogenous genes may also be modified to modulate their expression and/or activity. For example, mutations may be introduced into the coding sequence to modify the gene product or heterologous sequences may be introduced in addition to or to replace endogenous regulatory elements. Modulation of an endogenous gene may result in the up-regulation and/or enhancement of the activity of the gene product, or alternatively, down regulate and/or lower the activity of the endogenous gene product.

Another way to modulate their expression is to exchange the endogenous promoter of a gene (e.g., wild type promoter) with a stronger or weaker promoter to up or down regulate expression of the endogenous gene. These promoters may be homologous or heterologous. It is well within the ability of the person skilled in the art to select appropriate promoters.

Contrariwise, "exogenous gene" or "heterologous gene" means that the gene was introduced into a microorganism, by means well known by the man skilled in the art whereas this gene is not naturally occurring in the microorganism. Exogenous genes may be integrated into the host chromosome, or be expressed extra-chromosomally by plasmids or vectors. A variety of plasmids, which differ with respect to their origin of replication and their copy number in the cell, are well known in the art. "Overexpression" or "overexpressing" is also used to designate expression of exogenous genes in the microorganisms.

In the context of the invention, the term "homologous gene" is not limited to designate genes having a theoretical common genetic ancestor, but includes genes which may be genetically unrelated that have, none the less, evolved to encode protein which perform similar functions and/or have similar structure. Therefore the term "functional homolog" for the purpose of the present invention relates to the fact that a certain enzymatic activity may not only be provided by a specific protein of defined amino acid sequence, but also by proteins of similar sequence from other (un)related microorganisms.

Using the references given in Uniprot for known protein or in Genbank for known genes, those skilled in the art are able to obtain protein and/or gene sequences and to determine the equivalent genes in other organisms, bacterial strains, yeast, fungi, mammals, plants, etc. This routine work is advantageously done using consensus sequences that can be determined by carrying out sequence alignments with genes derived from other microorganisms and designing degenerate probes to clone the corresponding gene in another organism. These routine methods of molecular biology are well known to those skilled in the art.

The microorganism may also be modified to increase or decrease the activity of one or more proteins.

Increasing an activity can be obtained by improving the protein catalytic efficiency or decreasing protein turnover or decreasing messenger RNA (mRNA) turnover or increasing transcription of the gene or increasing translation of the mRNA.

Improving the protein catalytic efficiency means increasing the kcat and/or decreasing the Km for a given substrate and/or a given cofactor, and/or increasing the Ki for a given inhibitor. kcat, Km and Ki are Michaelis-Menten constants that the man skilled in the art is able to determine (Segel, 1993). Decreasing protein turnover means stabilizing the protein. Methods to improve protein catalytic efficiency and/or decrease protein turnover are well known from the man skilled in the art. Those include rational engineering with sequence and/or structural analysis and directed mutagenesis, as well as random mutagenesis and screening. Mutations can be introduced by site-directed mutagenesis by usual methods like Polymerase Chain Reaction (PCR), or by random mutagenesis techniques, such as use of mutagenic agents (Ultra-Violet rays or chemical agents like nitrosoguanidine (NTG) or ethylmethanesulfonate (EMS)) or use of PCR techniques (DNA shuffling or error-prone PCR). Stabilizing the protein can also be achieved by adding a peptide sequence called "tag" either at the N-terminus or the C-terminus of the protein. Tags are well known from the man skilled in the art. For instance, a Glutathione-S-Transferase (GST) can be used to stabilize a protein.

Decreasing mRNA turnover can be achieved by modifying the gene sequence of the 5'-untranslated region (5'-UTR) and/or the coding region, and/or the 3'-UTR (Carrier and Keasling, 1999).

Increasing transcription of a gene can be achieved by increasing the number of copies of the gene and/or using a promoter leading to a higher level of expression of the gene. "Overexpression" or "overexpressing" is also used to designate increasing transcription of a gene in the microorganisms.

For increasing the number of copies of the gene in the microorganism, the gene is encoded chromosomally or extra-chromosomally. When the gene is located on the chromosome, several copies of the gene can be introduced on the chromosome by methods of recombination, known by the expert in the field (including gene replacement). When the gene is located extra-chromosomally, it may be carried by different types of plasmids that differ with respect to their origin of replication and thus their copy number in the cell. These plasmids are present in the microorganism in 1 to 5 copies, or about 20 copies, or up to 500 copies, depending on the nature of the plasmid: low copy number plasmids with tight replication (e.g. for *E. coli* pSC101, RK2), low copy number plasmids (e.g. for *E. coli* pACYC, pRSF1010) or high copy number plasmids (e.g. for *E. coli* pSK bluescript II).

For using a promoter leading to a high level of expression of the gene the man skilled in the art knows which promoters are the most convenient, for example promoters Ptrc, Ptac, Plac, or the lambda promoter $P_R$ and $P_L$ are widely used. These promoters can be "inducible" by a particular compound or by specific external condition like temperature or light. These promoters may be homologous or heterologous.

Increasing translation of the mRNA can be achieved by modifying the Ribosome Binding Site (RBS). A RBS is a sequence on mRNA that is bound by the ribosome when initiating protein translation. It can be either the 5' cap of a mRNA in eukaryotes, a region 6-7 nucleotides upstream of the start codon AUG in prokaryotes (called the Shine-Dalgarno sequence), or an internal ribosome entry site (IRES) in viruses. By modifying this sequence, it is possible to change the protein translation initiation rate, proportionally alter its production rate, and control its activity inside the cell. The same RBS sequence will not have the same impact according to the nature of the mRNA. It is possible to optimize the strength of a RBS sequence to achieve a targeted translation initiation rate by using the software RBS CALCULATOR (Salis, 2011).

The man skilled in the art knows different means and method to measure ribonucleic acid concentration or protein concentration in the cell including for instance use of Reverse Transcription Polymerase Chain Reaction (RT-PCR) and Real-time Polymerase Chain Reaction (qPCR) to determine ribonucleic acid concentration and use of specific antibody to determine concentration of specific protein.

Decreasing the activity of an enzyme means either decreasing its specific catalytic activity by mutating the gene so as to change the amino acid sequence and/or decreasing concentrations of the protein in the cell by mutating the nucleotidic sequence or by deleting the coding region of the gene.

The man skilled in the art knows different means and method to measure ribonucleic acid concentration or protein concentration in the cell including for instance use of Reverse Transcription Polymerase Chain Reaction (RT-PCR) and Real-time Polymerase Chain Reaction (qPCR) to determine ribonucleic acid concentration and use of specific antibody to determine concentration of specific protein.

Microorganisms genetically modified for the production of derivatives of 4-hydroxy-2-ketobutyrate chosen among 1,3-propanediol, 3-hydroxypropionaldehyde, 3-hydroxypropionate and 2,4-dihydroxybutyrate comprising a metabolic pathway for the conversion of 4-hydroxy-2-ketobutyrate into its desired derivative are known in the art.

In a particular embodiment of the invention, the genetically modified microorganism for the production of the desired derivative of 4-hydroxy-2-ketobutyrate is modified for the production of 1,3-propanediol from 4-hydroxy-2-ketobutyrate. This modified microorganism is particularly described in WO 2010/076324 and WO 2012/004247, incorporated herein by reference.

The metabolic pathway for the conversion of 4-hydroxy-2-ketobutyrate into 1,3-propanediol is preferably a two-steps pathway comprising:

- conversion of 4-hydroxy-2-ketobutyrate into 3-hydroxypropionaldehyde, and
- conversion of 3-hydroxypropionaldehyde into 1,3-propanediol.

Preferably, the genetically modified microorganism is particularly a bacterium modified by expressing at least one gene encoding an enzyme with 2-keto acid decarboxylase activity for the conversion of 4-hydroxy-2-ketobutyrate into 3-hydroxypropionaldehyde, and at least one gene encoding an enzyme with hydroxy aldehyde reductase activity for the conversion of 3-hydroxypropionaldehyde into 1,3-propanediol. Those genes can be exogenous or endogenous, and can be expressed chromosomally or extra-chromosomally.

Genes coding for a 2-keto acid decarboxylase activity are known in the art, including Pdc genes from various species, and more particularly the Pdc1, Pdc5, Pdc6, Aro10 and Thi3 genes from *Saccharomyces cerevisiae*, kivD gene from *Lactococcus lactis*, pdc gene from *Clostridium acetobutylicum*, Pdc2 and Pdc3 genes from *Arabidopsis thaliana*, Pdc1, Pdc2 and Aro10 genes from *Pichia stipitis*; pdc gene from *Zymomonas mobilis*. The first subunit of the 2-ketoglutarate decarboxylase complex, encoded by the gene sucA from *Escherichia coli*, also possesses 2-keto acid decarboxylase activity, as well as the enzyme encoded by the gene dxs of *Escherichia coli*. Functional homologues, functional variants and functional fragments of said genes and proteins are encompassed by the definition.

Genes coding for a hydroxy aldehyde reductase activity are also well known in the art, including the yghD, fucO, dkgA, dkgB genes from *Escherichia coli* and the ADH1 and ADH2 genes from *Saccharomyces cerevisiae*. Functional homologues, functional variants and functional fragments of said genes and proteins are encompassed by the definition.

In a preferred embodiment, the genetically modified microorganism for the production of 1,3-propanediol from 4-hydroxy-2-ketobutyrate expressed at least one of the following genes: at least one gene coding for a 2-keto acid decarboxylase activity selected among kivD gene from *Lactococcus lactis* and pdc gene from *Zymomonas mobilis* and at least the ydhD gene from *Escherichia coli* coding for a hydroxy aldehyde reductase activity.

In a further preferred embodiment, the genetically modified microorganism for the production of 1,3-propanediol from 4-hydroxy-2-ketobutyrate is an *Escherichia coli* overexpressing kivD gene from *Lactococcus lactis* and yqhD gene from *Escherichia coli*.

In another specific embodiment of the invention, the genetically modified microorganism for the production of the desired derivative of 4-hydroxy-2-ketobutyrate is modified for the production of 3-hydroxypropionaldehyde from 4-hydroxy-2-ketobutyrate. This modified microorganism is particularly described in WO 2010/076324, WO 2012/001003 and WO 2012/004247, incorporated herein by reference.

The metabolic pathway for the conversion of 4-hydroxy-2-ketobutyrate into 3-hydroxypropionaldehyde comprises only one step of conversion of 4-hydroxy-2-ketobutyrate into 3-hydroxypropionaldehyde.

Preferably, the genetically modified microorganism is, particularly a bacterium modified by expressing at least one gene encoding an enzyme with 2-keto acid decarboxylase activity for the conversion of 4-hydroxy-2-ketobutyrate into 3-hydroxypropionaldehyde. This gene can be exogenous or endogenous, and can be expressed chromosomally or extra-chromosomally.

Genes coding for a 2-keto acid decarboxylase activity are known in the art, as mentioned above.

In a preferred embodiment, the genetically modified microorganism for the production of 3-hydroxypropionaldehyde from 4-hydroxy-2-ketobutyrate expressed at least one gene coding for a 2-keto acid decarboxylase activity selected in the group consisting of kivD gene from *Lacto-*

*coccus lactis* and pdc gene from *Zymomonas mobilis*, more preferably kivD gene from *Lactococcus lactis.*

In another particular embodiment of the invention, the genetically modified microorganism for the production of the desired derivative of 4-hydroxy-2-ketobutyrate is modified for the production of 3-hydroxypropionate from 4-hydroxy-2-ketobutyrate. This modified microorganism is particularly described in WO 2012/001003, incorporated herein by reference.

The metabolic pathway for the conversion of 4-hydroxy-2-ketobutyrate into 3-hydroxypropionate is preferably a two-steps pathway comprising:

- conversion of 4-hydroxy-2-ketobutyrate into 3-hydroxypropionaldehyde, and
- conversion of 3-hydroxypropionaldehyde into 3-hydroxypropionate Preferably, the genetically modified microorganism is, particularly a bacterium modified by expressing at least one gene encoding an enzyme with 2-keto acid decarboxylase activity for the conversion of 4-hydroxy-2-ketobutyrate into 3-hydroxypropionaldehyde and at least one gene encoding an enzyme with hydroxyl aldehyde dehydrogenase activity for the conversion of 3-hydroxypropionaldehyde into 3-hydroxypropionate. Those genes can be exogenous or endogenous, and can be expressed chromosomally or extra-chromosomally.

Genes coding for a 2-keto acid decarboxylase activity are known in the art, as mentioned above. Genes coding for a hydroxyl aldehyde dehydrogenase are also well known in the art including the aldA, aldB, aldH, gabD genes from *Escherichia coli* and the ald4 gene from *Saccharomyces cerevisiae*. Functional homologues, functional variants and functional fragments of said genes and proteins are encompassed by the definition.

In a preferred embodiment, the genetically modified microorganism expressed at least one of the following genes: at least one gene coding for a 2-keto acid decarboxylase activity and selected among kivD gene from *Lactococcus lactis* and pdc gene from *Zymomonas mobilis* and at least one gene coding for a hydroxyl aldehyde dehydrogenase activity selected among the aldA, aldB, aldH, gabD genes from *Escherichia coli* or the ald4 gene from *Saccharomyces cerevisiae.*

In a further preferred embodiment, the genetically modified microorganism for the production of 3-hydroxypropionate from 4-hydroxy-2-ketobutyrate is an *Escherichia coli* overexpressing kivD gene from *Lactococcus lactis* and ald4 gene from *Saccharomyces cerevisiae.*

In another specific embodiment of the invention, the genetically modified microorganism for the production of the desired derivative of 4-hydroxy-2-ketobutyrate is modified for the production of 2,4-dihydroxybutyrate from 4-hydroxy-2-ketobutyrate. This microorganism is particularly described in WO 2014/009435 and WO2016/162442 incorporated herein by reference.

The metabolic pathway for the conversion of 4-hydroxy-2-ketobutyrate into 2,4-dihydroxybutyrate is preferably in one-step pathway.

Preferentially, the genetically modified microorganism is, particularly a bacterium modified by expressing at least one gene encoding an enzyme with 4-hydroxy-2-ketobutyrate reductase activity for the conversion of 4-hydroxy-2-ketobutyrate into 2,4-dihydroxybutyrate. These genes can be exogenous or endogenous, and can be expressed chromosomally or extra-chromosomally.

Most preferably the genetically modified microorganism for the production of 2,4-dihydroxybutyrate from 4-hydroxy-2-ketobutyrate according to the invention expresses at least one of the following genes coding for enzyme having 4-hydroxy-2-ketobutyrate reductase activity well known in the art: genes coding for lactate dehydrogenase such as IdhA from *Oryctalagus cuniculus*, idhA from *Lactococcus lactis*, idH from *Geobacillus stearothermophilus*, idh from *Bacillus subtilis* or idhA from *Escherichia coli*; genes coding for malate dehydrogenase such as mdh from *Escherichia coli* and genes coding for branched chain 2-hydroxyacid dehydrogenase such as panE from *Lactococcus lactis*. Functional homologues, functional variants and functional fragments of said genes and proteins are encompassed by the definition.

In a preferred embodiment, the genetically modified microorganism for the production of 2,4-dihydroxybutyrate from 4-hydroxy-2-ketobutyrate is an *Escherichia coli* overexpressing idhA gene from *Lactococcus lactis.*

Preferentially, the genetically modified microorganism of the invention is also modified to stimulate the flux in the oxaloacetate biosynthesis pathway; this result can be achieved by increasing the level of expression of phosphoenolpyruvate carboxylase, encoded by the ppc gene or by increasing the level of expression of pyruvate carboxylase, encoded by the gene pyc. Increasing the expression of phosphoenolpyruvate carboxylase can be accomplished by introducing artificial promoters that drive the expression of the ppc gene, by increasing the number of copies in the cell or by introducing mutations into the ppc gene that increase the activity of the corresponding protein. Increasing the expression of pyruvate carboxylase can be accomplished by introducing a heterologous gene encoding pyruvate carboxylase if the microorganism of the invention is devoid of pyc gene, by introducing strong artificial promoters to drive the expression of the pyc gene, by increasing the number of copies of the gene in the cell or by introducing mutations into the pyc gene that increase the activity of the corresponding protein.

The availability of the intermediate product oxaloacetate can also be increased by attenuating the level of expression of genes coding for phosphoenolpyruvate carboxykinase and/or malic enzymes, encoded by the pckA and/or maeA and/or maeB genes, respectively. This can be done by replacing the wild-type promoter of these genes by a weaker promoter, or by the use of an element destabilizing the corresponding messenger RNA or the protein. If needed, complete attenuation of the genes can also be achieved by the deletion of the corresponding DNA sequences. The invention is also related to the microorganism, particularly a bacterium, according to this particular embodiment of the invention, i.e. a microorganism, particularly a bacterium, presenting an increased availability of the oxaloacetate.

In another embodiment, the genetically modified microorganism is modified to stimulate the flux into the homoserine biosynthesis pathway. This can be achieved by increasing the expression of aspartokinase and homoserine dehydrogenase and/or aspartate semialdehyde dehydrogenase, encoded by the thrA and asd genes, respectively. Increasing the expression of aspartokinase and homoserine dehydrogenase and/or aspartate semialdehyde dehydrogenase can be accomplished by introducing artificial promoters that drive the expression of the thrA and/or asd genes, by increasing the number of copies in the cell or by introducing mutations into the thrA and/or asd genes that increase the activity of the corresponding proteins. The invention is also related to the microorganism, particularly a bacterium, according to this particular embodiment of the invention.

In a particular embodiment, mutations can be introduced into the thrA gene that reduce its sensitivity to the feed-back inhibitor threonine (feed-back desensitized alleles) and thus permit an increased activity in the presence of threonine. Advantageously, in all the preferred embodiments described herein, the microorganism is expressing a thrA* allele with reduced sensitivity to the feed-back inhibitor threonine (Reinscheid et al., 1991 and WO2007/077041).

Another way to stimulate the flux into homoserine biosynthesis pathway is to increase the expression of aspartate aminotransferase encoded by aspC gene. Increasing the expression of aspartate aminotransferase can be accomplished by introducing strong artificial promoters that drive the expression of the aspC gene, by increasing the number of copies of the gene in the cell or by introducing mutations into the aspC gene that increase the activity of the corresponding protein.

In a further embodiment of the invention, the genetically modified microorganism is also modified to present an attenuated level of homoserine conversion to other compounds than derivatives of 4-hydroxy-2-ketobutyrate. This result may be achieved by attenuating the level of homoserine consuming enzymes like homoserine kinase and threonine synthase (encoded by thrB and thrC), homoserine O-transsuccinylase (encoded by metA) or dihydrodipicolinate synthase (encoded by dapA). These genes can be attenuated by replacing the natural promoter by a weaker promoter or by elements destabilizing the corresponding messenger RNA or protein. If needed, complete attenuation of the gene can also be achieved by the deletion of the corresponding DNA sequence. The invention is also related to the microorganism, particularly a bacterium, according to this particular embodiment of the invention.

Optionally, the genetically modified microorganism, particularly a bacterium, is further modified to present an attenuated level of 3-hydroxypropionaldehyde conversion to other compounds than 1,3-propanediol. This may be achieved by attenuating the level of 3-hydroxypropionaldehyde consuming enzymes like 3-hydroxypropionaldehyde dehydrogenase (encoded by aldA, aldB, aldH, gabD). These genes can be attenuated by replacing the natural promoter by a weaker promoter or by elements destabilizing the corresponding messenger RNA or the protein. If needed, complete attenuation of the gene can also be achieved by the deletion of the corresponding DNA sequence. The invention is also related to the microorganism, particularly a bacterium, according to this particular embodiment of the invention.

Also, the genetically modified microorganism may be modified so as the efficiency of the sugar import is increased, either by using a sugar import system not relying on phosphoenolpyruvate (PEP) as phospho donor such as the one encoded by galP that is known to transport glucose, or by providing more phosphoenolpyruvate (PEP) to the sugar-phosphotransferase system. Various means exist that may be used to increase the availability of PEP in a microorganism. In particular, this may be accomplished by attenuating the reaction PEP towards pyruvate. Preferentially, at least one gene selected among pykA and pykF, encoding pyruvate kinase, is attenuated in said strain in order to obtain this result. Another way to improve the glucose uptake rate of a microorganism is to increase the amount of the PTS permease and to optimize the phosphorylation cascade, by overexpressing at least one of the genes ptsG, ptsH, ptsI and crr or by attenuating the known regulating repression of the PTS system.

In the invention, the genetically modified microorganism may further be modified to use sucrose as a sole source of carbon, as described in WO 2012/004247, incorporated herein by reference.

Particularly the modified microorganism comprises functional genes coding for a PTS sucrose utilization system and/or for a non-PTS sucrose utilization system.

A PTS sucrose utilization system is a system for sucrose utilization based on the transport of sucrose by a phosphoenolpyruvate (PEP)-dependent sucrose phosphotransferase system (Sucrose-PTS). A phosphotransferase system couples the transport of a sugar (e.g. sucrose or glucose) with the phosphorylation of the sugar using PEP as phosphate donor. After transport into the cell, the sucrose-phosphate is cleaved into glucose-6-phosphate and fructose by an invertase. Fructose is then phosphorylated into fructose-6-phosphate by a fructokinase. The genes coding for this PTS sucrose utilization system can be controlled by a regulatory protein.

A non-PTS sucrose utilization system is a system for sucrose utilization based on transport of sucrose by a system independent of phosphoenolpyruvate. After transport into the cell, the sucrose is cleaved into glucose and fructose by an invertase. Fructose is then phosphorylated into fructose-6-phosphate by a fructokinase and glucose is phosphorylated into glucose-6-phosphate by a glucokinase. The genes coding for this non-PTS sucrose utilization system can be controlled by a regulatory protein.

Preferably, the microorganism expresses naturally or has been modified with the introduction of the genes: scrKYABR (scrK coding for a fructokinase, scrY coding for a porin, scrA coding for the Protein IIBC, scrB coding for a sucrose-6-P invertase, scrR coding for a repressor) from *Salmonella*. A conjugative plasmid pUR400 bearing said genes scrKYABR might be used to transform the microorganism. These genes can be used all together in combination, or in any combination comprising at least one of these genes. In particular, the gene scrR can be omitted.

Also preferably, the microorganism expresses naturally or has been modified with the introduction of the genes from *E. coli* EC3132 i.e. the genes cscBKAR coding for a sucrose: proton symport transport system (cscB), a fructokinase (cscK), an invertase (cscA) and a sucrose-specific repressor (cscR). These genes can be used all together in combination or in any combination comprising at least one of these genes. In particular, the gene cscR can be omitted. Homologous genes from other organisms can also be used.

The genetically modified microorganism of the present invention is also genetically modified so as L-homoserine is converted into 4-hydroxy-2-ketobutyrate by transamination with a mutant phosphoserine aminotransferase. To this end, said genetically modified microorganism further comprises a gene coding for a mutant phosphoserine aminotransferase comprising amino acid R (Arg) at position 42, by reference to *E. coli* phosphoserine aminotransferase of SEQ ID NO: 2, replaced by a non-polar amino acid.

In one embodiment, said genetically modified microorganism further comprises mutation where amino acid R (Arg) at position 77, by reference to *E. coli* phosphoserine aminotransferase of SEQ ID NO: 2 is replaced by a polar uncharged or a non-polar amino acid.

In the context of the invention, the terms “mutant phosphoserine aminotransferase” and “mutant phosphoserine aminotransferase having an improved L-homoserine aminotransferase activity” are equivalent and defined as an enzyme having an improved L-homoserine aminotransferase activity converting L-homoserine in 4-hydroxy-2-ketobutyrate by transamination with an attenuated or inhibited phosphoserine aminotransferase activity O-phospho-L-serine in 3-phosphonooxypyruvate, compared to the non-mutant phosphoserine aminotransferase. The measurement of aminotransferase activities is well known by the man skilled in the art and can be achieved by measurement of a specific product disappearance. For instance, for the phosphoserine transaminase assay, the transamination of phosphoserine is measured using a coupled enzymatic assay, which follows the consumption of the substrate of the coupled reaction 3-acetylpyridine adenine dinucleotide (APAD). For the homoserine transaminase assay, the same coupled enzymatic assay is used with homoserine as substrate. Preferably, the mutant phosphoserine aminotransferase according to the present invention has a phosphoserine aminotransferase activity which is significantly reduced from at least 10 times less and up to no quantifiable activity, compared to the non-mutant or unmodified phosphoserine aminotransferase, with an homoserine aminotransferase activity which is at least 2 times more than the non-mutant or unmodified phosphoserine aminotransferase.

The gene coding for the mutant phosphoserine aminotransferase may be a modified gene endogenous to the said modified microorganism. The mutated protein is identified as a "modified endogenous phosphoserine aminotransferase".

In one embodiment, mutations are introduced by directed mutagenesis into the coding sequence of said gene into the genome of said microorganism. The microorganism may be further modified for increasing the expression of the mutated gene. Preferably, the gene coding for a mutant phosphoserine aminotransferase having an improved L-homoserine aminotransferase activity is under control of a strong promoter.

The gene coding for the phosphoserine aminotransferase may be heterologous to the said modified microorganism of the invention and modified by mutation to code for a mutant phosphoserine aminotransferase having an improved L-homoserine aminotransferase activity converting L-homoserine in 4-hydroxy-2-ketobutyrate by transamination. The mutated protein is identified as "heterologous mutated phosphoserine aminotransferase".

In one embodiment, the sequence coding for the mutated heterologous phosphoserine aminotransferase having an improved L-homoserine aminotransferase activity is introduced into the genome of the microorganism by replacing the coding sequence for the endogenous phosphoserine aminotransferase. The microorganism may be further modified for increasing the expression of the mutated gene. Preferably, the gene coding for a mutant phosphoserine aminotransferase is under control of a strong promoter.

In another embodiment, the microorganism is modified by introducing one or more copies of the gene coding for a mutant phosphoserine aminotransferase having an improved L-homoserine aminotransferase activity converting L-homoserine in 4-hydroxy-2-ketobutyrate by transamination. The microorganism may thus comprise one or more copies of a gene comprising a coding sequence for the endogenous mutated phosphoserine aminotransferase under control of regulatory elements for the expression of the gene into the microorganism or one or more copies of a gene comprising a coding sequence for an heterologous mutated phosphoserine aminotransferase under control of regulatory elements for the expression of the gene into the microorganism.

Phosphoserine aminotransferase enzymes (PSAT) belong to Enzyme Class 2.6.1.52 are well known by the man skilled in the art, as they participate in the biosynthetic pathway for the amino acids serine. Phosphoserine aminotransferase and genes coding for enzymes having a phosphoserine aminotransferase activity are known in the art and are in particular disclosed in Table 1.

TABLE 1

Enzymes having phosphoserine aminotransferase activity and genes encoding such phosphoserine aminotransferase.

| GenBank accession number | Uniprot accession number | Gene name | Protein name | Organism |
|---|---|---|---|---|
| WP_000057138.1 (SEQ ID NO: 1) | P23721 (SEQ ID NO: 2) | serC | Phosphoserine aminotransferase | *Escherichia Coli* (strain K12) |
| WP_012133020.1 (SEQ ID NO: 15) | A8AIH6 (SEQ ID NO: 16) | serC | Phosphoserine transaminase | *Citrobacter koseri* |
| WP_012016824.1 (SEQ ID NO: 17) | A4W8S7 (SEQ ID NO: 18) | serC | Phosphoserine aminotransferase | *Enterobacter* sp. (strain 638) |
| WP_015839985.1 (SEQ ID NO: 19) | C6DF64 (SEQ ID NO: 20) | serC | Phosphoserine aminotransferase | *Pectobacterium carotovorum* subsp. *carotovorum* |
| WP_012884949.1 (SEQ ID NO: 21) | D2C1I9 (SEQ ID NO: 22) | serC | Phosphoserine aminotransferase | *Dickeya zeae* (strain Ech586) |
| NP_743924.1 (SEQ ID NO: 23) | Q88M07 (SEQ ID NO: 24) | serC | Phosphoserine aminotransferase | *Pseudomonas putida* |

TABLE 1-continued

Enzymes having phosphoserine aminotransferase activity and genes encoding such phosphoserine aminotransferase.

| GenBank accession number | Uniprot accession number | Gene name | Protein name | Organism |
|---|---|---|---|---|
| WP_012722929.1 (SEQ ID NO: 25) | C3K6J5 (SEQ ID NO: 26) | serC | Phosphoserine aminotransferase | *Pseudomonas fluorescens* (strain SBW25) |
| WP_003111764.1 (SEQ ID NO: 27) | Q02PX3 (SEQ ID NO: 28) | serC | Phosphoserine aminotransferase | *Pseudomonas aeruginosa* |
| NP_388883.1 (SEQ ID NO: 29) | P80862 (SEQ ID NO: 30) | serC | Phosphoserine aminotransferase | *Bacillus Subtilis* (strain 168) |
| NP_179354.1 (SEQ ID NO: 31) | Q9SHP0 (SEQ ID NO: 32) | PSAT2 | Phosphoserine aminotransferase 2, chloroplastic | *Arabidopsis thaliana* |
| NP_014827.3 (SEQ ID NO: 33) | P33330 (SEQ ID NO: 34) | serC | Phosphoserine aminotransferase | *Saccharomyces cerevisiae* |
| CAJ91938.1 (SEQ ID NO: 35) | Q0KDI3 (SEQ ID NO: 36) | serC | phosphoserine aminotransferase | *Ralstonia eutropha* H16 |
| NP_266759.1 (SEQ ID NO: 37) | Q9CHW5 (SEQ ID NO: 38) | serC | Phosphoserine aminotransferase | *Lactococcus lactis* subsp *lactis* (strain IL1403) |
| WP_011967440.1. (SEQ ID NO: 39) | A6LPI5 (SEQ ID NO: 40) | serC | Phosphoserine aminotransferase | *Clostridium beijerinckii* |

Phosphoserine aminotransferase and genes preferred for being mutated to convert L-homoserine into 4-hydroxy-2-ketobutyrate by transamination are selected among serC from *Escherichia coli*, serC from *Citrobacter koseri*, serC from *Enterobacter* sp., serC from *Pectobacterium carotovorum*, serC from *Dickeya zeae*, serC from *Pseudomonas putida*, serC from *Pseudomonas fluorescens*, serC from *Pseudomonas aeruginosa*, serC from *Bacillus subtilis*, PSAT2 from *Arabidopsis thaliana*, serC from *Saccharomyces cerevisiae*, serC from *Ralstonia eutropha*, serC from *Lactococcus lactis* and serC from *Clostridium beijerinckii*. Any phosphoserine aminotransferase coding gene having at least 80-85% preferentially 85-90%, more preferentially 90-95%, even more preferentially 96%, 97%, 98%, 99% sequence identity to any of those genes may be used. The identity percentage is calculated by any sequence analysis method known by the skilled person, and particularly with algorithms such as Needleman-Wunsch. The identity percentage is calculated over the whole length of the query sequence.

Preferably, genes for being mutated to encode a mutant phosphoserine aminotransferase are serC from *E. coli*.

A molecular dynamic simulation of the phosphoserine aminotransferase allowed to position in the binding site the homoserine substrate.

In a preferred embodiment, the mutant phosphoserine aminotransferase comprises at least one mutation(s) into the binding site(s) of homoserine.

The homology modeling of homoserine binding of *E. coli* phosphoserine aminotransferase allowed identifying two residues, R42 and R77 (see FIG. 1). These were considered to be a critical factor to discriminate homoserine against other ligands.

In one embodiment, in the genetically modified microorganism, the mutant phosphoserine aminotransferase comprises a mutation where amino acid R (Arg) at position 42, by reference to *E. coli* phosphoserine aminotransferase of SEQ ID NO: 2, is replaced with a non-polar amino acid to prevent hydrogen bonds with the hydroxy group of homoserine, and preferably replaced with a non-polar amino acid such as A (Ala), F (Phe), G (Gly), I (Ile), L (Leu), M (Met), P (Pro), V (Val) and W (Trp), Y (Tyr). More preferably the amino acid R (Arg) at position 42, by reference to *E. coli* phosphoserine aminotransferase of SEQ ID NO: 2, is replaced with an aromatic non-polar amino acid such as W (Trp), Y (Tyr), F (Phe), most preferably replaced with amino acid W (Trp).

In another embodiment, in the genetically modified microorganism, the mutant phosphoserine aminotransferase further comprises a mutation where amino acid R (Arg) at position 77, by reference to *E. coli* phosphoserine aminotransferase of SEQ ID NO: 2, is replaced with a polar uncharged amino acid, such as S (Ser), T (Thr), N (Asn), Q (Gln), or with a non-polar amino acid such as A (Ala), F (Phe), G (Gly), I (Ile), L (Leu), M (Met), P (Pro), V (Val) and W (Trp), Y (Tyr). More preferably, the mutant phosphoserine aminotransferase comprises a mutation where amino acid R (Arg) at position 77, by reference to *E. coli* phosphoserine aminotransferase of SEQ ID NO: 2, is replaced with amino acid T (Thr) or W (Trp).

In a preferred embodiment, the genetically modified microorganism of the invention has a mutant phosphoserine aminotransferase which comprises at least the amino acid R (Arg) at position 42, by reference to *E. coli* phosphoserine aminotransferase of SEQ ID NO: 2, which is replaced with a non-polar amino acid and the amino acid R (Arg) at position 77, by reference to *E. coli* phosphoserine aminotransferase of SEQ ID NO: 2, which is replaced by a polar uncharged or a non-polar amino acid. In this particular embodiment, all the preferred mutations as described above for replacing the amino acid R (Arg) at position 42 and the amino acid R (Arg) at position 77, by reference to *E. coli* phosphoserine aminotransferase of SEQ ID NO: 2, apply mutatis mutandis.

Amino acids and their position are identified by reference to *E. coli* phosphoserine aminotransferase of SEQ ID NO: 2. The person skilled in the art will however be in position to identify the corresponding amino acids responsible for homoserine binding in other phosphoserine aminotransferase in using the method used for *E. coli* sequence. Particularly, by simple sequence alignment and without need for a molecular modelling as shown in the examples for *E. coli* sequence, the person skilled in the art can identify homologies and identities in the protein sequences sufficient to identify the corresponding amino acids (see FIG. 2).

In a preferred embodiment, the mutated phosphoserine aminotransferase has the sequence as depicted in SEQ ID NO:7, in SEQ ID NO: 9 or in SEQ ID NO: 11.

An advantageous genetically modified microorganism for production of 1,3 propanediol according to the present invention preferably comprises, or consist in:

- overexpressing kivD gene from *Lactococcus lactis* and yqhD gene from *Escherichia coli*, with
- a gene coding for a mutant phosphoserine aminotransferase comprising amino acid R (Arg) at position 42, by reference to *E. coli* phosphoserine aminotransferase of SEQ ID NO: 2, replaced with amino acid W (Trp) and amino acid R (Arg) at position 77, by reference to *E. coli* phosphoserine aminotransferase of SEQ ID NO: 2 replaced with amino acid W (Trp). More preferably, such an advantageous genetically modified microorganism for production of 1,3 propanediol according to the present invention further comprises overexpression of thrA* gene.

Another advantageous genetically modified microorganism for production of 2,4-dihydroxybutyrate according to the present invention preferably comprises, or consist in:

- overexpressing IdhA gene from *Lactococcus lactis*, with
- a gene coding for a mutant phosphoserine aminotransferase comprising amino acid R (Arg) at position 42, by reference to *E. coli* phosphoserine aminotransferase of SEQ ID NO: 2, replaced with amino acid W (Trp) and amino acid R (Arg) at position 77, by reference to *E. coli* phosphoserine aminotransferase of SEQ ID NO: 2 replaced with amino acid T (Thr). More preferably, such an advantageous genetically modified microorganism for production of 2,4-dihydroxybutyrate according to the present invention further comprises overexpression of thrA* gene.

In another advantageous embodiment, for further improving the production of the derivates of 4-hydroxy-2-ketobutyrate, the endogenous gene serC is attenuated, repressed in an inducible way or deleted in the genetically modified microorganism. This particular feature may be combined to any preferred embodiment mentioned here in.

In a second aspect, the present invention concerns a method for the production of derivatives of 4-hydroxy-2-ketobutyrate selected in the group consisting of 1,3-propanediol, 3-hydroxypropionaldehyde, 3-hydroxypropionate and 2,4-dihydroxybutyrate, in particular by fermentation, comprising the steps of:

- culturing in a culture medium comprising a source of carbon a microorganism which is genetically modified for the production of the desired derivative of 4-hydroxy-2-ketobutyrate and further comprising a gene coding for a mutant phosphoserine aminotransferase having an improved L-homoserine aminotransferase activity converting by transamination L-homoserine into 4-hydroxy-2-ketobutyrate as described above, and
- recovering the desired derivative of 4-hydroxy-2-ketobutyrate from the culture medium.

Therefore, in the method of production according to the invention, the modified microorganism to be cultured is a microorganism genetically modified for the production of a derivative of 4-hydroxy-2-ketobutyrate selected in the group consisting of 1,3-propanediol, 3-hydroxypropionaldehyde, 3-hydroxypropionate and 2,4-dihydroxybutyrate, further comprising a gene coding for a mutant phosphoserine aminotransferase having an improved L-homoserine aminotransferase activity converting L-homoserine into 4-hydroxy-2-ketobutyrate by transamination as defined above, and preferably as defined in the examples.

Methods for the production of the desired derivative of 4-hydroxy-2-ketobutyrate by fermentation of modified microorganisms and recovery of the desired derivative of 4-hydroxy-2-ketobutyrate from the fermentation medium are known in the art, including WO 2010/076324, WO 2012/001003, WO 2012/004247, WO 2014/009435 and WO2016/162442, incorporated herein by reference.

Fermentation mediums and sources of carbon are also well known. According to the invention, the terms "fermentative process", "fermentation" or 'culture' are used interchangeably to denote the growth of microorganism. This growth is generally conducted in fermenters with an appropriate growth medium adapted to the microorganism being used.

A "culture medium" designates a medium (e.g., a sterile, liquid media) comprising nutrients essential or beneficial to the maintenance and/or growth of the cell such as carbon sources or carbon substrates or carbohydrate, nitrogen sources, for example, peptone, yeast extracts, meat extracts, malt extracts, urea, ammonium sulfate, ammonium chloride, ammonium nitrate and ammonium phosphate; phosphorus sources, for example, monopotassium phosphate or dipotassium phosphate; trace elements (e.g., metal salts), for example magnesium salts, cobalt salts and/or manganese salts; as well as growth factors such as amino acids and vitamins.

The term "source of carbon", "carbon source" or "carbon substrate" according to the present invention refers to any carbon source capable of being metabolized by a microorganism wherein the substrate contains at least one carbon atom.

The term "carbohydrate" refers to any carbon source capable of being metabolized by a microorganism and containing at least one carbon atom, two atoms of hydrogen and one atom of oxygen.

The carbohydrate is selected among the group consisting of monosaccharides such as glucose, fructose, mannose, xylose, arabinose, galactose and the like, disaccharides such as sucrose, cellobiose, maltose, lactose and the like, oligosaccharides such as raffinose, stachyose, maltodextrins and the like, polysaccharides such as cellulose, hemicellulose, starch and the like, methanol, formaldehyde and glycerol. Especially preferred carbon sources are arabinose, fructose, galactose, glucose, lactose, maltose, sucrose, xylose or a mixture thereof. More preferably carbon source is sucrose.

In a particular embodiment of the invention, the carbon source is derived from renewable feed-stock. Renewable feed-stock is defined as raw material required for certain industrial processes that can be regenerated within a brief delay and in sufficient amount to permit its transformation into the desired product. Vegetal biomass treated or not, is an interesting renewable carbon source.

Those skilled in the art are able to define the culture conditions for the microorganisms according to the invention. In particular the bacteria are fermented at a temperature between 20° C. and 55° C., preferentially between 25° C. and 40° C., and more specifically about 30° C. to 37° C. for *E. coli*.

This process can be carried out either in a batch process, in a fed-batch process or in a continuous process. It can be carried out under aerobic, micro-aerobic or anaerobic conditions.

'Under aerobic conditions' means that oxygen is provided to the culture by dissolving the gas into the liquid phase. This could be obtained by (1) sparging oxygen containing gas (e.g. air) into the liquid phase or (2) shaking the vessel containing the culture medium in order to transfer the oxygen contained in the head space into the liquid phase. The main advantage of the fermentation under aerobic conditions is that the presence of oxygen as an electron acceptor improves the capacity of the strain to produce more energy under the form of ATP for cellular processes. Therefore, the strain has its general metabolism improved.

Micro-aerobic conditions are defined as culture conditions wherein low percentages of oxygen (e.g. using a mixture of gas containing between 0.1 and 10% of oxygen, completed to 100% with nitrogen), is dissolved into the liquid phase.

Anaerobic conditions are defined as culture conditions wherein no oxygen is provided to the culture medium. Strictly anaerobic conditions are obtained by sparging an inert gas like nitrogen into the culture medium to remove traces of other gas. Nitrate can be used as an electron acceptor to improve ATP production by the strain and improve its metabolism.

The action of "recovering the desired derivative of 4-hydroxy-2-ketobutyrate from the culture medium" designates the action of collecting the produced desired derivative of 4-hydroxy-2-ketobutyrate from the fermentation medium whatever its purity degree. "Recovering" means collecting the first product directly obtained from the fermentative process (fermentation must) which contains the product of interest (in this case desired derivative of 4-hydroxy-2-ketobutyrate) and other co-products of the fermentation so with a more or less acceptable purity degree.

The above method can also comprise a further step of purifying the desired derivative of 4-hydroxy-2-ketobutyrate if the purity degree obtained after the step of recovering is less acceptable. The "purifying" step consists of specifically purify the product of interest (in this case desired derivative of 4-hydroxy-2-ketobutyrate) in order to obtain said product of interest with an improved purity degree that is to say by eliminating all the co-products.

For example, 1,3-propanediol might be recovered and purified by techniques and means well known by the man skilled in the art and have notably been described in patent applications, WO 2009/068110 and WO 2010/037843 herein incorporated by reference.

Preferably, the method of production according to the present invention is performed with a microorganism, particularly a bacterium, which contains at least one gene encoding an enzyme with 2-keto acid decarboxylase activity for the conversion of 4-hydroxy-2-ketobutyrate into 3-hydroxypropionaldehyde and at least one gene encoding an enzyme with hydroxy aldehyde reductase activity for the conversion of 3-hydroxypropionaldehyde into 1,3-propanediol.

Preferably, the method of production according to the present invention is performed with a microorganism, particularly a bacterium, which contains at least one gene encoding an enzyme with 2-keto acid decarboxylase activity for the conversion of 4-hydroxy-2-ketobutyrate into 3-hydroxypropionaldehyde.

Preferably, the method of production according to the present invention is performed with a microorganism, particularly a bacterium, which contains at least one gene encoding an enzyme with 2-keto acid decarboxylase activity for the conversion of 4-hydroxy-2-ketobutyrate into 3-hydroxypropionaldehyde and at least one gene encoding an enzyme with hydroxyl aldehyde dehydrogenase activity for the conversion of 3-hydroxypropionaldehyde into 3-hydroxypropionate.

Preferably, the method of production according to the present invention is performed with a microorganism, particularly a bacterium, which contains at least one gene encoding an enzyme with 4-hydroxy-2-ketobutyrate reductase activity for the conversion of 4-hydroxy-2-ketobutyrate into 2,4-dihydroxybutyrate.

More preferably, and combined with any of the above desired derivatives of 4-hydroxy-2-ketobutyrate, the microorganism to be cultured in the method of the present invention comprises a gene coding for a mutant phosphoserine aminotransferase having an improved L-homoserine aminotransferase activity converting by transamination L-homoserine into 4-hydroxy-2-ketobutyrate, said mutant phosphoserine aminotransferase comprising at least the amino acid R (Arg) at position 42, by reference to *E. coli* phosphoserine aminotransferase of SEQ ID NO: 2, replaced by a non-polar amino acid. Even more preferably, and still combined with any of the above desired derivatives of 4-hydroxy-2-ketobutyrate, the microorganism to be cultured in the method of the present invention comprises a gene coding for a mutant phosphoserine aminotransferase having an improved L-homoserine aminotransferase activity converting by transamination L-homoserine into 4-hydroxy-2-ketobutyrate, said mutant phosphoserine aminotransferase further comprising amino acid R (Arg) at position 77, by reference to *E. coli* phosphoserine aminotransferase of SEQ ID NO: 2, replaced by a polar uncharged or a non-polar amino acid.

All preferred embodiments disclosed above for the genetically modified microorganism as such apply mutatis mutandis to the microorganism to be used in the method of production of the invention as disclosed herein.

In one other object, the present invention relates to the use of a genetically modified microorganism comprising a gene coding for a mutant phosphoserine aminotransferase having an improved L-homoserine aminotransferase activity converting by transamination L-homoserine into 4-hydroxy-2-ketobutyrate and wherein said mutant phosphoserine aminotransferase comprises at least one mutation where amino acid R (Arg) at position 42, by reference to *E. coli* phosphoserine aminotransferase of SEQ ID NO: 2, is replaced by a non-polar amino acid, for improving the production a derivatives of 4-hydroxy-2-ketobutyrate selected in the group consisting of 1,3-propanediol, 3-hydroxypropionaldehyde, 3-hydroxypropionate and 2,4-dihydroxybutyrate. The genetically modified microorganism comprising said mutant phosphoserine aminotransferase to be used for the production of said derivatives of 4-hydroxy-2-ketobutyrate may be already modified for the production of the desired derivative of 4-hydroxy-2-ketobutyrate.

EXAMPLES

Abbreviations 1,3-propanediol (PDO); isopropyl β-D-thiogalactopyranoside (IPTG); phosphotransferase system (PTS); 3-acetylpyridine adenine dinucleotide (APAD)

Materials and Methods

1 Molecular Modeling

Models of *E. coli* phosphoserine aminotransferase (SerC) with ligand were generated based on the structure retrieved from the Protein Data Bank (Code: 1BJO). The molecular dynamics simulation software Amber10 (Case et al., 2008) was used to refine the conformations of the mutated residues and the ligand. The Molecular Mechanics/Poisson-Boltzmann Surface Area (MM-GBSA) approach (Kollman et al., 2000), which is implemented in the Amber program, was applied to calculate the binding free energy.

2 Protocols

Several protocols have been used to strains described in the following examples. Protocol 1 (Chromosomal modifications by homologous recombination, selection of recombinants and antibiotic cassette excision) and protocol 2 (Transduction of phage P1) used in this invention have been fully described in patent application WO2013/001055.

Example 1: Engineering Phosphoserine Aminotransferase SerC to Utilize L-Homoserine as Substrate Construction of strain BL21(DE3) ΔserC::Cm (pET28aVB01-serC)=Strain 1

The serC gene (SEQ ID NO: 1) was cloned into a pET28a (Novagen) vector in such a way that the resulting SerC protein (SEQ ID NO: 2) gets a 6-Histidine tag at its C-terminal part (SEQ ID NO: 3).

For this purpose, the serC gene without its stop codon was amplified by PCR from the *E. coli* genome using appropriate oligonucleotides. The PCR product was restricted using appropriated enzymes and cloned into the vector pET28a restricted with the same restriction enzymes. The resulting vector was named pET28aVB01-serC. Then this vector was introduced into a BL21(DE3) strain (New England Biolabs), in which the endogenous serC gene was previously deleted, giving rise to strain 1: BL21(DE3) ΔserC::Cm (pET28aVB01-serC).

More precisely, to achieve the deletion of endogenous serC gene, the homologous recombination strategy described by Datsenko & Wanner, 2000 (according to Protocol 1) was used. A fragment carrying the chloramphenicol resistance marker flanked by DNA sequences homologous to upstream and downstream regions of the serC gene was PCR amplified by the overlapping PCR. The sequences for recombination into upstream and downstream regions of the serC gene are referred as SEQ ID NO: 4 and 5. The obtained PCR product "ΔserC::Cm" was then introduced by electroporation into the strain MG1655 (pKD46). The chloramphenicol resistant transformants were selected and the deletion of serC gene with the associated resistance cassette was verified by a PCR analysis with appropriate oligonucleotides. The strain retained was designated MG1655 ΔserC::Cm. Finally, the ΔserC::Cm modification was transferred by P1 phage transduction (according to Protocol 2) from MG1655 ΔserC::Cm strain to BL21(DE3) strain. Chloramphenicol resistant transductants were selected and the presence of ΔserC::Cm deletion was verified by a PCR analysis with appropriate oligonucleotides. The strain retained was designated BL21(DE3) ΔserC::Cm.

SerC Mutants Having an Improved Homoserine Aminotransferase Activity with a Reduced Phosphoserine Aminotransferase Activity The three SerC mutant proteins studied in this application are the following:

```
                  (SEQ ID NO: 6 and SEQ ID NO: 7)
SerC*(R42W)

                  (SEQ ID NO: 8 and SEQ ID NO: 9)
SerC*(R42W/R77T)

                 (SEQ ID NO: 10 and SEQ ID NO: 11)
SerC*(R42W/R77W)
```

The three corresponding genes were individually cloned on a pET28a (Novagen) vector in such a way that SerC mutant proteins get a 6-Histine tag into their C-terminal part as described above with the SerC wild type protein. The resulting protein sequences are referred as SEQ ID NO: 12, SEQ ID NO: 13 and SEQ ID NO: 14, for SerC*(R42W), SerC*(R42W/R77T) and SerC*(R42W/R77W), respectively, and the respective pET28a type plasmid referred as pET28aVB01-serC*(R42W), pET28aVB01-serC*(R42W/R77T) and pET28aVB01-serC*(R42W/R77W), respectively.

Example 2: Evaluation of L-Homoserine or Phosphoserine Aminotransferase In Vitro Activity of SerC Mutants Construction of the Strains Overproducing SerC Mutants for their Characterization The plasmids pET28aVB01-serC*(R42W), pET28aVB01-serC*(R42W/R77T) and pET28aVB01-serC*(R42W/R77W) obtained from example 1 were individually introduced into a BL21(DE3) ΔserC::Cm strain, giving rise to strain 2: BL21(DE3) ΔserC::Cm (pET28aVB01-serC*(R42W), to strain 3: BL21(DE3) ΔserC::Cm (pET28aVB01-serC*(R42W/R77T)) and to strain 4: BL21(DE3) ΔserC::Cm (pET28aVB01-serC*(R42W/R77W)).

Overproduction, Purification of SerC Mutants

The overproduction strains were grown at 37° C. in 500 mL of LB media with 2.5 g/L glucose and supplemented with 50 μg/mL of kanamycin. The flasks were agitated at 200 RPM on orbital shaker. When the $OD_{600\ nm}$ reached 0.6 units, the gene expression was induced by adding 0.1 mM isopropyl β-D-thiogalactopyranoside (IPTG) for 3 hours at 250 C. The cells were harvested by centrifugation after the night ($OD_{600}$ above 4 units). The supernatant was discarded and the pellet was stored at 4° C. before use.

For protein extraction and purification, between 50-60 mg of *E. coli* biomass were re-suspended in 9 ml of 50 mM $Na_2HPO_4$ (pH 7.6), 0.2 mM EDTA, 0.1 mM dithiothreitol, 0.1 mM pyridoxal 5'-phosphate and a protease inhibitor cocktail. Suspended cells are disrupted by sonication (Bandelin, SONOPULS HD 2070) on ice during 8 cycles of 30 sec intervals and centrifuged at 12000 g for 30 min at 4° C. The supernatant is purified using a His Spin Trap (GE Healthcare) according to the manufacturer's instructions. The enzymes were eluted 2 times 200 µl of 50 mM $Na_2HPO_4$ (pH 7.4) 150 mM NaCl, 0.1 mM pyridoxal 5'-phosphate, 0.1 mM dithiothreitol, 200 mM Imidazole. The fractions containing the protein were pooled and the buffer was exchanged with 50 mM $Na_2HPO_4$ (pH 7.0) 150 mM NaCl, 0.1 mM pyridoxal 5'-phosphate using desalting column (PD-10, GE). The purity of the enzyme was checked by SDS-PAGE and the protein concentration was quantified using a Bio-Rad protein assay kit (Bio-Rad Laboratories).

The purified protein was stored in 50 mM $Na_2HPO_4$ (pH 7.0) 150 mM NaCl, 0.1 mM pyridoxal 5'-phosphate at −20° C. before use.

Characterization of SerC Mutants

Phosphoserine Aminotransferase Assay

The phosphoserine aminotransferase activity was measured at 30° C. using a coupled enzymatic assay. The phosphoserine aminotransferase activity assay was carried out in a total volume of 1 ml containing 200 mM potassium phosphate buffer pH 8.2, 2 mM 3-acetylpyridine adenine dinucleotide (APAD), 3 mM Phosphoserine, 60 units/ml glutamic dehydrogenase from bovine liver, 1 mM alpha-ketoglutaric acid neutralized and 2 µg of the purified protein. The consumption of 3-acetylpyridine adenine dinucleotide was monitored at 375 nm on a spectrophotometer. The activity detected in control assay, lacking the amino acceptor (alpha-ketoglutaric acid), was subtracted from the activity detected in the assay with the amino acceptor. A unit of phosphoserine aminotransferase activity is the amount of enzyme required to catalyze the transamination of 1 µmol of phosphoserine per min at 30° C. (Epsilon 375 nm=6100 M−1 cm−1).

L-Homoserine Aminotransferase Assay

The L-homoserine aminotransferase activity was measured at 30° C. using a coupled enzymatic assay. The L-homoserine aminotransferase activity assay was carried out in a total volume of 1 ml containing 200 mM potassium phosphate buffer pH 8.2, 2 mM 3-acetylpyridine adenine dinucleotide, 3 mM L-homoserine, 60 units/ml glutamic dehydrogenase from bovine liver, 1 mM alpha-ketoglutaric acid neutralized and 15 µg of the purified protein. The consumption of 3-acetylpyridine adenine dinucleotide was monitored at 375 nm on a spectrophotometer. The activity detected in control assay, lacking the amino acceptor (alpha-ketoglutaric acid), was subtracted from the activity detected in the assay with the amino acceptor. A unit of L-homoserine aminotransferase activity is the amount of enzyme required to catalyze the transamination of 1 µmol of L-homoserine per min at 30° C. (Epsilon 375 nm=6100 M−1 cm−1)

Activity of Purified serC Mutants on Phosphoserine (Table 2)

TABLE 2

| Mutation | [Phosphoserine] mM | Specific Activity mUI/mg | Compared with WT |
|---|---|---|---|
| WT | 3 | 3622 | 1 |
| R42W | 3 | 177 | 1/20 |
| R42W-R77T | 3 | <LQ | |
| R42W-R77W | 3 | <LQ | |

LQ: Limit of quantification

The purified protein serC*(R42W) was 20 times less active on the natural substrate phosphoserine than the wild type SerC protein. The double mutants SerC*(R42W/R77T) and SerC*(R42W/R77W) did not show any quantifiable activity on phosphoserine.

Activity of Purified serC Mutants on Homoserine (Table 3)

TABLE 3

| Mutation | [Homoserine] mM | Specific Activity mUI/mg | Compared with WT |
|---|---|---|---|
| WT | 3 | 95 | 1 |
| R42W | 3 | 205 | 2.2 |
| R42W-R77T | 3 | 244 | 2.6 |
| R42W-R77W | 3 | 325 | 3.4 |

The purified protein SerC*(R42W) was 2 times more active on the substrate Homoserine than the wild type protein SerC. The activity of the double mutants SerC*(R42W/R77T) and SerC*(R42W/R77W) was 3 times improved on 3 mM Homoserine.

SerC* mutants proteins have an improved specific homoserine aminotransferase activity and no or almost no phosphoserine aminotransferase activity. Among the mutants, SerC* containing both R42W and R77W is the most active one on homoserine.

Example 3: 1,3-Propanediol (PDO) Production by Overproduction of L-Homoserine Aminotransferase SerC* Mutants in *Escherichia coli*

Construction of Plasmid for Overexpression of the L-Homoserine Aminotransferase serC* Mutants in the 1,3-Propanediol Producer Strain To overexpress the mutated forms of serC gene, the serC*(R42W/R77T) (SEQ ID NO: 8) and serC*(R42W/R77W) (SEQ ID NO: 10) genes were expressed from the pME101-thrA*1-serC, previously described into patent application WO 2010/076324 using the natural promoter of serC gene.

For this purpose, the part of serC gene encompassing the mutation R42W/R77T or R42W/R77W was amplified by PCR from plasmid pET28aVB01-serC*(R42W/R77T) or pET28aVB01-serC*(R42W/R77W), respectively, using appropriate oligonucleotides. Each PCR product was restricted using appropriate enzymes and cloned into the vector pME101-thrA*1-serC restricted with the same restriction enzymes. The resulting vectors were named pME101-thrA*1-serC*(R42W/R77T) and pME101-thrA*1-serC*(R42W/R77W).

Construction of Strains 5 and 6

The plasmid pME101-thrA*1-serC*(R42W/R77T), described above and the plasmid pBBR1MCS5-Ptrc01/RBS01*2-yghD-kivDII-TT07, contained into strain DI0107c01 (strain described into patent application WO 2010/076324), were introduced simultaneously into strain DI0084c02, described into patent application WO 2010/076324, giving rise to strain 5.

The plasmids pME101-thrA*1-serC*(R42W/R77W), described above, and pBBR1MCS5-Ptrc01/RBS01*2-yqhD-kivDII-TT07 were introduced into strain D0084c02, giving rise to strain 6

Production of PDO of Strains 5 and 6 in Flask

Production strains were evaluated in small Erlenmeyer flasks using modified M9 medium (Anderson, 1946) that was supplemented with 4.5 mM threonine, 5 mM methionine, 10 $g \cdot L^{-1}$ MOPS and 10 $g \cdot L^{-1}$ glucose and adjusted to pH 6.8.

A 5 mL preculture was grown at 37° C. for 6.5 hours in a mixed medium (10% LB medium (Sigma 25%) with 2.5 $g \cdot L^{-1}$ glucose and 90% minimal medium described above). It was used to inoculate a 50 mL culture to an $OD_{600}$ of 0.1 in minimal medium. IPTG (100 μM) was also added for induction of the expression vector pME101. When necessary, antibiotics were added at concentrations of 10 $mg \cdot L^{-1}$ for gentamicin and of 50 $mg \cdot L^{-1}$ for spectinomycin. The temperature of the cultures was 37° C. When the culture had reached an $OD_{600}$ of 7 to 9, extracellular metabolites were analysed using HPLC with refractometric detection (organic acids and glucose). Production of 1,3-propanediol was determined by LC/MS/MS. For each strain, two repetitions were made.

The production of PDO was increased by a factor of 1.5 with the strain 6 and by 3 with the strain 5 compared to the reference strain (Table 4).

TABLE 4

PDO production in batch culture for the different strains.

| Strain | PDO (mM) |
|---|---|
| DI0107c01 | 0.08 |
| Strain 5 | 0.25 |
| Strain 6 | 0.12 |

Example 4: 2,4-Dihydroxybutyrate (DHB) Production by Overproduction of L-Homoserine Aminotransferase SerC* Mutants in *Escherichia coli*

Construction of Plasmid for Overexpression of the 2-Hydroxyacid-Dehydrogenase IdhA Gene from *Lactococcus lactis*

To overexpress the IdhA gene from *Lactococcus lactis*, the IdhA gene (SEQ ID NO: 41) encoding the protein of SEQ ID NO: 42, was expressed from a pBBR1MCS5 vector, previously described into patent application WO 2010/076324, using the artificial trc promoter, the same promoter as for overexpression of yqhD gene into the pBBR1MCS5-Ptrc01/RBS01*2-yhD-kivDII-TT07 plasmid.

For this purpose, the IdhA gene was amplified by PCR from *Lactococcus lactis* genomic DNA, using appropriate oligonucleotides. The PCR product was restricted using appropriate enzymes and cloned into the vector pBBR1MCS5 restricted with the same restriction enzymes. The resulting vector was named pBBR1MCS5-Ptrc01/RBS01*2-IdhAll.

Construction of 2,4-DHB Producer Strains 7, 8 and 9

The plasmids pME101-thrA*1-serC and pBBR1MCS5-Ptrc01/RBS01*2-IdhAll described above were introduced simultaneously into strain D10084c02, described into patent application WO 2010/076324, giving rise to strain 7.

The plasmids pME101-thrA*1-serC*(R42W/R77T) and pBBR1MCS5-Ptrc01/RBS01*2-IdhAll described above were introduced simultaneously into strain D10084c02, giving rise to strain 8.

The plasmids pME101-thrA*1-serC*(R42W/R77W) and pBBR1MCS5-Ptrc01/RBS01*2-IdhAll described above were introduced into strain D10084c02, giving rise to strain 9.

Production of 2,4-DHB of Strains 7, 8 and 9 in Flask

Production strains were evaluated in small Erlenmeyer flasks using modified M9 medium (Anderson, 1946) that was supplemented with 4.5 mM threonine, 5 mM methionine, 10 $g \cdot L^{-1}$ MOPS and 10 $g \cdot L^{-1}$ glucose and adjusted to pH 6.8.

A 5 mL preculture was grown at 37° C. for 6.5 hours in a mixed medium (10% LB medium (Sigma 25%) with 2.5 $g \cdot L^{-1}$ glucose and 90% minimal medium described above). It was used to inoculate a 50 mL culture to an $OD_{600}$ of 0.1 in minimal medium. IPTG (100 μM) was also added for induction of the expression vector pME101. When necessary, antibiotics were added at concentrations of 10 $mg \cdot L^{-1}$ for gentamicin and of 50 $mg \cdot L^{-1}$ for spectinomycin. The temperature of the cultures was 37° C. When the culture had reached an $OD_{600}$ of 7 to 9, extracellular metabolites were analysed using HPLC with refractometric detection (organic acids and glucose). Production of 2,4-DHB was determined by LC/MS/MS. For each strain, two repetitions were made.

The production of 2,4-DHB was increased by a factor of 2.5 with the strain 9 and by 7 with the strain 8 compared to the reference strain (Table 5).

TABLE 5

2,4-DHB production in batch culture for the different strains.

| Strain | 2,4-DHB (mM) |
|---|---|
| Strain 7 | 0.14 |
| Strain 8 | 1.05 |
| Strain 9 | 0.37 |

REFERENCES

Carrier T & Keasling J., (1999), *Biotechnol Prog.,* 15 (1): 58-64

Salis H., (2011), *Methods Enzymol.,* 498:19-42

Segel I., (1993), Enzyme kinetics, John Wiley & Sons, pp. 44-54 and 100-112

Case D. A., Darden T. A., Cheatham T. E., Simmerling C. L., Wang J., Duke R. E., Luo R., Crowley M., Walker R. C., Zhang W., Merz K. M., Wang B., Hayik S., Roitberg A., Seabra G., Kolossvery I., Wong K. F., Paesani F., Vanicek J., Wu X., Brozell S. R., Steinbrecher T., Gohlke H., Yang L., Tan C., Mongan J., Hornak V., Cui G., Mathews D. H., Seetin M. G., Sagui C., Babin V., and Kollman P. A., (2008) AMBER 10. University of California, San Francisco Kollman P. A., Massova I, Reyes C, Kuhn B., Huo S., Chong L., Lee M., Lee T., Duan Y., Wang W., Donini O., Cieplak P., Srinivasan J., Case D. A., and Cheatham T. E., (2000) Acc. Chem. Res. 33, 889-897.

Datsenko K. A. & Wanner B. L.; (2000). Proc Natl Acad Sci USA., 97 (12), 6640-6645.

Anderson E H; (1946). Proc Natl Acad Sci USA., 32 (5), 120-128.

Reinscheid D. J.; Eikmanns B. J.; Sahm H.; (1991). J Bacteriol., 173 (10), 3228-3230

The invention claimed is:

1. A genetically modified microorganism for the production of a derivative of 4-hydroxy-2-ketobutyrate selected from 1,3-propanediol, 3-hydroxypropionaldehyde, 3-hydroxypropionate and 2,4-dihydroxybutyrate, wherein said genetically modified microorganism further comprises a gene coding for a mutant phosphoserine aminotransferase having an improved L-homoserine aminotransferase activity converting by transamination L-homoserine into 4-hydroxy-2-ketobutyrate and wherein said mutant phosphoserine aminotransferase comprises amino acid R (Arg) at position 42, by reference to *E. coli* phosphoserine aminotransferase of SEQ ID NO: 2, replaced by a non-polar amino acid.

2. The genetically modified microorganism for the production of a derivative of 4-hydroxy-2-ketobutyrate selected from 1,3-propanediol, 3-hydroxypropionaldehyde, 3-hydroxypropionate and 2,4-dihydroxybutyrate of claim 1, wherein the mutant phosphoserine aminotransferase comprises a mutation wherein amino acid R (Arg) at position 42 is replaced with amino acid W (Trp).

3. The genetically modified microorganism for the production of a derivative of 4-hydroxy-2-ketobutyrate selected from 1,3-propanediol, 3-hydroxypropionaldehyde, 3-hydroxypropionate and 2,4-dihydroxybutyrate of claim 1, wherein the mutant phosphoserine aminotransferase further comprises a mutation where amino acid R (Arg) at position 77 is replaced by a polar uncharged or a non-polar amino acid.

4. The genetically modified microorganism for the production of a derivative of 4-hydroxy-2-ketobutyrate selected from 1,3-propanediol, 3-hydroxypropionaldehyde, 3-hydroxypropionate and 2,4-dihydroxybutyrate of claim 1, wherein the gene coding for the mutant phosphoserine aminotransferase is a modified gene endogenous to the said modified microorganism.

5. The genetically modified microorganism for the production of a derivative of 4-hydroxy-2-ketobutyrate selected from 1,3-propanediol, 3-hydroxypropionaldehyde, 3-hydroxypropionate and 2,4-dihydroxybutyrate of claim 1, wherein the gene coding for the mutant phosphoserine aminotransferase is a modified gene heterologous to the said modified microorganism.

6. The genetically modified microorganism for the production of a derivative of 4-hydroxy-2-ketobutyrate selected from 1,3-propanediol, 3-hydroxypropionaldehyde, 3-hydroxypropionate and 2,4-dihydroxybutyrate of claim 1, wherein the gene coding for a mutant phosphoserine aminotransferase is under control of a strong promoter.

7. The genetically modified microorganism for the production of a derivative of 4-hydroxy-2-ketobutyrate selected from 1,3-propanediol, 3-hydroxypropionaldehyde, 3-hydroxypropionate and 2,4-dihydroxybutyrate of claim 1, which comprises one or more copies of the gene coding for a mutant phosphoserine aminotransferase having an improved L-homoserine aminotransferase activity converting L-homoserine into 4-hydroxy-2-ketobutyrate by transamination.

8. The genetically modified microorganism for the production of a derivative of 4-hydroxy-2-ketobutyrate selected from 1,3-propanediol, 3-hydroxypropionaldehyde, 3-hydroxypropionate and 2,4-dihydroxybutyrate of claim 1, which is selected from Enterobacteriaceae, Clostridiaceae, Bacillaceae, Streptomycetaceae and Corynebacteriaceae.

9. The genetically modified microorganism for the production of a derivative of 4-hydroxy-2-ketobutyrate selected from 1,3-propanediol, 3-hydroxypropionaldehyde, 3-hydroxypropionate and 2,4-dihydroxybutyrate of claim 1, which is modified for the production of 1,3-propanediol from 4-hydroxy-2-ketobutyrate in a two-steps pathway by expressing:

- at least one gene encoding an enzyme having a 2-keto acid decarboxylase activity for the conversion of 4-hydroxy-2-ketobutyrate into 3-hydroxypropionaldehyde, and
- at least one gene encoding an enzyme having hydroxy aldehyde reductase activity for the conversion of 3-hydroxypropionaldehyde into 1,3-propanediol.

10. The genetically modified microorganism for the production of a derivative of 4-hydroxy-2-ketobutyrate selected 1,3-propanediol, 3-hydroxypropionaldehyde, 3-hydroxypropionate and 2,4-dihydroxybutyrate of claim 9 for the production of 1,3-propanediol from 4-hydroxy-2-ketobutyrate, which expresses at least one gene chosen among kivD gene from *Lactococcus lactis* and pdc gene from *Zymomonas mobilis*, and at least the yqhD gene from *Escherichia coli*.

11. The genetically modified microorganism for the production of a derivative of 4-hydroxy-2-ketobutyrate selected from 1,3-propanediol, 3-hydroxypropionaldehyde, 3-hydroxypropionate and 2,4-dihydroxybutyrate of claim 1, which is modified for the production of 3-hydroxypropionaldehyde from 4-hydroxy-2-ketobutyrate in a one-step of conversion by expressing at least one gene encoding an enzyme with 2-keto acid decarboxylase activity for the conversion of 4-hydroxy-2-ketobutyrate into 3-hydroxypropionaldehyde.

12. The genetically modified microorganism for the production of a derivative of 4-hydroxy-2-ketobutyrate selected from 1,3-propanediol, 3-hydroxypropionaldehyde, 3-hydroxypropionate and 2,4-dihydroxybutyrate of claim 1, which is modified for the production of 3-hydroxypropionate from 4-hydroxy-2-ketobutyrate in a two-steps pathway by expressing at least one gene encoding an enzyme with 2-keto acid decarboxylase activity for the conversion of 4-hydroxy-2-ketobutyrate into 3-hydroxypropionaldehyde and at least one gene encoding an enzyme with hydroxyl aldehyde dehydrogenase activity for the conversion of 3-hydroxypropionaldehyde into 3-hydroxypropionate.

13. The genetically modified microorganism for the production of a derivative of 4-hydroxy-2-ketobutyrate selected from 1,3-propanediol, 3-hydroxypropionaldehyde, 3-hydroxypropionate and 2,4-dihydroxybutyrate of claim 1, which is modified for the production of 2,4-dihydroxybutyrate from 4-hydroxy-2-ketobutyrate in a one-step pathway by expressing at least one gene encoding an enzyme having 4-hydroxy-2-ketobutyrate reductase activity for the conversion of 4-hydroxy-2-ketobutyrate into 2,4-dihydroxybutyrate.

14. The genetically modified microorganism for the production of a derivative of 4-hydroxy-2-ketobutyrate selected from 1,3-propanediol, 3-hydroxypropionaldehyde, 3-hydroxypropionate and 2,4-dihydroxybutyrate of claim 13 for the production of 2,4-dihydroxybutyrate from 4-hydroxy-2-ketobutyrate, which expresses at least one gene selected from ldhA from *Oryctalagus cuniculus*, ldhA from *Lactococcus lactis*, lldH from *Geobacillus stearothermophilus*, ldh from *Bacillus subtilis* or ldhA from *Escherichia coli*, mdh from *Escherichia coli* and panE from *Lactococcus lactis*.

15. A method for the production of derivatives of 4-hydroxy-2-ketobutyrate selected from 1,3-propanediol, 3-hydroxypropionaldehyde, 3-hydroxypropionate and 2,4-dihydroxybutyrate comprising:

- culturing in a culture medium comprising a source of carbon a microorganism genetically modified for the production of the desired derivatives of 4-hydroxy-2-ketobutyrate and further comprising a gene coding for a mutant phosphoserine aminotransferase having an improved L-homoserine aminotransferase activity converting by transamination L-homoserine into 4-hydroxy-2-ketobutyrate wherein said mutant phosphoserine aminotransferase comprises amino acid R (Arg) at position 42, by reference to *E. coli* phosphoserine aminotransferase of SEQ ID NO: 2, replaced by a non-polar amino acid, and
- recovering the desired derivative of 4-hydroxy-2-ketobutyrate from the culture medium.

16. The genetically modified microorganism for the production of a derivative of 4-hydroxy-2-ketobutyrate selected from 1,3-propanediol, 3-hydroxypropionaldehyde, 3-hydroxypropionate and 2,4-dihydroxybutyrate of claim 11, which is modified for the production of 3-hydroxypropionaldehyde from 4-hydroxy-2-ketobutyrate in a one-step of conversion by expressing at least one gene encoding an enzyme with 2-keto acid decarboxylase activity for the conversion of 4-hydroxy-2-ketobutyrate into 3-hydroxypropionaldehyde which is selected from kivD gene from *Lactococcus lactis* and pdc gene from *Zymomonas mobilis*.

17. The genetically modified microorganism for the production of a derivative of 4-hydroxy-2-ketobutyrate selected from 1,3-propanediol, 3-hydroxypropionaldehyde, 3-hydroxypropionate and 2,4-dihydroxybutyrate of claim 12, which is modified for the production of 3-hydroxypropionate from 4-hydroxy-2-ketobutyrate in a two-steps pathway by expressing at least one gene encoding an enzyme with 2-keto acid decarboxylase activity for the conversion of 4-hydroxy-2-ketobutyrate into 3-hydroxypropionaldehyde which is selected from an *Escherichia coli* overexpressing kivD gene from *Lactococcus lactis* and ald4 gene from *Saccharomyces cerevisiae*.

18. The method for the production of derivatives of 4-hydroxy-2-ketobutyrate selected from 1,3-propanediol, 3-hydroxypropionaldehyde, 3-hydroxypropionate and 2,4-dihydroxybutyrate of claim 15, wherein the mutant phosphoserine aminotransferase comprises a mutation wherein amino acid R (Arg) at position 42 is replaced with amino acid W (Trp).

19. The method for the production of derivatives of 4-hydroxy-2-ketobutyrate selected from 1,3-propanediol, 3-hydroxypropionaldehyde, 3-hydroxypropionate and 2,4-dihydroxybutyrate of claim 15, wherein the mutant phosphoserine aminotransferase further comprises a mutation where amino acid R (Arg) at position 77 is replaced by a polar uncharged or a non-polar amino acid, preferably with amino acid T (Thr) or W (Trp).

20. The method for the production of derivatives of 4-hydroxy-2-ketobutyrate selected from 1,3-propanediol, 3-hydroxypropionaldehyde, 3-hydroxypropionate and 2,4-dihydroxybutyrate of claim 15, wherein the microorganism genetically modified for the production of the desired derivatives of 4-hydroxy-2-ketobutyrate is selected from Enterobacteriaceae, Clostridiaceae, Bacillaceae, Streptomycetaceae and Corynebacteriaceae.

* * * * *